United States Patent
Zhang

(10) Patent No.: US 10,987,414 B2
(45) Date of Patent: Apr. 27, 2021

(54) ADHESIN TIP MULTIEPITOPE FUSION ANTIGEN PLATFORM AND VACCINES AND THEIR USE IN THE TREATMENT OF ENTEROTOXIGENIC DIARRHEA

(71) Applicant: Kansas State University Research Foundation, Manhattan, KS (US)

(72) Inventor: Weiping Zhang, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 16/085,884

(22) PCT Filed: Mar. 20, 2017

(86) PCT No.: PCT/US2017/023183
§ 371 (c)(1),
(2) Date: Sep. 17, 2018

(87) PCT Pub. No.: WO2017/161366
PCT Pub. Date: Sep. 21, 2017

(65) Prior Publication Data
US 2019/0091318 A1 Mar. 28, 2019

Related U.S. Application Data

(60) Provisional application No. 62/310,417, filed on Mar. 18, 2016.

(51) Int. Cl.
| | |
|---|---|
| *A61K 39/00* | (2006.01) |
| *A61K 39/02* | (2006.01) |
| *A61K 39/108* | (2006.01) |
| *C07K 14/245* | (2006.01) |
| *C07K 19/00* | (2006.01) |
| *A61P 31/04* | (2006.01) |

(52) U.S. Cl.
CPC .......... *A61K 39/0258* (2013.01); *A61P 31/04* (2018.01); *C07K 14/245* (2013.01); *C07K 19/00* (2013.01); *A61K 2039/6037* (2013.01); *A61K 2039/70* (2013.01); *C07K 2319/40* (2013.01); *Y02A 50/30* (2018.01)

(58) Field of Classification Search
CPC ..... A61K 39/00; A61K 39/02; A61K 30/0258
USPC .............................. 424/184.1, 234.1, 241.1
See application file for complete search history.

(56) References Cited

FOREIGN PATENT DOCUMENTS

WO 2015095335 A1 6/2015

OTHER PUBLICATIONS

Ruan, X., et al., (Clinical and Vaccine Immunology, vol. 21, No. 2, Feb. 2014, pp. 243-249).*
Li et al. A Receptor-binding Site as Revealed by the Crystal Structure of CfaE, the Colonization Factor Antigen I Fimbrial Adhesin of Enterotoxigenic *Escherichia coli*. J Biol Chem Aug. 17, 2007, vol. 282 No. 33, pp. 23970-23980.

* cited by examiner

*Primary Examiner* — Rodney P Schwartz
(74) *Attorney, Agent, or Firm* — Tracey S. Truitt; Armstrong Teasdale LLP

(57) ABSTRACT

The application provides for MEFA constructs and vaccines against Enterotoxigenic *Escherichia coli* (ETEC). Methods for reducing the incidence of diarrhea associated with ETEC are also provided. The representative adhesin tip MEFAs and the representative major subunit CFA MEFA-II provided in the disclosure has an adhesin tip backbone or major subunit CFA with one or more adhesin tips, adhesin subunit or major structural subunit epitopes incorporated onto the backbone. The adhesin tip MEFAs and the CFA MEFA-II provided advantageously prevents the ETEC molecule from attaching to the intestine.

13 Claims, 8 Drawing Sheets
Specification includes a Sequence Listing.

SEQUENCE LISTING

<160> NUMBER OF SEQ ID NOS: 121

<210> SEQ ID NO 1
<211> LENGTH: 361
<212> TYPE: PRT
<213> ORGANISM: Escherichia coli

<400> SEQUENCE: 1

```
Met Asn Lys Ile Leu Phe Ile Phe Thr Leu Phe Phe Ser Ser Gly Phe
1               5                   10                  15

Phe Thr Phe Ala Val Ser Ala Asp Lys Asn Asp Ile Gly Arg Leu Gln
            20                  25                  30

Ser Asp Ala Glu Tyr Pro His Asp Arg Asn Ile Thr Leu Asp Lys Asn
        35                  40                  45

Ala Gly Asn Thr Ser Tyr Leu Thr Ala Tyr Asn Gly Gln Phe Thr Glu
    50                  55                  60

Lys Arg Ser Leu Ile Lys Arg Cys Leu Ser Ser Gln Asn Thr Leu Asn
65                  70                  75                  80
```

```
Gly Ala Cys Pro Ser Ser Asp Ala Pro Gly Thr Ala Thr Ile Asp Gly
             85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Tyr Asp Ser
        115                 120                 125

Asp Pro Lys Leu Asp Ser Gln Asn Ser Ser His Phe Gln Cys Asn Arg
    130                 135                 140

Glu Gln Ala Ser Gly Ala Thr Val Ala Met Lys Asp Ala Tyr Gln Arg
145                 150                 155                 160

Asp Gly Lys Tyr Pro Asp Phe Gly Gly Val Trp Asn Ala Val Glu Gly
                165                 170                 175

Glu Lys Ser Pro Arg Arg Gly Val Thr Thr Tyr Gly Thr Tyr Thr Ile
            180                 185                 190

Asn Ile Thr Val Asn Leu Thr Asp Lys Gly Asn Ile Gln Ile Trp Leu
        195                 200                 205

Pro Gln Phe Lys Ser Asn Ala Arg Val Asp Leu Asn Leu Arg Pro Thr
210                 215                 220

Gly Gly Thr Tyr Ile Gly Arg Asn Ser Val Asp Met Cys Phe Tyr
225                 230                 235                 240

Leu Arg Lys Ile Asn Asp Asp Thr Lys Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Ser
        275                 280                 285

Gln Ser Ile Glu Met Arg Phe Gln Asp Asp Ser Gln Ile Asn Thr Ala
290                 295                 300

Ser Leu Glu Thr Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
                325                 330                 335

Lys Val Lys Asn Pro Glu Ala Gly Gln Tyr Met Gly Asn Ile Lys Ile
            340                 345                 350

Thr Phe Thr Pro Ser Ser Gln Thr Leu
        355                 360

<210> SEQ ID NO 2
<211> LENGTH: 400
<212> TYPE: PRT
<213> ORGANISM: Escherichia coli
<220> FEATURE:
<221> NAME/KEY: MISC_FEATURE
<222> LOCATION: (35)..(45)
<223> OTHER INFORMATION: Epitope

<400> SEQUENCE: 2

Met Asn Arg Ile Tyr Lys Leu Lys Phe Asp Lys Arg Asn Glu Leu
1                5                  10                  15

Val Val Val Ser Glu Ile Thr Thr Gly Val Gly Asn Ala Lys Ala Thr
            20                  25                  30

Gly Ser Val Glu Gly Glu Lys Ser Pro Arg Arg Gly Val Arg Ala Met
        35                  40                  45

Ala Leu Ser Leu Leu Ser Gly Met Met Ile Met Ala His Pro Ala Met
50                  55                  60
```

Ser Ala Asn Leu Pro Thr Gly Gly Gln Ile Val Ala Gly Ser Gly Ser
65                  70                  75                  80

Ile Gln Thr Pro Ser Gly Asn Gln Met Asn Ile His Gln Asn Ser Gln
            85                  90                  95

Asn Met Val Ala Asn Trp Asn Ser Phe Asp Ile Gly Lys Gly Asn Thr
            100                 105                 110

Val Gln Phe Asp Gln Pro Ser Ser Ala Val Ala Leu Asn Arg Val
        115                 120                 125

Val Gly Gly Gly Glu Ser Gln Ile Met Gly Asn Leu Lys Ala Asn Gly
    130                 135                 140

Gln Val Phe Leu Val Asn Pro Asn Gly Val Leu Phe Gly Glu Gly Ala
145                 150                 155                 160

Ser Val Ser Thr Ser Gly Phe Val Ala Ser Thr Arg Asp Ile Lys Asn
                165                 170                 175

Asp Asp Phe Met Asn Arg Arg Tyr Thr Phe Ser Gly Gly Gln Lys Ala
            180                 185                 190

Gly Ala Ala Ile Val Asn Gln Gly Glu Leu Thr Thr Asn Ala Gly Gly
        195                 200                 205

Tyr Ile Val Leu Ala Ala Asp Arg Val Ser Asn Ser Gly Thr Ile Arg
    210                 215                 220

Thr Pro Gly Gly Lys Thr Val Leu Ala Ala Ser Glu Arg Ile Thr Leu
225                 230                 235                 240

Gln Leu Asp Asn Gly Gly Leu Met Ser Val Gln Val Thr Gly Asp Val
                245                 250                 255

Val Asn Ala Leu Val Glu Asn Arg Gly Leu Val Ser Ala Arg Asp Gly
            260                 265                 270

Gln Val Tyr Leu Thr Ala Leu Gly Arg Gly Met Leu Met Asn Thr Val
        275                 280                 285

Leu Asn Val Ser Gly Val Val Glu Ala Ser Gly Met His Arg Gln Asp
    290                 295                 300

Gly Asn Ile Val Leu Asp Gly Gly Asp Ser Gly Val Val His Leu Ser
305                 310                 315                 320

Gly Thr Leu Gln Ala Asp Asn Ala Ser Gly Gln Gly Gly Lys Val Val
                325                 330                 335

Val Gln Gly Lys Asn Ile Leu Leu Asp Lys Gly Ser Asn Ile Thr Ala
            340                 345                 350

Thr Gly Gly Gln Gly Gly Gly Glu Val Tyr Val Gly Gly Gly Trp Gln
        355                 360                 365

Gly Lys Asp Ser Asn Ile Arg Asn Ala Asp Lys Val Val Met Gln Gly
    370                 375                 380

Gly Ala Arg Ile Asp Val Ser Ala Thr Gln Gln Gly Asn Gly Gly Thr
385                 390                 395                 400

<210> SEQ ID NO 3
<211> LENGTH: 31
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 3
ctagctagcg ggcgataccc ggaaactaca g                          31

<210> SEQ ID NO 4

```
<211> LENGTH: 29
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restricted Site

<400> SEQUENCE: 4
gatcggccgt cataaatttt cgacactgg                                    29

<210> SEQ ID NO 5
<211> LENGTH: 31
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restricted Site

<400> SEQUENCE: 5
ctagctagcc aatcatggca tacgaacgta g                                 31

<210> SEQ ID NO 6
<211> LENGTH: 32
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 6
gatcggccgt tacagacttg aactactagg ag                                32

<210> SEQ ID NO 7
<211> LENGTH: 47
<212> TYPE: DNA
<213> ORGANISM: Escherichia coli
<220> FEATURE:
<221> NAME/KEY: misc_feature
<222> LOCATION: (9)..(14)
<223> OTHER INFORMATION: Restriction Site

<400> SEQUENCE: 7
agttacatcc atgggcactc taaccaaaga actggcatta aatgtgc                47

<210> SEQ ID NO 8
<211> LENGTH: 44
<212> TYPE: DNA
<213> ORGANISM: Escherichia coli
<220> FEATURE:
<221> NAME/KEY: misc_feature
<222> LOCATION: (9)..(14)
<223> OTHER INFORMATION: Restriction Site

<400> SEQUENCE: 8
tacatgatcg gccgttaatt acctgaaact aaatgttcgt tacc                   44

<210> SEQ ID NO 9
<211> LENGTH: 32
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 9
```

```
ctagctagcg ataaaattcc cggagatgaa ag                                      32
```

<210> SEQ ID NO 10
<211> LENGTH: 34
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 10

```
gatcggccgc tagagtgttt gactacttgg tgtg                                    34
```

<210> SEQ ID NO 11
<211> LENGTH: 30
<212> TYPE: DNA
<213> ORGANISM: Escherichia coli
<220> FEATURE:
<221> NAME/KEY: misc_feature
<222> LOCATION: (5)..(10)
<223> OTHER INFORMATION: Restriction Site

<400> SEQUENCE: 11

```
ttttccatgg ttatggttca ggctgctaca                                         30
```

<210> SEQ ID NO 12
<211> LENGTH: 30
<212> TYPE: DNA
<213> ORGANISM: Escherichia coli
<220> FEATURE:
<221> NAME/KEY: misc_feature
<222> LOCATION: (5)..(10)
<223> OTHER INFORMATION: Restriction Site

<400> SEQUENCE: 12

```
agatcggccg ttatttattg taacatttcc                                         30
```

<210> SEQ ID NO 13
<211> LENGTH: 44
<212> TYPE: DNA
<213> ORGANISM: Escherichia coli
<220> FEATURE:
<221> NAME/KEY: misc_feature
<222> LOCATION: (9)..(14)
<223> OTHER INFORMATION: Restriction Site

<400> SEQUENCE: 13

```
agttacatcc atgggctggc aatataaatc tctggatgta aatg                         44
```

<210> SEQ ID NO 14
<211> LENGTH: 45
<212> TYPE: DNA
<213> ORGANISM: Escherichia coli
<220> FEATURE:
<221> NAME/KEY: misc_feature
<222> LOCATION: (9)..(14)
<223> OTHER INFORMATION: Restriction Site

<400> SEQUENCE: 14

```
atgtagatcg gccgttaagt caaatttcct gcataagtac cagac                        45
```

<210> SEQ ID NO 15
<211> LENGTH: 34
<212> TYPE: DNA
<213> ORGANISM: Escherichia coli
<220> FEATURE:

```
<221> NAME/KEY: misc_feature
<222> LOCATION: (4)..(9)
<223> OTHER INFORMATION: Restriction Site

<400> SEQUENCE: 15
ctagctagca tgagcctgct ggaagttatc attg                              34

<210> SEQ ID NO 16
<211> LENGTH: 32
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 16
gatcggccgt taacggctac ctaaagtaat tg                                32

<210> SEQ ID NO 17
<211> LENGTH: 33
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 17
ctagctagcg gcgtgggtaa tgcaaaagcc acg                               33

<210> SEQ ID NO 18
<211> LENGTH: 28
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 18
ctagctagcg ataaaaatcc cggaagtg                                     28

<210> SEQ ID NO 19
<211> LENGTH: 29
<212> TYPE: DNA
<213> ORGANISM: Escherichia coli
<220> FEATURE:
<221> NAME/KEY: misc_feature
<222> LOCATION: (4)..(9)
<223> OTHER INFORMATION: Restriction Site

<400> SEQUENCE: 19
gatcggccgc tagagtgttt gactacttg                                    29

<210> SEQ ID NO 20
<211> LENGTH: 386
<212> TYPE: PRT
<213> ORGANISM: Escherichia coli
<220> FEATURE:
<221> NAME/KEY: MISC_FEATURE
<222> LOCATION: (24)..(39)
<223> OTHER INFORMATION: Epitopes
<220> FEATURE:
<221> NAME/KEY: MISC_FEATURE
<222> LOCATION: (91)..(106)
<223> OTHER INFORMATION: Epitope
<220> FEATURE:
<221> NAME/KEY: MISC_FEATURE
```

```
<222> LOCATION: (149)..(158)
<223> OTHER INFORMATION: Epitope
<220> FEATURE:
<221> NAME/KEY: MISC_FEATURE
<222> LOCATION: (231)..(243)
<223> OTHER INFORMATION: Epitope
<220> FEATURE:
<221> NAME/KEY: MISC_FEATURE
<222> LOCATION: (268)..(277)
<223> OTHER INFORMATION: Epitope
<220> FEATURE:
<221> NAME/KEY: MISC_FEATURE
<222> LOCATION: (303)..(316)
<223> OTHER INFORMATION: Epitope
<220> FEATURE:
<221> NAME/KEY: MISC_FEATURE
<222> LOCATION: (355)..(370)
<223> OTHER INFORMATION: Epitope

<400> SEQUENCE: 20
```

| | | | | | | | | | | | | | | |
|---|---|---|---|---|---|---|---|---|---|---|---|---|---|---|
| Met | Asn | Lys | Ile | Leu | Phe | Ile | Phe | Thr | Leu | Phe | Ser | Ser | Val | Leu |
| 1 | | | | 5 | | | | | 10 | | | | | 15 |
| Phe | Thr | Phe | Ala | Val | Ser | Ala | Gln | Glu | Gly | Ser | Ser | Asn | Arg | Ala | Lys |
| | | | 20 | | | | | 25 | | | | | 30 | |
| Ile | Asp | Gln | Thr | Gly | Asp | Tyr | Thr | Asn | Ile | Phe | Gly | Pro | Arg | Asp | Arg |
| | | | 35 | | | | | 40 | | | | | 45 | |
| Asn | Glu | Ser | Ser | Pro | Lys | His | Asn | Ile | Leu | Asn | Asp | Tyr | Ile | Thr | Ala |
| 50 | | | | | 55 | | | | | 60 | | | | |
| Tyr | Ser | Glu | Ser | His | Thr | Leu | Tyr | Asp | Arg | Met | Ile | Phe | Leu | Cys | Leu |
| 65 | | | | | 70 | | | | | 75 | | | | | 80 |
| Ser | Ser | Gln | Asn | Thr | Leu | Asn | Gly | Ala | Cys | Pro | Thr | Ser | Glu | Asn | Pro |
| | | | | 85 | | | | | 90 | | | | | 95 | |
| Ser | Ser | Ser | Ser | Val | Ser | Gly | Glu | Thr | Asn | Ile | Thr | Leu | Gln | Phe | Thr |
| | | | 100 | | | | | 105 | | | | | 110 | | |
| Glu | Lys | Arg | Ser | Leu | Ile | Lys | Arg | Glu | Leu | Gln | Ile | Lys | Gly | Tyr | Lys |
| | | | 115 | | | | | 120 | | | | | 125 | | |
| Arg | Leu | Leu | Phe | Lys | Gly | Ala | Asn | Cys | Pro | Ser | Tyr | Leu | Thr | Leu | Asn |
| | | 130 | | | | | 135 | | | | | 140 | | | |
| Ser | Ala | His | Tyr | Asn | Lys | Asp | Gly | Glu | Gly | Val | Ser | Pro | Gly | Gly | Ala |
| 145 | | | | | 150 | | | | | 155 | | | | | 160 |
| Ser | Leu | Tyr | Leu | Tyr | Ile | Pro | Ala | Gly | Glu | Leu | Lys | Asn | Leu | Pro | Phe |
| | | | 165 | | | | | 170 | | | | | 175 | | |
| Gly | Gly | Ile | Trp | Asp | Ala | Thr | Leu | Lys | Leu | Arg | Val | Lys | Arg | Arg | Tyr |
| | | | 180 | | | | | 185 | | | | | 190 | | |
| Asp | Gln | Thr | Tyr | Gly | Thr | Tyr | Thr | Ile | Asn | Ile | Thr | Val | Lys | Leu | Thr |
| | | | 195 | | | | | 200 | | | | | 205 | | |
| Asp | Lys | Gly | Asn | Ile | Gln | Ile | Trp | Leu | Pro | Gln | Phe | Lys | Ser | Asp | Ala |
| | | 210 | | | | | 215 | | | | | 220 | | | |
| Arg | Val | Asp | Leu | Asn | Leu | Ser | Phe | Gln | Ala | Pro | Arg | Gln | Asp | Arg | Ser |
| 225 | | | | | 230 | | | | | 235 | | | | | 240 |
| Val | Gln | Ser | Gly | Arg | Asn | Ser | Val | Asp | Met | Cys | Phe | Tyr | Asp | Gly | Tyr |
| | | | | 245 | | | | | 250 | | | | | 255 | |
| Ser | Thr | Asn | Ser | Ser | Ser | Leu | Glu | Leu | Arg | Phe | Gln | Asp | Asn | Asn | Pro |
| | | | 260 | | | | | 265 | | | | | 270 | | |
| Lys | Ser | Asp | Gly | Lys | Phe | Tyr | Leu | Arg | Lys | Ile | Asn | Asp | Thr | Lys |
| | | 275 | | | | | 280 | | | | | 285 | | |
| Glu | Ile | Ala | Tyr | Thr | Leu | Ser | Leu | Leu | Leu | Ala | Gly | Lys | Ser | Ala | Gly |
| | 290 | | | | | 295 | | | | | 300 | | | | |
| Asn | Lys | Lys | Pro | Ile | Trp | Glu | Asn | Gln | Ser | Cys | Asp | Asn | Ile | Ala | Asp |

```
                305                 310                 315                 320
Ala Ala Ser Leu Glu Ile Asn Trp Asn Arg Ile Thr Ala Val Thr Met
                    325                 330                 335

Pro Glu Ile Ser Val Pro Val Leu Cys Trp Pro Gly Arg Leu Gln Leu
                340                 345                 350

Asp Ala Lys Lys Ser Pro Asp Ile Glu Asp Tyr Gln Glu Arg Pro Ala
                355                 360                 365

Asn Gly Tyr Met Gly Asn Ile Asn Ile Thr Phe Thr Pro Ser Ser Gln
            370                 375                 380

Thr Leu
385

<210> SEQ ID NO 21
<211> LENGTH: 361
<212> TYPE: PRT
<213> ORGANISM: Escherichia coli
<220> FEATURE:
<221> NAME/KEY: MISC_FEATURE
<222> LOCATION: (23)..(33)
<223> OTHER INFORMATION: Epitope
<220> FEATURE:
<221> NAME/KEY: MISC_FEATURE
<222> LOCATION: (84)..(99)
<223> OTHER INFORMATION: Epitope
<220> FEATURE:
<221> NAME/KEY: MISC_FEATURE
<222> LOCATION: (141)..(150)
<223> OTHER INFORMATION: Epitope
<220> FEATURE:
<221> NAME/KEY: MISC_FEATURE
<222> LOCATION: (221)..(231)
<223> OTHER INFORMATION: Epitope
<220> FEATURE:
<221> NAME/KEY: MISC_FEATURE
<222> LOCATION: (255)..(264)
<223> OTHER INFORMATION: Epitope
<220> FEATURE:
<221> NAME/KEY: MISC_FEATURE
<222> LOCATION: (289)..(299)
<223> OTHER INFORMATION: Epitope
<220> FEATURE:
<221> NAME/KEY: MISC_FEATURE
<222> LOCATION: (336)..(346)
<223> OTHER INFORMATION: Epitope

<400> SEQUENCE: 21

Met Asn Lys Ile Leu Phe Ile Phe Thr Leu Phe Phe Ser Ser Val Leu
1               5                   10                  15

Phe Thr Phe Ala Val Ser Ala Asp Lys Ile Pro Gly Asp Glu Asn Ile
                20                  25                  30

Thr Asn Ile Phe Gly Pro Arg Asp Arg Asn Glu Ser Ser Pro Lys His
            35                  40                  45

Asn Ile Leu Asn Asp Tyr Ile Thr Ala Tyr Ser Glu Ser His Thr Leu
        50                  55                  60

Tyr Asp Arg Met Ile Phe Leu Cys Leu Ser Ser Gln Asn Thr Leu Asn
65                  70                  75                  80

Gly Ala Cys Pro Thr Ser Glu Asn Pro Ser Ser Ser Val Ser Gly
                85                  90                  95

Glu Thr Asn Ile Thr Leu Gln Phe Thr Glu Lys Arg Ser Leu Ile Lys
                100                 105                 110

Arg Glu Leu Gln Ile Lys Gly Tyr Lys Arg Leu Leu Phe Lys Gly Ala
            115                 120                 125

Asn Cys Pro Ser Tyr Leu Thr Leu Asn Ser Ala His Tyr Thr Cys Asn
        130                 135                 140
```

```
Arg Asn Ser Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
            165                 170                 175

Leu Arg Val Lys Arg Arg Tyr Asp Gln Thr Tyr Gly Thr Tyr Thr Ile
        180                 185                 190

Asn Ile Thr Val Lys Leu Thr Asp Lys Gly Asn Ile Gln Ile Trp Leu
            195                 200                 205

Pro Gln Phe Lys Ser Asp Ala Arg Val Asp Leu Asn Leu Arg Pro Thr
        210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Leu Arg Phe Gln Asp
            245                 250                 255

Asn Asn Pro Lys Ser Asp Gly Lys Phe Tyr Leu Arg Lys Ile Asn Asp
            260                 265                 270

Asp Thr Lys Glu Ile Ala Tyr Thr Leu Ser Leu Leu Ala Gly Lys
            275                 280                 285

Ser Leu Thr Pro Thr Asn Gly Thr Ser Leu Asn Ile Ala Asp Ala Ala
290                 295                 300

Ser Leu Glu Ile Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
            325                 330                 335

Lys Val Glu Asn Pro Glu Ala Gly Gln Tyr Met Gly Asn Ile Asn Ile
            340                 345                 350

Thr Phe Thr Pro Ser Ser Gln Thr Leu
            355                 360

<210> SEQ ID NO 22
<211> LENGTH: 16
<212> TYPE: PRT
<213> ORGANISM: Escherichia coli

<400> SEQUENCE: 22

Gln Glu Gly Ser Ser Asn Arg Ala Lys Ile Asp Gln Thr Gly Asp Tyr
1               5                   10                  15

<210> SEQ ID NO 23
<211> LENGTH: 16
<212> TYPE: PRT
<213> ORGANISM: Escherichia coli

<400> SEQUENCE: 23

Pro Thr Ser Glu Asn Pro Ser Ser Ser Val Ser Gly Glu Thr Asn
1               5                   10                  15

<210> SEQ ID NO 24
<211> LENGTH: 10
<212> TYPE: PRT
<213> ORGANISM: Escherichia coli

<400> SEQUENCE: 24

Asn Lys Asp Gly Glu Gly Val Ser Pro Gly
1               5                   10

<210> SEQ ID NO 25
<211> LENGTH: 13
```

<212> TYPE: PRT
<213> ORGANISM: Escherichia coli

<400> SEQUENCE: 25

Ser Phe Gln Ala Pro Arg Gln Asp Arg Ser Val Gln Ser
1               5                   10

<210> SEQ ID NO 26
<211> LENGTH: 10
<212> TYPE: PRT
<213> ORGANISM: Escherichia coli

<400> SEQUENCE: 26

Gln Asp Asn Asn Pro Lys Ser Asp Gly Lys
1               5                   10

<210> SEQ ID NO 27
<211> LENGTH: 14
<212> TYPE: PRT
<213> ORGANISM: Escherichia coli

<400> SEQUENCE: 27

Ala Gly Asn Lys Lys Pro Ile Trp Glu Asn Gln Ser Cys Asp
1               5                   10

<210> SEQ ID NO 28
<211> LENGTH: 16
<212> TYPE: PRT
<213> ORGANISM: Escherichia coli

<400> SEQUENCE: 28

Lys Lys Ser Pro Asp Ile Glu Asp Tyr Gln Glu Arg Pro Ala Asn Gly
1               5                   10                  15

<210> SEQ ID NO 29
<211> LENGTH: 151
<212> TYPE: PRT
<213> ORGANISM: Escherichia coli
<220> FEATURE:
<221> NAME/KEY: MISC_FEATURE
<222> LOCATION: (73)..(88)
<223> OTHER INFORMATION: Epitope

<400> SEQUENCE: 29

Met Lys Asn Lys Leu Leu Phe Met Met Leu Thr Ile Leu Gly Ala Pro
1               5                   10                  15

Gly Ile Ala Ala Ala Ala Gly Tyr Asp Leu Ala Asn Ser Glu Tyr Asn
                20                  25                  30

Phe Ala Val Asn Glu Leu Ser Lys Ser Ser Phe Asn Gln Ala Ala Ile
            35                  40                  45

Ile Gly Gln Ala Gly Thr Asn Asn Ser Ala Gln Leu Arg Gln Gly Gly
        50                  55                  60

Ser Lys Leu Leu Ala Val Val Ala Gln Glu Gly Ser Ser Asn Arg Ala
65                  70                  75                  80

Lys Ile Asp Gln Thr Gly Asp Tyr Asn Leu Ala Tyr Ile Asp Gln Ala
                85                  90                  95

Gly Ser Ala Asn Asp Ala Ser Ile Ser Gln Gly Ala Tyr Gly Asn Thr
            100                 105                 110

Ala Met Ile Ile Gln Lys Gly Ser Gly Asn Lys Ala Asn Ile Thr Gln
        115                 120                 125

Tyr Gly Thr Gln Lys Thr Ala Ile Val Val Gln Arg Gln Ser Gln Met
    130                 135                 140

Ala Ile Arg Val Thr Gln Arg
145                 150

<210> SEQ ID NO 30
<211> LENGTH: 177
<212> TYPE: PRT
<213> ORGANISM: Escherichia coli
<220> FEATURE:
<221> NAME/KEY: MISC_FEATURE
<222> LOCATION: (155)..(164)
<223> OTHER INFORMATION: Epitope

<400> SEQUENCE: 30

Met Leu Lys Arg Ile Ser Cys Ile Ile Phe Val Phe Ser Gly Leu
1               5                   10                  15

Ile Tyr Ala Ala Glu Ile Thr Asn Gln Ile Glu Leu Ser Val Lys Val
                20                  25                  30

Asn Ile Ser Lys Pro Met Cys Lys Leu Asn Ser Gly Thr Gln Thr Ile
            35                  40                  45

Asp Phe Gly Asp Phe Asp Val Leu Asp Ile Ile Thr Glu Asn Arg Lys
        50                  55                  60

Leu Asn Gly His Ala Thr Phe Lys Phe Thr Glu Cys Ser Ser Val Lys
65                  70                  75                  80

Asn Met Lys Ile Lys Phe Lys Gln Ala Gly Gln Asn Pro Ala Leu Asp
                85                  90                  95

Ile Val Asn Asn Tyr Ile Pro Asn Ser Lys Gly Asp Arg Met Ala Lys
            100                 105                 110

Gly Val Ala Val Lys Leu Leu Asp Asp Lys Lys Gln Glu Ile Gln Leu
        115                 120                 125

Asn Lys Glu Met Asn Val Ile Val Glu Glu Ser Leu Thr Phe Lys Asp
130                 135                 140

Leu Thr Leu Asn Ala Gln Val Ile Ser Ile Asn Lys Asp Gly Glu Gly
145                 150                 155                 160

Val Ser Pro Gly Leu Leu Gln Thr Ala Ile Gly Met Glu Ile Ser Tyr
                165                 170                 175

Glu

<210> SEQ ID NO 31
<211> LENGTH: 363
<212> TYPE: PRT
<213> ORGANISM: Escherichia coli
<220> FEATURE:
<221> NAME/KEY: MISC_FEATURE
<222> LOCATION: (32)..(44)
<223> OTHER INFORMATION: Epitope

<400> SEQUENCE: 31

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
                20                  25                  30

Phe Gln Ala Pro Arg Gln Asp Arg Ser Val Gln Ser Pro Ile Tyr Asn
            35                  40                  45

Ile Phe Thr Asn His Val Ala Gly Tyr Ser Leu Ser His Asn Leu Tyr
        50                  55                  60

Asp Arg Ile Val Phe Leu Cys Thr Ser Ser Asn Pro Val Asn Gly
65                  70                  75                  80

Ala Cys Pro Thr Leu Gly Thr Ser Gly Val Gln Tyr Gly Thr Thr Thr

```
                        85                  90                  95
Ile Thr Leu Gln Phe Thr Glu Lys Arg Ser Leu Ile Lys Arg Asn Ile
                100                 105                 110

Asn Leu Ala Gly Asn Lys Lys Pro Ile Trp Glu Asn Gln Ser Cys Asp
            115                 120                 125

Thr Ser Asn Leu Met Val Leu Asn Ser Lys Ser Trp Ser Cys Gly His
130                 135                 140

Tyr Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Tyr Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360

<210> SEQ ID NO 32
<211> LENGTH: 363
<212> TYPE: PRT
<213> ORGANISM: Escherichia coli
<220> FEATURE:
<221> NAME/KEY: MISC_FEATURE
<222> LOCATION: (115)..(128)
<223> OTHER INFORMATION: Epitope

<400> SEQUENCE: 32

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
                20                  25                  30

Phe Gln Ala Pro Arg Leu Asp Arg Ser Val Gln Ser Pro Ile Tyr Asn
            35                  40                  45

Ile Phe Thr Asn His Val Ala Gly Tyr Ser Leu Ser His Arg Leu Tyr
        50                  55                  60

Asp Arg Ile Val Phe Val Cys Thr Ser Ser Ser Asn Pro Val Asn Gly
65                  70                  75                  80
```

```
Ala Cys Pro Thr Ile Gly Thr Ser Arg Val Glu Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Thr Ser Asn Leu Met Val Leu Asn Ser Lys Ser Trp Ser Cys Gly Ala
    130                 135                 140

Leu Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175

Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
        195                 200                 205

Val Trp Leu Pro Gly Phe His Ser Asn Pro Arg Val Asp Leu Asn Leu
    210                 215                 220

His Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
            260                 265                 270

Ile Gly Gly Thr Glu Lys Leu Pro Tyr Ala Val Ser Leu Leu Met Gly
        275                 280                 285

Gly Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
            340                 345                 350

Tyr Ile Thr Phe Thr Pro Ser Val Glu Asn Leu
        355                 360

<210> SEQ ID NO 33
<211> LENGTH: 290
<212> TYPE: PRT
<213> ORGANISM: Escherichia coli
<220> FEATURE:
<221> NAME/KEY: MISC_FEATURE
<222> LOCATION: (222)..(237)
<223> OTHER INFORMATION: Epitope

<400> SEQUENCE: 33

Met Ser His Tyr Lys Thr Gly His Lys Gln Pro Arg Phe Arg Tyr Ser
1               5                   10                  15

Val Leu Ala Arg Cys Val Ala Trp Ala Asn Ile Ser Val Gln Val Leu
            20                  25                  30

Phe Pro Leu Ala Val Thr Phe Thr Pro Val Met Ala Ala Arg Ala Gln
        35                  40                  45

His Ala Val Gln Pro Arg Leu Ser Met Gly Asn Thr Thr Val Thr Ala
    50                  55                  60
```

```
Asp Asn Asn Val Glu Lys Asn Val Ala Ser Phe Ala Ala Asn Ala Gly
 65                  70                  75                  80

Thr Phe Leu Ser Ser Gln Pro Asp Ser Asp Ala Thr Arg Asn Phe Ile
                 85                  90                  95

Thr Gly Met Ala Thr Ala Lys Ala Asn Gln Glu Ile Gln Glu Trp Leu
            100                 105                 110

Gly Lys Tyr Gly Thr Ala Arg Val Lys Leu Asn Val Asp Lys Asp Phe
        115                 120                 125

Ser Leu Lys Asp Ser Ser Leu Glu Met Leu Tyr Pro Ile Tyr Asp Thr
    130                 135                 140

Pro Thr Asn Met Leu Phe Thr Gln Gly Ala Ile His Arg Thr Asp Asp
145                 150                 155                 160

Arg Thr Gln Ser Asn Ile Gly Phe Gly Trp Arg His Phe Ser Gly Asn
                165                 170                 175

Asp Trp Met Ala Gly Val Asn Thr Phe Ile Asp His Asp Leu Ser Arg
            180                 185                 190

Ser His Thr Arg Ile Gly Val Gly Ala Glu Tyr Trp Arg Asp Tyr Leu
        195                 200                 205

Lys Leu Ser Ala Asn Gly Tyr Ile Arg Ala Ser Gly Trp Lys Lys Ser
    210                 215                 220

Pro Asp Ile Glu Asp Tyr Gln Glu Arg Pro Ala Asn Gly Trp Asp Ile
225                 230                 235                 240

Arg Ala Glu Gly Tyr Leu Pro Ala Trp Pro Gln Leu Gly Ala Ser Leu
                245                 250                 255

Met Tyr Glu Gln Tyr Tyr Gly Asp Glu Val Gly Leu Phe Gly Lys Asp
            260                 265                 270

Lys Arg Gln Lys Asp Pro His Ala Ile Ser Ala Glu Val Thr Tyr Thr
        275                 280                 285

Pro Val
    290

<210> SEQ ID NO 34
<211> LENGTH: 42
<212> TYPE: DNA
<213> ORGANISM: Escherichia coli
<220> FEATURE:
<221> NAME/KEY: misc_feature
<222> LOCATION: (9)..(14)
<223> OTHER INFORMATION: Restriction Site

<400> SEQUENCE: 34
atgtagatcg gccgttagct gaaggtgtaa cgacggttca tg                          42

<210> SEQ ID NO 35
<211> LENGTH: 11
<212> TYPE: PRT
<213> ORGANISM: Escherichia coli

<400> SEQUENCE: 35

Asp Ile Gly Arg Leu Gln Ser Asp Ala Glu Tyr
 1               5                  10

<210> SEQ ID NO 36
<211> LENGTH: 10
<212> TYPE: PRT
<213> ORGANISM: Escherichia coli

<400> SEQUENCE: 36

Tyr Asp Ser Asp Pro Lys Leu Asp Ser Gln
```

```
1               5                   10
```

<210> SEQ ID NO 37
<211> LENGTH: 11
<212> TYPE: PRT
<213> ORGANISM: Escherichia coli

<400> SEQUENCE: 37

```
Gln Phe Thr Glu Lys Arg Ser Leu Ile Lys Arg
1               5                   10
```

<210> SEQ ID NO 38
<211> LENGTH: 10
<212> TYPE: PRT
<213> ORGANISM: Escherichia coli

<400> SEQUENCE: 38

```
Tyr Asp Ser Asp Pro Lys Leu Asp Ser Gln
1               5                   10
```

<210> SEQ ID NO 39
<211> LENGTH: 16
<212> TYPE: PRT
<213> ORGANISM: Escherichia coli

<400> SEQUENCE: 39

```
Val Ala Met Lys Asp Ala Tyr Gln Arg Asp Gly Lys Tyr Pro Asp Phe
1               5                   10                  15
```

<210> SEQ ID NO 40
<211> LENGTH: 11
<212> TYPE: PRT
<213> ORGANISM: Escherichia coli

<400> SEQUENCE: 40

```
Val Glu Gly Glu Lys Ser Pro Arg Arg Gly Val
1               5                   10
```

<210> SEQ ID NO 41
<211> LENGTH: 11
<212> TYPE: PRT
<213> ORGANISM: Escherichia coli

<400> SEQUENCE: 41

```
Phe Tyr Leu Arg Lys Ile Asn Asp Asp Thr Lys
1               5                   10
```

<210> SEQ ID NO 42
<211> LENGTH: 13
<212> TYPE: PRT
<213> ORGANISM: Escherichia coli

<400> SEQUENCE: 42

```
Ser Gln Ser Ile Glu Met Arg Phe Gln Asp Asp Ser Gln
1               5                   10
```

<210> SEQ ID NO 43
<211> LENGTH: 14
<212> TYPE: PRT
<213> ORGANISM: Escherichia coli

<400> SEQUENCE: 43

```
Thr Glu Lys Arg Ser Leu Ile Lys Arg Glu Leu Gln Ile Lys
1               5                   10
```

<210> SEQ ID NO 44
<211> LENGTH: 22
<212> TYPE: PRT
<213> ORGANISM: Escherichia coli

<400> SEQUENCE: 44

Gln Asp Asp Asn Ser Lys Ser Asp Gly Lys Phe Tyr Leu Lys Lys Ile
1               5                   10                  15

Asn Asp Asp Ser Lys Glu
            20

<210> SEQ ID NO 45
<211> LENGTH: 13
<212> TYPE: PRT
<213> ORGANISM: Escherichia coli

<400> SEQUENCE: 45

Arg Leu Gln Leu Asp Ala Lys Val Lys Asn Pro Glu Ala
1               5                   10

<210> SEQ ID NO 46
<211> LENGTH: 360
<212> TYPE: PRT
<213> ORGANISM: Escherichia coli
<220> FEATURE:
<221> NAME/KEY: MISC_FEATURE
<222> LOCATION: (105)..(118)
<223> OTHER INFORMATION: Epitope
<220> FEATURE:
<221> NAME/KEY: MISC_FEATURE
<222> LOCATION: (255)..(276)
<223> OTHER INFORMATION: Epitope
<220> FEATURE:
<221> NAME/KEY: MISC_FEATURE
<222> LOCATION: (330)..(342)
<223> OTHER INFORMATION: Epitope

<400> SEQUENCE: 46

Met Asn Lys Ile Leu Phe Ile Phe Thr Leu Phe Phe Ser Ser Gly Phe
1               5                   10                  15

Phe Thr Phe Ala Val Ser Ala Asp Lys Asn Pro Gly Ser Glu Asn Met
            20                  25                  30

Thr Asn Thr Ile Gly Pro His Asp Arg Gly Gly Ser Ser Pro Ile Tyr
        35                  40                  45

Asn Ile Leu Asn Ser Tyr Leu Thr Ala Tyr Asn Gly Ser His His Leu
    50                  55                  60

Tyr Asp Arg Met Ser Phe Leu Cys Leu Ser Ser Gln Asn Thr Leu Asn
65                  70                  75                  80

Gly Ala Cys Pro Ser Ser Asp Ala Pro Gly Thr Ala Thr Ile Asp Gly
                85                  90                  95

Glu Thr Asn Ile Thr Leu Gln Phe Thr Glu Lys Arg Ser Leu Ile Lys
            100                 105                 110

Arg Glu Leu Gln Ile Lys Gly Tyr Lys Gln Phe Leu Phe Lys Asn Ala
        115                 120                 125

Asn Cys Pro Ser Lys Leu Ala Leu Asn Ser Ser His Phe Gln Cys Asn
    130                 135                 140

Arg Glu Gln Ala Ser Gly Ala Thr Leu Ser Leu Tyr Ile Pro Ala Gly
145                 150                 155                 160

Glu Leu Asn Lys Leu Pro Phe Gly Gly Val Trp Asn Ala Val Leu Lys
                165                 170                 175

Leu Asn Val Lys Arg Arg Tyr Asp Thr Thr Tyr Gly Thr Tyr Thr Ile

```
            180                 185                 190
Asn Ile Thr Val Asn Leu Thr Asp Lys Gly Asn Ile Gln Ile Trp Leu
            195                 200                 205

Pro Gln Phe Lys Ser Asn Ala Arg Val Asp Leu Asn Leu Arg Pro Thr
        210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asp Asn Ser Lys Ser Asp Gly Lys Phe Tyr Leu Lys Lys Ile Asn Asp
            260                 265                 270

Asp Ser Lys Glu Leu Val Tyr Thr Leu Ser Leu Leu Ala Gly Lys
        275                 280                 285

Asn Leu Thr Pro Thr Asn Gly Gln Ala Leu Asn Ile Asn Thr Ala Ser
            290                 295                 300

Leu Glu Thr Asn Trp Asn Arg Ile Thr Ala Val Thr Met Pro Glu Ile
305                 310                 315                 320

Ser Val Pro Val Leu Cys Trp Pro Gly Arg Leu Gln Leu Asp Ala Lys
                325                 330                 335

Val Lys Asn Pro Glu Ala Gly Gln Tyr Met Gly Asn Ile Lys Ile Thr
            340                 345                 350

Phe Thr Pro Ser Ser Gln Thr Leu
            355                 360

<210> SEQ ID NO 47
<211> LENGTH: 363
<212> TYPE: PRT
<213> ORGANISM: Escherichia coli
<220> FEATURE:
<221> NAME/KEY: MISC_FEATURE
<222> LOCATION: (100)..(110)
<223> OTHER INFORMATION: Epitope

<400> SEQUENCE: 47

Met Lys Lys Ile Phe Ile Phe Leu Ser Ile Ile Phe Ser Ala Val Val
1               5                   10                  15

Ser Ala Gly Arg Tyr Pro Glu Thr Thr Val Gly Asn Leu Thr Lys Ser
            20                  25                  30

Phe Gln Ala Pro Arg Leu Asp Arg Ser Val Gln Ser Pro Ile Tyr Asn
        35                  40                  45

Ile Phe Thr Asn His Val Ala Gly Tyr Ser Leu Ser His Ser Leu Tyr
    50                  55                  60

Asp Arg Ile Val Phe Leu Cys Thr Ser Ser Asn Pro Val Asn Gly
65                  70                  75                  80

Ala Cys Pro Thr Ile Gly Thr Ser Gly Val Gln Tyr Gly Thr Thr Thr
                85                  90                  95

Ile Thr Leu Gln Phe Thr Glu Lys Arg Ser Leu Ile Lys Arg Asn Ile
            100                 105                 110

Asn Leu Ala Gly Asn Lys Lys Pro Ile Trp Glu Asn Gln Ser Cys Asp
        115                 120                 125

Phe Ser Asn Leu Met Val Leu Asn Ser Lys Ser Trp Ser Cys Gly Ala
    130                 135                 140

His Gly Asn Ala Asn Gly Thr Leu Leu Asn Leu Tyr Ile Pro Ala Gly
145                 150                 155                 160

Glu Ile Asn Lys Leu Pro Phe Gly Gly Ile Trp Glu Ala Thr Leu Ile
                165                 170                 175
```

```
Leu Arg Leu Ser Arg Tyr Gly Glu Val Ser Ser Thr His Tyr Gly Asn
            180                 185                 190

Tyr Thr Val Asn Ile Thr Val Asp Leu Thr Asp Lys Gly Asn Ile Gln
            195                 200                 205

Val Trp Leu Pro Gly Phe His Ser Asn Pro Arg Val Asp Leu Asn Leu
    210                 215                 220

Arg Pro Ile Gly Asn Tyr Lys Tyr Ser Gly Ser Asn Ser Leu Asp Met
225                 230                 235                 240

Cys Phe Tyr Asp Gly Tyr Ser Thr Asn Ser Asp Ser Met Val Ile Lys
                245                 250                 255

Phe Gln Asp Asp Asn Pro Thr Asn Ser Ser Glu Tyr Asn Leu Tyr Lys
                260                 265                 270

Ile Gly Gly Thr Glu Lys Leu Pro Tyr Ala Val Ser Leu Leu Met Gly
            275                 280                 285

Glu Lys Ile Phe Tyr Pro Val Asn Gly Gln Ser Phe Thr Ile Asn Asp
    290                 295                 300

Ser Ser Val Leu Glu Thr Asn Trp Asn Arg Val Thr Ala Val Ala Met
305                 310                 315                 320

Pro Glu Val Asn Val Pro Val Leu Cys Trp Pro Ala Arg Leu Leu Leu
                325                 330                 335

Asn Ala Asp Val Asn Ala Pro Asp Ala Gly Gln Tyr Ser Gly Gln Ile
                340                 345                 350

Tyr Ile Thr Phe Thr Pro Ser Val Glu Asn Leu
            355                 360

<210> SEQ ID NO 48
<211> LENGTH: 364
<212> TYPE: PRT
<213> ORGANISM: Escherichia coli
<220> FEATURE:
<221> NAME/KEY: MISC_FEATURE
<222> LOCATION: (250)..(263)
<223> OTHER INFORMATION: Epitope

<400> SEQUENCE: 48

Met Lys Lys Val Ile Phe Val Leu Ser Met Phe Leu Cys Ser Gln Val
1               5                   10                  15

Tyr Gly Gln Ser Trp His Thr Asn Val Glu Ala Gly Ser Ile Asn Lys
            20                  25                  30

Thr Glu Ser Ile Gly Pro Ile Asp Arg Ser Ala Ala Ser Tyr Pro
            35                  40                  45

Ala His Tyr Ile Phe His Glu His Val Ala Gly Tyr Asn Lys Asp His
    50                  55                  60

Ser Leu Phe Asp Arg Met Thr Phe Leu Cys Met Ser Ser Thr Asp Ala
65                  70                  75                  80

Ser Lys Gly Ala Cys Pro Thr Gly Glu Asn Ser Lys Ser Ser Gln Gly
                85                  90                  95

Glu Thr Asn Ile Lys Leu Ile Phe Thr Glu Lys Lys Ser Leu Ala Arg
            100                 105                 110

Lys Thr Leu Asn Leu Lys Gly Tyr Lys Arg Phe Leu Tyr Glu Ser Asp
            115                 120                 125

Arg Cys Ile His Tyr Val Asp Lys Met Asn Leu Asn Ser His Thr Val
    130                 135                 140

Lys Cys Val Gly Ser Phe Thr Arg Gly Val Asp Phe Thr Leu Tyr Ile
145                 150                 155                 160
```

```
Pro Gln Gly Glu Ile Asp Gly Leu Leu Thr Gly Gly Ile Trp Glu Ala
                165                 170                 175
Thr Leu Glu Leu Arg Val Lys Arg His Tyr Asp Tyr Asn His Gly Thr
            180                 185                 190
Tyr Lys Val Asn Ile Thr Val Asp Leu Thr Asp Lys Gly Asn Ile Gln
        195                 200                 205
Val Trp Thr Pro Lys Phe His Ser Asp Pro Arg Ile Asp Leu Asn Leu
    210                 215                 220
Arg Pro Glu Gly Asn Gly Lys Tyr Ser Gly Ser Asn Val Leu Glu Met
225                 230                 235                 240
Cys Leu Tyr Asp Gly Tyr Ser Thr His Ser Gln Ser Ile Glu Met Arg
                245                 250                 255
Phe Gln Asp Asp Ser Gln Thr Gly Asn Asn Glu Tyr Asn Leu Ile Lys
            260                 265                 270
Thr Gly Glu Pro Leu Lys Lys Leu Pro Tyr Lys Leu Ser Leu Leu Leu
        275                 280                 285
Gly Gly Arg Glu Phe Tyr Pro Asn Asn Gly Glu Ala Phe Thr Ile Asn
    290                 295                 300
Asp Thr Ser Ser Leu Phe Ile Asn Trp Asn Arg Ile Lys Ser Val Ser
305                 310                 315                 320
Leu Pro Gln Ile Ser Ile Pro Val Leu Cys Trp Pro Ala Asn Leu Thr
                325                 330                 335
Phe Met Ser Glu Leu Asn Asn Pro Glu Ala Gly Glu Tyr Ser Gly Ile
            340                 345                 350
Leu Asn Val Thr Phe Thr Pro Ser Ser Ser Ser Leu
        355                 360

<210> SEQ ID NO 49
<211> LENGTH: 168
<212> TYPE: PRT
<213> ORGANISM: Escherichia coli
<220> FEATURE:
<221> NAME/KEY: MISC_FEATURE
<222> LOCATION: (115)..(125)
<223> OTHER INFORMATION: Epitope

<400> SEQUENCE: 49

Met Leu Lys Ile Lys Tyr Leu Leu Ile Gly Leu Ser Leu Ser Ala Met
1               5                   10                  15
Ser Ser Tyr Ser Leu Ala Ala Ala Gly Pro Thr Leu Thr Lys Glu Leu
                20                  25                  30
Ala Leu Asn Val Leu Ser Pro Ala Ala Leu Asp Ala Thr Trp Ala Pro
            35                  40                  45
Gln Asp Asn Leu Thr Leu Ser Asn Thr Gly Val Ser Asn Thr Leu Val
        50                  55                  60
Gly Val Leu Thr Leu Ser Asn Thr Ser Ile Asp Thr Val Ser Ile Ala
65                  70                  75                  80
Ser Thr Asn Val Ser Asp Thr Ser Lys Asn Gly Thr Val Thr Phe Ala
                85                  90                  95
His Glu Thr Asn Asn Ser Ala Ser Phe Ala Thr Thr Ile Ser Thr Asp
            100                 105                 110
Asn Ala Asn Ile Thr Leu Asp Lys Asn Ala Gly Asn Thr Ile Val Lys
        115                 120                 125
Thr Thr Asn Gly Ser Gln Leu Pro Asn Leu Pro Leu Lys Phe Ile
    130                 135                 140
Thr Thr Glu Gly Asn Glu His Leu Val Ser Gly Asn Tyr Arg Ala Asn
```

Ile Thr Ile Thr Ser Thr Ile Lys
            165

<210> SEQ ID NO 50
<211> LENGTH: 361
<212> TYPE: PRT
<213> ORGANISM: Escherichia coli
<220> FEATURE:
<221> NAME/KEY: MISC_FEATURE
<222> LOCATION: (265)..(275)
<223> OTHER INFORMATION: Epitope

<400> SEQUENCE: 50

Met Asn Lys Ile Leu Phe Ile Phe Thr Leu Phe Phe Ser Val Leu
1               5                   10                  15

Phe Thr Phe Ala Val Ser Ala Asp Lys Ile Pro Gly Asp Glu Ser Ile
            20                  25                  30

Thr Asn Ile Phe Gly Pro Arg Asp Arg Asn Glu Ser Ser Pro Lys His
            35                  40                  45

Asn Ile Leu Asn Asn His Ile Thr Ala Tyr Ser Glu Ser His Thr Leu
50                  55                  60

Tyr Asp Arg Met Thr Phe Leu Cys Leu Ser Ser His Asn Thr Leu Asn
65                      70                  75                  80

Gly Ala Cys Pro Thr Ser Glu Asn Pro Ser Ser Ser Val Ser Gly
                    85                  90                  95

Glu Thr Asn Ile Thr Leu Gln Phe Thr Glu Lys Arg Ser Leu Ile Lys
                100                 105                 110

Arg Glu Leu Gln Ile Lys Gly Tyr Lys Gln Leu Leu Phe Lys Ser Val
            115                 120                 125

Asn Cys Pro Ser Gly Leu Thr Leu Asn Ser Ala His Phe Asn Cys Asn
130                 135                 140

Lys Asn Ala Ala Ser Gly Ala Ser Leu Tyr Leu Tyr Ile Pro Ala Gly
145                 150                 155                 160

Glu Leu Lys Asn Leu Pro Phe Gly Gly Ile Trp Asp Ala Thr Leu Lys
                165                 170                 175

Leu Arg Val Lys Arg Arg Tyr Ser Glu Thr Tyr Gly Thr Tyr Thr Ile
            180                 185                 190

Asn Ile Thr Ile Lys Leu Thr Asp Lys Gly Asn Ile Gln Ile Trp Leu
            195                 200                 205

Pro Gln Phe Lys Ser Asp Ala Arg Val Asp Leu Asn Leu Arg Pro Thr
210                 215                 220

Gly Gly Gly Thr Tyr Ile Gly Arg Asn Ser Val Asp Met Cys Phe Tyr
225                 230                 235                 240

Asp Gly Tyr Ser Thr Asn Ser Ser Leu Glu Ile Arg Phe Gln Asp
                245                 250                 255

Asn Asn Pro Lys Ser Asp Gly Lys Phe Tyr Leu Arg Lys Ile Asn Asp
            260                 265                 270

Asp Thr Lys Glu Ile Ala Tyr Thr Leu Ser Leu Leu Ala Gly Lys
            275                 280                 285

Ser Leu Thr Pro Thr Asn Gly Thr Ser Leu Asn Ile Ala Asp Ala Ala
290                 295                 300

Ser Leu Glu Thr Asn Trp Asn Arg Ile Thr Ala Val Thr Met Pro Glu
305                 310                 315                 320

Ile Ser Val Pro Val Leu Cys Trp Pro Gly Arg Leu Gln Leu Asp Ala
            325                 330                 335

-continued

```
Lys Val Glu Asn Pro Glu Ala Gly Gln Tyr Met Gly Asn Ile Asn Val
            340                 345                 350

Thr Phe Thr Pro Ser Ser Gln Thr Leu
            355                 360

<210> SEQ ID NO 51
<211> LENGTH: 373
<212> TYPE: PRT
<213> ORGANISM: Escherichia coli
<220> FEATURE:
<221> NAME/KEY: MISC_FEATURE
<222> LOCATION: (185)..(195)
<223> OTHER INFORMATION: Epitope

<400> SEQUENCE: 51

Met Lys Lys Gln Pro Ile Val Leu Thr Leu Gly Phe Phe Ser Phe Met
1               5                   10                  15

Val Gln Ala Ala Thr Thr Val Thr Ser Glu Phe Glu Ile Thr Asn Lys
            20                  25                  30

Thr Ile Glu Lys Tyr Thr Ile Ser Ser Thr Asp Ser Thr Met Thr Tyr
        35                  40                  45

Thr Asp Val Ser Gly Ser Gly Leu Tyr Lys Ile Ser Asp Gln Tyr Ser
    50                  55                  60

Asp Ala Asn Val Asn Ile Arg Asn Tyr Gly Asn His Gln Phe Gly Leu
65                  70                  75                  80

Leu Arg Asn Asn Ser Thr Val Asn Ile Ile Met Lys Gly Val Asn Leu
                85                  90                  95

Gly His Thr Phe Thr Val Gln Gly Lys Tyr Ala Asn Ser Ala Val Ser
            100                 105                 110

Val Pro Asn Pro Gln Lys Tyr Phe Thr Val Arg Ser Asn Asn Gly Cys
        115                 120                 125

Ser Ser Val Ser Ser Ala Tyr Leu Gly Asn Ala Ser Tyr Thr Leu Tyr
    130                 135                 140

Glu Ile Arg Ser Ser Asn Asp Val Thr Arg Asn Cys Ser Gly Gln Thr
145                 150                 155                 160

Asp Gln Tyr Thr His Met Pro Asn Asn Ser Gly Gln Val Asn Val Thr
                165                 170                 175

Gly Ile Tyr Arg Asp Phe Tyr Leu Asp Ile Gly Arg Leu Gln Ser Asp
            180                 185                 190

Ala Glu Tyr Arg Lys Ala Pro Pro Asp Thr Tyr Ile Gly Thr Gly Thr
        195                 200                 205

Phe Ala Gly Glu Val Leu Lys Asn Arg Val Gly Ser Gly Tyr Thr Pro
    210                 215                 220

Thr Tyr Thr Asn Lys Ile Thr Ile Thr Lys Lys Pro Tyr Phe Glu Ser
225                 230                 235                 240

Val Thr Leu Pro Thr Val Asp Asn Ile Phe Asp Thr Arg Thr Ile Gly
                245                 250                 255

Arg Gln Ile Gln Gly Asn Leu Val Ile Pro Phe Val Ile Asn Gly His
            260                 265                 270

Phe Thr Pro Tyr Asn Thr Ile Ser Leu Gln Val Ile Ser Leu Asn Gly
        275                 280                 285

Phe Lys Leu Gln Ser Glu Asn Val Gly Ser Ser Ala Thr Ile Pro Tyr
    290                 295                 300

Ser Leu Asn Met Thr Ile Gly Ser Glu Arg Arg Tyr Ser Leu Ala Thr
305                 310                 315                 320
```

```
Asn Gly Asn Gly Leu Gly Asn Val Thr Ile Asn Asn Leu Glu Ser Asp
            325                 330                 335

Gly Tyr Ser Ile Gln Gly Arg Phe Asn Ala Asp Phe Leu Ile Asp Lys
            340                 345                 350

Asn Thr Ala Val Thr Gly Asp Tyr Ala Asp Thr Leu Thr Ala Ile Phe
            355                 360                 365

Gln Ile Ser Leu Leu
            370

<210> SEQ ID NO 52
<211> LENGTH: 167
<212> TYPE: PRT
<213> ORGANISM: Escherichia coli
<220> FEATURE:
<221> NAME/KEY: MISC_FEATURE
<222> LOCATION: (53)..(63)
<223> OTHER INFORMATION: Epitope

<400> SEQUENCE: 52

Met Leu Lys Lys Ile Ile Ser Ala Ile Ala Leu Ile Ala Gly Thr Ser
1               5                   10                  15

Gly Val Val Asn Ala Gly Asn Trp Gln Tyr Lys Ser Leu Asp Val Asn
            20                  25                  30

Val Lys Ile Glu Gln Asn Phe Ile Pro Asp Ile Asp Ser Ala Val Arg
        35                  40                  45

Ile Ile Pro Val Asn Tyr Asp Ser Asp Pro Lys Leu Asp Ser Gln Leu
    50                  55                  60

Tyr Thr Val Glu Met Thr Ile Pro Ala Gly Val Ser Ala Val Lys Ile
65                  70                  75                  80

Ala Pro Thr Asp Ser Leu Thr Ser Ser Gly Gln Gln Ile Gly Lys Leu
                85                  90                  95

Val Asn Val Asn Asn Pro Asp Gln Asn Met Asn Tyr Tyr Ile Arg Lys
            100                 105                 110

Asp Ser Gly Ala Gly Asn Phe Met Ala Gly Gln Lys Gly Ser Phe Pro
        115                 120                 125

Val Lys Glu Asn Thr Ser Tyr Thr Phe Ser Ala Ile Tyr Thr Gly Gly
    130                 135                 140

Glu Tyr Pro Asn Ser Gly Tyr Ser Ser Gly Thr Tyr Ala Gly Asn Leu
145                 150                 155                 160

Thr Val Ser Phe Tyr Ser Asn
                165

<210> SEQ ID NO 53
<211> LENGTH: 206
<212> TYPE: PRT
<213> ORGANISM: Escherichia coli
<220> FEATURE:
<221> NAME/KEY: MISC_FEATURE
<222> LOCATION: (45)..(60)
<223> OTHER INFORMATION: Epitope

<400> SEQUENCE: 53

Met Ser Leu Leu Glu Val Ile Ile Val Leu Gly Ile Ile Gly Thr Ile
1               5                   10                  15

Ala Ala Gly Val Val Ile Leu Ala Gln Arg Ala Phe Asp Ser Arg Ala
            20                  25                  30

Val Thr Asp Leu Val Thr Asn Thr Asn Thr Val Arg Val Ala Met Lys
        35                  40                  45

Asp Ala Tyr Gln Arg Asp Gly Lys Tyr Pro Asp Phe Val Asp Pro Leu
```

```
            50                  55                  60
Ser Leu Thr Ala Asn Thr Ile Lys Thr Asp Thr Ser Gly Ile Pro Ala
 65                  70                  75                  80

Ala Gln Leu Val Gln Leu Gly Lys Ile Thr Pro Asp Glu Val Arg Asn
                 85                  90                  95

Asn Ile Ser Gly Asp Phe Ile Ala Ile Gly Ala Leu Thr Ser Asn
            100                 105                 110

Gly Ala Gln Val Lys Lys Gly Phe Ala Ile Glu Leu Asn Gly Leu Ser
            115                 120                 125

Gln Glu Gln Cys Arg Ser Ile Leu Gly Gln Val Gly Asn Asn Trp Glu
            130                 135                 140

Tyr Val Ala Ile Gly Thr Ser Ala Ser Gly Ser Tyr Ala Met Thr Ala
145                 150                 155                 160

Thr Gly Val Asp Met Ser Val Ala Ala Ser Thr Thr Val Leu Arg Ser
                165                 170                 175

Leu Gly Asn Gly Gly Gln Thr Thr Leu Thr Ala Asp Lys Ile Leu Ser
            180                 185                 190

Thr Cys Thr Ala Gln Val Asn Ser Ile Thr Leu Gly Ser Arg
            195                 200                 205

<210> SEQ ID NO 54
<211> LENGTH: 7
<212> TYPE: PRT
<213> ORGANISM: Escherichia coli

<400> SEQUENCE: 54

Gln Val Thr Val Tyr Pro Val
1               5

<210> SEQ ID NO 55
<211> LENGTH: 1035
<212> TYPE: DNA
<213> ORGANISM: Escherichia coli

<400> SEQUENCE: 55
gggcgatacc cggaaactac agtaggtaat ctgacgaaga gttttcaagc ccctcgtctg      60
gatagaagcg tacaatcacc aatatataac atctttacga atcatgtggc tggatatagt     120
ttgagtcata gcttatatga caggattgtt tttttatgta catcctcgtc gaatccggtt     180
aatggtgctt gcccaaccat tggaacatct ggagttcaat acggtactac aaccataacc     240
ttgcagttta cagaaaaaag aagtctgata aaagaaata ttaatcttgc aggtaataag      300
aaaccaatat gggagaatca gagttgcgac tttagcaatc taatggtgtt gaattcgaag     360
tcttggagct gtggggctca cggaaatgct aacggaacac ttctaaatct gtatatccct     420
gcaggagaaa tcaacaaatt gccttttgga gggatatggg aggcaactct gatcttacgc     480
ttatcaagat atggcgaagt cagtagcacc cattacggca attataccgt aaatattacg     540
gttgatttaa ctgataaagg taatattcag gtatggcttc agggtttca cagcaacccg      600 cgtgtagacc tgaatctgcg ccctatcggt aattataaat atagtggtag taattcactc     660
gacatgtgtt tctatgatgg atatagtaca aacagtgata gcatggtaat aaagttccag     720
gatgataatc ctaccaattc atctgaatat aatctttata agatagggg cactgaaaaa       780 ttaccatatg ctgtttcact gcttatggga gaaaaatat tttatccagt gaatggtcaa       840
tcatttacta tcaatgacag tagtgtactc gaaacaaact ggaatcgagt aaccgcagtt     900
gctatgccgg aagttaatgt tccagtatta tgctggccag caagattgct attaaatgct     960
```

```
gatgtaaatg ctcccgatgc aggacagtat tcaggacaga tatatataac atttacaccc    1020
agtgtcgaaa attta                                                     1035

<210> SEQ ID NO 56
<211> LENGTH: 1043
<212> TYPE: DNA
<213> ORGANISM: Escherichia coli

<400> SEQUENCE: 56
caatcatggc atacgaacgt agaggctggt tcaataaata aaacagagtc gataggcccc     60
atagaccgaa gtgctgctgc atcgtatcct gctcattata tatttcatga acatgttgct    120
ggttacaata aagatcactc tcttttgac aggatgacgt ttttatgtat gtcatcaaca     180
gatgcatcta aaggtgcatg tccgacagga gaaaactcca atcctctca aggggagact     240 aatattaagc taatatttac tgaaaagaaa agtctggcca gaaaaacatt aaacttaaaa    300
ggatataaga gattttttata tgaatcagat agatgcattc attatgtcga taaaatgaat    360
ctcaattctc atactgttaa atgtgtaggt tcattcacaa gaggagtaga tttcacttta    420
tatatcccac aaggtgaaat tgatgggctt ctaactggag gtatatggga ggcaacacta    480
gagttacgag tcaaaaggca ttacgactat aatcatggta cttacaaagt aatatcaca    540 gttgatttga cagacaaagg aaatattcag gtctggacac caaagtttca tagcgatcct    600
agaattgatc tgaatttacg tcctgaaggt aatggtaaat attctggtag taacgtgctt    660
gagatgtgtc tctatgatgg ctatagtaca catagtcaaa gtatagaaat gaggtttcag    720
gatgactcac aaacaggaaa taatgaatat aatcttataa aaactggaga gccattaaaa    780
aaattgccat ataaactttc tcttctttta ggaggacgag agtttatcc aaataatgga    840 gaggctttta ctattaatga tacttcgtca ttgtttataa actggaatcg tattaagtct    900
gtatccttac cacagattag tattccagta ctatgctggc cagcaaactt gacatttatg    960
tcagagctaa ataatccaga gcgggtgag tattcaggaa tacttaacgt aacatttact    1020
cctagtagtt caagtctgta acg                                           1043

<210> SEQ ID NO 57
<211> LENGTH: 405
<212> TYPE: DNA
<213> ORGANISM: Escherichia coli

<400> SEQUENCE: 57
atgggcactc taaccaaaga actggcatta aatgtgcttt ctcctgcagc tctggatgca     60
gcttgggctc ctcaggataa tttaacatta tccaatactg gcgtttctaa tactttggtg    120
ggtgttttga ctctttcaaa taccagtatt gatacagtta gcattgcgag tacaaatgtt    180
tctgatacat ctaagaatgg tacagtaact tttgcacatg agacaaataa ctctgctagc    240
tttgccacca ccatttcaac agataatgcc aacattacgt tggataaaaa tgctggaaat    300
acgattgtta aaactacaaa tgggagtcag ttgccaacta atttaccact taagtttatt    360
accactgaag gtaacgaaca tttagtttca ggtaattaac ggccg                   405

<210> SEQ ID NO 58
<211> LENGTH: 1023
<212> TYPE: DNA
<213> ORGANISM: Escherichia coli
<220> FEATURE:
<221> NAME/KEY: misc_feature
<222> LOCATION: (331)..(331)
```

<223> OTHER INFORMATION: n is a, c, g, or t

<400> SEQUENCE: 58

```
gataaaattc ccggagatga aagcataact aatattttg gcccgcgtga caggaacgaa      60
tcttccccca aacataatat attaaataac catattacag catacagtga aagtcatact    120
ctgtatgata ggatgacttt tttatgtttg tcttctcaca atacacttaa tggagcatgt    180
ccaaccagtg agaatcctag cagttcatcg gtcagcggtg aaacaaatat aacattacaa    240
tttacggaaa aagaagttt aataaaaaga gagctacaaa ttaaaggcta taaacaatta    300
ttgttcaaaa gtgttaactg cccatccggc ntaacactta actcagctca ttttaactgt    360
aataaaaacg cggcttcagg tgcaagttta tatttatata ttcctgctgg cgaactaaaa    420
aatttgcctt ttggtggtat ctgggatgct actctgaagt taagagtaaa aagacgatat    480
agtgagacct atggaactta cactataaat atcactatta aattaactga taagggaaat    540
attcagatat ggttacctca gttcaaaagt gacgctcgcg tcgatcttaa cttgcgtcca    600
actggtgggg gcacatatat tggaagaaat tctgttgata tgtgcttta tgatggatat    660
agtactaaca gcagctcttt ggagataaga tttcaggata acaatcctaa atctgatggg    720
aaatttatc taaggaaaat aaatgatgac accaaagaaa ttgcatatac tttgtcactt    780
ctcttggcgg gtaaaagttt aactccaaca aatggaacgt cattaaatat tgctgacgca    840
gcttctctgg aaacaaactg gaatagaatt acagctgtca ccatgccaga aatcagtgtt    900
ccggtgttgt gttggcctgg acgtttgcaa ttggatgcaa aagtggaaaa tcccgaggct    960
ggacaatata tgggtaatat taatgttact ttcacaccaa gtagtcaaac actctagcgg   1020
ccg                                                                  1023
```

<210> SEQ ID NO 59
<211> LENGTH: 962
<212> TYPE: DNA
<213> ORGANISM: Escherichia coli

<400> SEQUENCE: 59

```
atggttatgg ttcaggctgc tacaacagtt acttcagaat ttgaaattac taataaaact     60
atcgaaaaat atacaatatc aagtacagat agtactatga catatactga tgtatcaggg    120
agtggtttat ataaaatatc agaccagtat tcagatgcca atgtcaatat tagaaattac    180
ggcaatcatc agtttggatt gctcagaaat aacagcactg ttaatattat catgaagggc    240
gtaaacttag gccacacttt tactgtacaa ggaaaatatg ccaattcagc cgtgtcagtt    300
cccaatcctc aaaaatattt taccgttaga agtaataatg gatgctcaag tgtatcttct    360
gcatatctag gtaatgcgag ttatacgcta tacgaaataa gatctagtaa tgatgttaca    420
cggaactgtt ccggacaaac ggatcagtac actcatatgc caaataatag tggtcaggta    480
aatgttacag gaatttacag agatttctac ttggatattg gtcgactgca atcgacgct    540
gagtatagga aagcacctcc tgataccttat ataggaacag ggacattcgc tggagaggtt    600
ttaaagaatc gagtaggttc tggttatact ccgacttata caaacaaaat aacaattaca    660
aaaaaaccat attttgaaag tgtgacattg cccacggtag ataatatctt cgatactcgt    720
actatcggca gacagattca ggggaatctt gtaattccat ttgtgattaa tgggcatttc    780
acaccataca atactatttc gttgcaggtc atttcactaa atgggtttaa gttacaaagt    840
gagaatgttg gttcctcagc aaccattcct tattcgctaa atatgacgat aggtagtgaa    900
cgacgttatt ccttggccac aaatgggaat ggtttgggaa atgttacaat aaataacggc    960
```

| cg | 962 |

<210> SEQ ID NO 60
<211> LENGTH: 393
<212> TYPE: DNA
<213> ORGANISM: Escherichia coli

<400> SEQUENCE: 60

| aatattgagc aaaattttat tccagatatt gattccgctg ttcgtataat acctgttaat | 60 |
| tacgattcgg atccgaaact gaattcacag ttatatacgg ttgagatgac gatccctgca | 120 |
| ggtgtaagcg cagttaaaat cgtaccaaca gatagtctga catcttctgg acagcagatc | 180 |
| ggaaagctgg ttaatgtaaa caatccagat caaaatatga attattatat cagaaaggat | 240 |
| tctggcgctg gtaagtttat ggcagggcaa aaaggctcct tttctgtcaa agagaatacg | 300 |
| tcatacacat tctcagcaat ttatactggt ggcgaatacc ctaatagcgg atattcgtct | 360 |
| ggtacttatg caggaaattt gacttaacgg ccg | 393 |

<210> SEQ ID NO 61
<211> LENGTH: 630
<212> TYPE: DNA
<213> ORGANISM: Escherichia coli
<220> FEATURE:
<221> NAME/KEY: misc_feature
<222> LOCATION: (600)..(600)
<223> OTHER INFORMATION: n is a, c, g, or t

<400> SEQUENCE: 61

| atggctagca tgagcctgct ggaagttatc attgttcttg cattatcgg tacgattgca | 60 |
| gccggtgtcg tgattctggc tcagcgtgcg tttgattcac gtgctgtgac tgatttagta | 120 |
| actaatacaa atacagtccg cgtagcaatg aaagatgctt atcaacgtga tggtaaatat | 180 |
| ccagattttg tggacccatt aagccttact gcaaatacaa ttaaaactga tacaagcgga | 240 |
| atacctgcag cacagttagt tcagcttggg aaaattacac cagacgaagt gcgtaataac | 300 |
| atttctggcg actttatcgc tattggcggt gctttaactt cgaatggtgc tcaagttaaa | 360 |
| aaaggttttg ctatcgaact taatggatta agccaagagc agtgccgttc tattcttggg | 420 |
| caagttggga ataactggga atatgttgct attggtactt ctgcgtctgg ttcatatgcc | 480 |
| atgacagcaa ctggtgtaga tatgtctgtg gccgcctcta caactgtttt acgctctta | 540 |
| ggtaacggtg gacaaacaac cttgactgca gacaaaattc taagtacctg tactgctcan | 600 |
| gtaaactcaa ttactttagg tagccgttaa | 630 |

<210> SEQ ID NO 62
<211> LENGTH: 480
<212> TYPE: DNA
<213> ORGANISM: Escherichia coli

<400> SEQUENCE: 62

| atggcaaaag ccacgggcag cgtggagggc gaaaagtccc ccgtcgtgg cgtgcgcgcc | 60 |
| atggcgctga gcctgctgtc gggtatgatg ataatggccc atccggcgat gtcagcaaac | 120 |
| ctgccgaccg gtggccagat tgtggcaggt tcaggcagta tccagacgcc ttccggcaac | 180 |
| cagatgaata ttcatcagaa cagccagaac atggtggcca actggaacag ctttgacatt | 240 |
| ggtaaaggaa atacggtgca gttttaccag cccagcagca gtgcagtggc gctgaaccgt | 300 |
| gttgtgggtg gcggtgaatc gcagattatg ggtaacctga aggcgaatgg tcaggtgttc | 360 |

```
ctggttaacc cgaacggcgt gctgtttggt aagggtgcca gtgtcagcac gtcaggtttt    420
gtggcatcga cccgcgacat taaaaacgac gacttcatga accgtcgtta caccttcagc    480
```

<210> SEQ ID NO 63
<211> LENGTH: 1161
<212> TYPE: DNA
<213> ORGANISM: Escherichia coli

<400> SEQUENCE: 63

```
atgaataaga ttttatttat ttttacattg tttttctctt cagtactttt tacatttgct     60
gtatcggcac aagaaggtag tagcaaccgg gcaaagattg accagacagg agattatact    120 aatattttg gcccgcgtga caggaacgaa tcttccccca acataatat attaaatgac     180 tatattacag catacagtga aagtcatact ctgtatgata ggatgatttt tttatgtttg    240
tcttctcaaa atacacttaa tggagcatgt ccaaccagtg agaatcctag cagttcatcg    300
gtcagtggcg aaacaaatat aacattcaa tttacggaaa aagaagttt aattaaaaga     360 gagctacaaa ttaaaggcta taaacgatta ttgttcaaag gtgctaactg cccatcctac    420
ctaacactta actcagctca ttataataaa gacggagagg gagtttcacc tgggggtgca    480
agtttatatt tatatattcc tgctggcgaa ctaaaaaatt taccttttgg tggtatctgg    540
gatgctactc tgaagttaag agtaaaaaga cgatatgatc agacctatgg aacttacact    600
ataaatatca ctgttaaatt aactgataag ggaaatattc agatatggtt acctcagttc    660
aaaagtgacg ctcgcgtcga tcttaacttg agttttcaag cccctcgtca ggatagaagc    720
gtacaatcag gaagaaattc tgttgatatg tgcttttatg atggatatag tactaacagc    780
agctctttgg agctaagatt tcaggataac aatcctaaat ctgatgggaa attttatcta    840
aggaaaataa atgatgacac caaagaaatt gcatatactt tgtcacttct cttggcgggt    900
aaaagtgcag gtaataagaa accaatatgg gagaatcaga gttgcgacaa tattgctgac    960
gcagcttctc tggaaataaa ctggaataga attcagctg tcaccatgcc agaaatcagt   1020
gttccggtgt tgtgttggcc tggacgtttg caattggatg caaaaaaatc gccggatatt   1080
gaggattatc aggaacgccc ggcgaatggc tatatgggta atattaatat tactttcaca   1140
ccaagtagtc aaacactcta g                                             1161
```

<210> SEQ ID NO 64
<211> LENGTH: 386
<212> TYPE: PRT
<213> ORGANISM: Escherichia coli

<400> SEQUENCE: 64

```
Met Asn Lys Ile Leu Phe Ile Phe Thr Leu Phe Phe Ser Ser Val Leu
1               5                   10                  15

Phe Thr Phe Ala Val Ser Ala Gln Glu Gly Ser Ser Asn Arg Ala Lys
            20                  25                  30

Ile Asp Gln Thr Gly Asp Tyr Thr Asn Ile Phe Gly Pro Arg Asp Arg
        35                  40                  45

Asn Glu Ser Ser Pro Lys His Asn Ile Leu Asn Asp Tyr Ile Thr Ala
    50                  55                  60

Tyr Ser Glu Ser His Thr Leu Tyr Asp Arg Met Ile Phe Leu Cys Leu
65                  70                  75                  80

Ser Ser Gln Asn Thr Leu Asn Gly Ala Cys Pro Thr Ser Glu Asn Pro
                85                  90                  95

Ser Ser Ser Ser Val Ser Gly Glu Thr Asn Ile Thr Leu Gln Phe Thr
```

```
            100                 105                 110
Glu Lys Arg Ser Leu Ile Lys Arg Glu Leu Gln Ile Lys Gly Tyr Lys
            115                 120                 125

Arg Leu Leu Phe Lys Gly Ala Asn Cys Pro Ser Tyr Leu Thr Leu Asn
    130                 135                 140

Ser Ala His Tyr Asn Lys Asp Gly Glu Gly Val Ser Pro Gly Gly Ala
145                 150                 155                 160

Ser Leu Tyr Leu Tyr Ile Pro Ala Gly Glu Leu Lys Asn Leu Pro Phe
                165                 170                 175

Gly Gly Ile Trp Asp Ala Thr Leu Lys Leu Arg Val Lys Arg Arg Tyr
            180                 185                 190

Asp Gln Thr Tyr Gly Thr Tyr Thr Ile Asn Ile Thr Val Lys Leu Thr
        195                 200                 205

Asp Lys Gly Asn Ile Gln Ile Trp Leu Pro Gln Phe Lys Ser Asp Ala
    210                 215                 220

Arg Val Asp Leu Asn Leu Ser Phe Gln Ala Pro Arg Gln Asp Arg Ser
225                 230                 235                 240

Val Gln Ser Gly Arg Asn Ser Val Asp Met Cys Phe Tyr Asp Gly Tyr
                245                 250                 255

Ser Thr Asn Ser Ser Leu Glu Leu Arg Phe Gln Asp Asn Asn Pro
            260                 265                 270

Lys Ser Asp Gly Lys Phe Tyr Leu Arg Lys Ile Asn Asp Asp Thr Lys
        275                 280                 285

Glu Ile Ala Tyr Thr Leu Ser Leu Leu Ala Gly Lys Ser Ala Gly
    290                 295                 300

Asn Lys Lys Pro Ile Trp Glu Asn Gln Ser Cys Asp Asn Ile Ala Asp
305                 310                 315                 320

Ala Ala Ser Leu Glu Ile Asn Trp Asn Arg Ile Thr Ala Val Thr Met
                325                 330                 335

Pro Glu Ile Ser Val Pro Val Leu Cys Trp Pro Gly Arg Leu Gln Leu
            340                 345                 350

Asp Ala Lys Lys Ser Pro Asp Ile Glu Asp Tyr Gln Glu Arg Pro Ala
        355                 360                 365

Asn Gly Tyr Met Gly Asn Ile Asn Ile Thr Phe Thr Pro Ser Ser Gln
    370                 375                 380

Thr Leu
385

<210> SEQ ID NO 65
<211> LENGTH: 1161
<212> TYPE: DNA
<213> ORGANISM: Escherichia coli

<400> SEQUENCE: 65
atgaataaga ttttatttat ttttacattg ttttttctctt cagtactttt tacatttgct    60
gtatcggcac aagaaggtag tagcaaccgg gcaaagattg accagacagg agattatact   120 aatattttg gcccgcgtga caggaacgaa tcttcccca acataatat attaaatgac     180 tatattacag catacagtga aagtcatact ctgtatgata ggatgatttt tttatgtttg   240
tcttctcaaa atacacttaa tggagcatgt ccaaccagtg agaatcctag cagttcatcg   300
gtcagtggcg aaacaaatat aacattacaa tttacggaaa aagaagtttt aattaaaga    360 gagctacaaa ttaaaggcta taacgatta ttgttcaaag gtgctaactg cccatcctac   420
ctaacactta actcagctca ttataataaa gacggagagg gagttttacc tgggggtgca   480
```

```
agtttatatt tatatattcc tgctggcgaa ctaaaaaatt tacctttggg tggtatctgg    540
gatgctactc tgaagttaag agtaaaaaga cgatatgatc agacctatgg aacttacact    600
ataaatatca ctgttaaatt aactgataag ggaaatattc agatatggtt acctcagttc    660
aaaagtgacg ctcgcgtcga tcttaacttg agttttcaag cccctcgtca ggatagaagc    720
gtacaatcag gaagaaattc tgttgatatg tgcttttatg atggatatag tactaacagc    780
agctctttgg agctaagatt tcaggataac aatcctaaat ctgatgggaa attttatcta    840
aggaaaataa atgatgacac caaagaaatt gcatatactt tgtcacttct cttggcgggt    900
aaaagtgcag gtaataagaa accaatatgg gagaatcaga gttgcgacaa tattgctgac    960
gcagcttctc tggaaataaa ctggaataga attacagctg tcaccatgcc agaaatcagt   1020
gttccggtgt tgtgttggcc tggacgtttg caattggatg caaaaaaatc gccggatatt   1080
gaggattatc aggaacgccc ggcgaatggc tatatgggta atattaatat tactttcaca   1140
ccaagtagtc aaacactcta g                                             1161
```

<210> SEQ ID NO 66
<211> LENGTH: 386
<212> TYPE: PRT
<213> ORGANISM: Escherichia coli

<400> SEQUENCE: 66

```
Met Asn Lys Ile Leu Phe Ile Phe Thr Leu Phe Ser Ser Val Leu
1               5                   10                  15

Phe Thr Phe Ala Val Ser Ala Gln Glu Gly Ser Ser Asn Arg Ala Lys
            20                  25                  30

Ile Asp Gln Thr Gly Asp Tyr Thr Asn Ile Phe Gly Pro Arg Asp Arg
        35                  40                  45

Asn Glu Ser Ser Pro Lys His Asn Ile Leu Asn Asp Tyr Ile Thr Ala
    50                  55                  60

Tyr Ser Glu Ser His Thr Leu Tyr Asp Arg Met Ile Phe Leu Cys Leu
65                  70                  75                  80

Ser Ser Gln Asn Thr Leu Asn Gly Ala Cys Pro Thr Ser Glu Asn Pro
                85                  90                  95

Ser Ser Ser Ser Val Ser Gly Glu Thr Asn Ile Thr Leu Gln Phe Thr
            100                 105                 110

Glu Lys Arg Ser Leu Ile Lys Arg Glu Leu Gln Ile Lys Gly Tyr Lys
        115                 120                 125

Arg Leu Leu Phe Lys Gly Ala Asn Cys Pro Ser Tyr Leu Thr Leu Asn
    130                 135                 140

Ser Ala His Tyr Asn Lys Asp Gly Glu Gly Val Ser Pro Gly Gly Ala
145                 150                 155                 160

Ser Leu Tyr Leu Tyr Ile Pro Ala Gly Glu Leu Lys Asn Leu Pro Phe
                165                 170                 175

Gly Gly Ile Trp Asp Ala Thr Leu Lys Leu Arg Val Lys Arg Arg Tyr
            180                 185                 190

Asp Gln Thr Tyr Gly Thr Tyr Thr Ile Asn Ile Thr Val Lys Leu Thr
        195                 200                 205

Asp Lys Gly Asn Ile Gln Ile Trp Leu Pro Gln Phe Lys Ser Asp Ala
    210                 215                 220

Arg Val Asp Leu Asn Leu Ser Phe Gln Ala Pro Arg Gln Asp Arg Ser
225                 230                 235                 240

Val Gln Ser Gly Arg Asn Ser Val Asp Met Cys Phe Tyr Asp Gly Tyr
```

```
            245                 250                 255
Ser Thr Asn Ser Ser Leu Glu Leu Arg Phe Gln Asp Asn Asn Pro
        260                 265                 270

Lys Ser Asp Gly Lys Phe Tyr Leu Arg Lys Ile Asn Asp Thr Lys
        275                 280                 285

Glu Ile Ala Tyr Thr Leu Ser Leu Leu Leu Ala Gly Lys Ser Ala Gly
        290                 295                 300

Asn Lys Lys Pro Ile Trp Glu Asn Gln Ser Cys Asp Asn Ile Ala Asp
305                 310                 315                 320

Ala Ala Ser Leu Glu Ile Asn Trp Asn Arg Ile Thr Ala Val Thr Met
                325                 330                 335

Pro Glu Ile Ser Val Pro Val Leu Cys Trp Pro Gly Arg Leu Gln Leu
                340                 345                 350

Asp Ala Lys Lys Ser Pro Asp Ile Glu Asp Tyr Gln Glu Arg Pro Ala
                355                 360                 365

Asn Gly Tyr Met Gly Asn Ile Asn Ile Thr Phe Thr Pro Ser Ser Gln
                370                 375                 380

Thr Leu
385

<210> SEQ ID NO 67
<211> LENGTH: 242
<212> TYPE: PRT
<213> ORGANISM: Escherichia coli

<400> SEQUENCE: 67

Met Ser Leu Leu Glu Val Ile Ile Val Leu Gly Ile Ile Gly Thr Ile
1               5                   10                  15

Ala Ala Gly Val Val Ile Leu Ala Gln Arg Ala Phe Asp Ser Arg Ala
                20                  25                  30

Val Thr Asp Leu Glu Ala Ala Pro Pro Glu Ala Gly Asn Tyr Thr Val
                35                  40                  45

Arg Val Ala Met Lys Asp Ala Tyr Gln Arg Asp Gly Lys Tyr Pro Asp
        50                  55                  60

Phe Val Asp Pro Leu Ser Leu Thr Ala Asn Thr Ile Lys Thr Asp Thr
65                  70                  75                  80

Ser Gly Ile Pro Ala Ala Gln Leu Val Gln Leu Gly Lys Ala Asp Thr
                85                  90                  95

Gln Gly Thr Ala Pro Glu Ala Gly Asn Tyr Ile Ser Gly Asp Phe Ile
                100                 105                 110

Ala Ile Gly Gly Ala Val Glu Gly Glu Lys Ser Pro Arg Arg Gly Val
            115                 120                 125

Lys Lys Gly Phe Ala Ile Glu Leu Asn Gly Leu Thr Ser Gly Thr Ala
        130                 135                 140

Pro Ser Ala Gly Lys Tyr Gln Glu Gln Cys Arg Ser Ile Leu Gly Gln
145                 150                 155                 160

Val Gly Ala Gly Ser Pro Val Thr Arg Ser Asp Thr Thr Ser Trp Glu
                165                 170                 175

Tyr Val Ala Gly Ser Asn Gly Gln Ala Asn Asn Asn Asp Ala Ser Gln
                180                 185                 190

Val Asp Met Ser Val Ala Ala Ser Thr Thr Val Leu Arg Ser Leu Gly
            195                 200                 205

Asn Lys Lys Ser Pro Asp Ile Glu Asp Tyr Gln Glu Arg Thr Ala Asp
        210                 215                 220
```

Lys Ile Leu Ser Thr Cys Thr Ala Gln Val Asn Ser Ile Thr Leu Gly
225                 230                 235                 240

Ser Arg

<210> SEQ ID NO 68
<211> LENGTH: 12
<212> TYPE: PRT
<213> ORGANISM: Escherichia coli

<400> SEQUENCE: 68

Ala Gly Ser Pro Val Thr Arg Ser Asp Thr Thr Ser
1               5                   10

<210> SEQ ID NO 69
<211> LENGTH: 13
<212> TYPE: PRT
<213> ORGANISM: Escherichia coli

<400> SEQUENCE: 69

Gly Ser Asn Gly Gln Ala Asn Asn Asp Ala Ser Gln
1               5                   10

<210> SEQ ID NO 70
<211> LENGTH: 12
<212> TYPE: PRT
<213> ORGANISM: Escherichia coli

<400> SEQUENCE: 70

Thr Ser Gly Thr Ala Pro Ser Ala Gly Lys Tyr Gln
1               5                   10

<210> SEQ ID NO 71
<211> LENGTH: 13
<212> TYPE: PRT
<213> ORGANISM: Escherichia coli

<400> SEQUENCE: 71

Ala Asp Thr Gln Gly Thr Ala Pro Glu Ala Gly Asn Tyr
1               5                   10

<210> SEQ ID NO 72
<211> LENGTH: 10
<212> TYPE: PRT
<213> ORGANISM: Escherichia coli

<400> SEQUENCE: 72

Glu Ala Ala Pro Pro Glu Ala Gly Asn Tyr
1               5                   10

<210> SEQ ID NO 73
<211> LENGTH: 12
<212> TYPE: PRT
<213> ORGANISM: Escherichia coli

<400> SEQUENCE: 73

Lys Lys Ser Pro Asp Ile Glu Asp Tyr Gln Glu Arg
1               5                   10

<210> SEQ ID NO 74
<211> LENGTH: 729
<212> TYPE: DNA
<213> ORGANISM: Escherichia coli

<400> SEQUENCE: 74

```
atgagcctgc tggaagttat cattgttctt ggcattatcg gtacgattgc agccggtgtc      60
gtgattctgg ctcagcgtgc gtttgattca cgtgctgtga ctgatttaga agctgctccg     120
cctgaggcag gtaattacac agtccgcgta gcaatgaaag atgcttatca acgtgatggt     180
aaatatccag attttgtgga cccattaagc cttactgcaa atacaattaa aactgataca     240
agcggaatac ctgcagcaca gttagttcag cttgggaaag cagacacaca aggaactgcg     300
cctgaggcag gcaattacat ttctggcgac tttatcgcta ttggcggtgc tgtggagggc     360
gaaaagtccc cccgtcgtgg cgtgaaaaaa ggttttgcta tcgaacttaa tggattaaca     420
tccggaactg caccaagtgc aggtaagtat caagagcagt gccgttctat tcttgggcaa     480
gttgggctg atcgccggt tacacgtagt gatacgacat cttgggaata tgttgctggt      540
agtaacggcc aagcgaataa caatgatgca agccaggtag atatgtctgt ggccgcctct     600
acaactgttt tacgctcttt aggtaacaaa aaatcgccgg atattgagga ttatcaggaa     660
cgcactgcag acaaaattct aagtacctgt actgctcagg taaactcaat tactttaggt     720
agccgttaa                                                             729

<210> SEQ ID NO 75
<211> LENGTH: 203
<212> TYPE: PRT
<213> ORGANISM: Escherichia coli

<400> SEQUENCE: 75

Met Lys Lys Lys Leu Leu Ile Ala Ser Val Leu Ala Met Ala Thr Val
1               5                   10                  15

Ser Gly Ser Val Leu Ala Ala Val Thr Asn Gly Gln Leu Thr Phe Asn
                20                  25                  30

Trp Gln Gly Val Val Pro Ser Ala Pro Val Thr Lys Asn Thr Trp Ala
            35                  40                  45

Phe Val Asn Gly Leu Asp Ile Pro Phe Thr Pro Gly Thr Glu Gln Leu
        50                  55                  60

Asn Ile Thr Leu Gly Ala Asp Lys Gly Ile Thr Ala Arg Ser Val Lys
65                  70                  75                  80

Pro Tyr Asp Phe Phe Ile Val Pro Val Thr Gly Thr Val Thr Ala Gly
                85                  90                  95

Ser Pro Val Thr Arg Ser Asp Thr Thr Ser Met Asn Ser Val Lys Ala
                100                 105                 110

Phe Leu Ser Ser Glu Pro Val Ser Asn Gly Phe Val Gly Asn Lys Gln
            115                 120                 125

Leu Thr Leu Ser Thr Thr Ala Glu Ala Val Thr Gly Gln Val Ala Ile
        130                 135                 140

Thr Leu Asn Gly Gln Pro Leu Lys Val Gly Ser Ala Asn Ala Thr Thr
145                 150                 155                 160

Val Ala Met Asp Thr Asn Lys Lys Glu Ser His Ile Ser Ile Asp Met
                165                 170                 175

Asn Ala Lys Ala Ser Ala Ser Asp Val Ala Glu Gly Ser Ala Ile Asn
                180                 185                 190

Phe Val Ala Pro Val Thr Phe Ala Val Asp Ile
            195                 200

<210> SEQ ID NO 76
<211> LENGTH: 612
<212> TYPE: DNA
<213> ORGANISM: Escherichia coli
```

<400> SEQUENCE: 76

```
atgaagaaaa aattactgat agcttcagta ttagcaatgg caaccgtatc aggttctgtt      60
ttggctgctg ttacaaatgg ccagctcaca tttaattggc agggagtggt tccttctgct     120
cccgttacta aaaatacgtg ggcttttgtg aacggattgg atataccgtt tactcctggt     180
actgaacagt tgaatatcac ccttggtgca gataaaggta tcacagcccg ttcggttaag     240
ccttatgatt ttttcattgt tccagttact ggaacagtaa ctgctggatc gccggttaca     300
cgtagtgata cgacatctat gaatagtgtg aaagcttttc tatcaagtga acccgtttct     360
aatggttttg ttggcaacaa gcagttaacc ctgagcacca cagcagaagc agttacgggg     420
caagtcgcaa tcactttaaa tggtcagccg cttaaagtgg ggagtgctaa tgcaacaact     480
gttgctatgg ataccaataa aaaagagtct catatttcta ttgatatgaa tgccaaggca     540
agtgcttcgg atgtggcgga gggttcagct attaactttg tagctccggt aacatttgct     600
gttgatattt aa                                                          612
```

<210> SEQ ID NO 77
<211> LENGTH: 26
<212> TYPE: DNA
<213> ORGANISM: Escherichia coli

<400> SEQUENCE: 77

```
cgccatggaa atggcaaccg tatcag                                            26
```

<210> SEQ ID NO 78
<211> LENGTH: 31
<212> TYPE: DNA
<213> ORGANISM: Escherichia coli

<400> SEQUENCE: 78

```
tcggccgctt tacgccacat ccgaagcact t                                      31
```

<210> SEQ ID NO 79
<211> LENGTH: 196
<212> TYPE: PRT
<213> ORGANISM: Escherichia coli

<400> SEQUENCE: 79

```
Met Arg Lys Ile Thr Ser Leu Ile Met Ala Val Thr Leu Met Asn Ser
1               5                   10                  15

Ser Ala Phe Ala Ala Ile Gly Ser Asn Gly Gln Ala Asn Asn Asn Asp
            20                  25                  30

Ala Ser Gln Ala Glu Leu His Phe Thr Gly Lys Leu Thr Ser Ser Leu
        35                  40                  45

Cys Gln Val Ala Thr Ser Asp Val Lys Lys Glu Ile Asp Leu Gly Glu
    50                  55                  60

Leu Ser Lys Ala Ala Leu Ile Ala Ser Gly Arg Gly Pro Ser Gln Ser
65                  70                  75                  80

Phe Ser Val Ser Leu Val Asn Cys Asp Pro Thr Ile Asn Thr Ile Ser
                85                  90                  95

Tyr Ala Leu Gln Asp Lys Asn Gly Ser Val Gly Asn Tyr Leu Val Asn
            100                 105                 110

Gln Ser Gly Asp Thr Met Ala Lys Gly Val Gly Val Tyr Ile Glu Asn
        115                 120                 125

Asn Leu Asn Ser Pro Leu Lys Val Asp Gly Ser Leu Asn Thr Val Gly
    130                 135                 140
```

Val Gln Lys Asp Gly Ala Thr Ala Leu Pro Asp Gln Val Ile Pro Leu
145                 150                 155                 160

Thr Ala Tyr Ile Gly Ser Thr Thr Pro Gly Ala Val Ala Asp Phe Ala
            165                 170                 175

Thr Val Thr Pro Gly Leu Val Asp Ala Asn Ala Val Met Thr Ile Arg
        180                 185                 190

Ala Ser Ala Pro
        195

<210> SEQ ID NO 80
<211> LENGTH: 591
<212> TYPE: DNA
<213> ORGANISM: Escherichia coli

<400> SEQUENCE: 80
atgagaaaaa ttacgtctct gatcatggct gttactctaa tgaatagctc agccttcgct      60
gcgatcggta gtaacggcca agcgaataac aatgatgcaa gccaggctga attgcatttc    120
actggtaagt tgacttccag tctatgccag gttgctacat cagatgttaa aaagaaatt     180 gatctagggg aacttagcaa agctgcgtta attgcatcag gtcgagggcc atcgcagtct    240
ttttcagtta gtttggtaaa ctgtgacccc acaataaata caattagtta tgctttgcag    300
gataaaaacg gcagtgtagg taattatctt gtaaaccagt caggtgacac gatggctaag    360
ggggttggtg tctatattga aaataattta atagcccctt tgaaggttga tggttcactt    420
aatactgttg gtgttcagaa agatggtgct acggctttac ctgatcaggt tattccgttg    480
actgcttata ttggtagcac aactccggga gctgtggccg attttgctac agtaactcct    540
ggcttagttg atgcaaatgc agtaatgact attcgtgcga gcgcaccata a             591

<210> SEQ ID NO 81
<211> LENGTH: 39
<212> TYPE: DNA
<213> ORGANISM: Escherichia coli

<400> SEQUENCE: 81
catgccatgg aaatggctgt tactctaatg aatagctca                             39

<210> SEQ ID NO 82
<211> LENGTH: 39
<212> TYPE: DNA
<213> ORGANISM: Escherichia coli

<400> SEQUENCE: 82
gagtcggccg ctttatgaac accaacagta ttaagtgaa                             39

<210> SEQ ID NO 83
<211> LENGTH: 175
<212> TYPE: PRT
<213> ORGANISM: Escherichia coli

<400> SEQUENCE: 83

Met Lys Leu Lys Lys Thr Ile Gly Ala Met Ala Leu Ser Thr Ile Phe
1               5                   10                  15

Val Ala Val Ser Ala Ser Ala Val Glu Lys Asn Ile Thr Val Thr Ala
            20                  25                  30

Ser Val Asp Pro Thr Ile Asp Ile Leu Gln Ala Asn Gly Ser Ala Leu
        35                  40                  45

Pro Thr Ala Val Asp Leu Thr Tyr Leu Pro Gly Ala Lys Thr Phe Glu
    50                  55                  60

Asn Tyr Ser Val Leu Thr Gln Ile Tyr Thr Asn Asp Pro Ser Lys Gly
65                  70                  75                  80

Leu Asp Val Arg Leu Val Asp Thr Pro Lys Leu Thr Asn Ile Leu Gln
                85                  90                  95

Pro Thr Ser Thr Ile Pro Leu Thr Val Ser Trp Ala Gly Lys Thr Leu
            100                 105                 110

Ser Thr Ser Ala Gln Lys Ile Ala Val Gly Asp Leu Gly Phe Gly Ser
        115                 120                 125

Thr Gly Thr Ala Gly Val Ser Asn Ser Lys Glu Leu Val Ile Gly Ala
    130                 135                 140

Thr Thr Ser Gly Thr Ala Pro Ser Ala Gly Lys Tyr Gln Gly Val Val
145                 150                 155                 160

Ser Ile Val Met Thr Gln Ser Thr Asp Thr Ala Ala Pro Val Pro
                165                 170                 175

<210> SEQ ID NO 84
<211> LENGTH: 510
<212> TYPE: DNA
<213> ORGANISM: Escherichia coli

<400> SEQUENCE: 84
atgaaattaa aaaaaactat tggcgcaatg gctctgagca caatatttgt agcggtgagt      60
gcttcagcag tagagaaaaa tattactgtg acagccagtg ttgatcctac tattgatatt     120
cttcaagcaa atggttctgc gctaccgaca gctgtagatt taacttatct acctggtgca     180
aaaacttttg aaaattacag tgttctaacc cagatttaca caaatgaccc ttcaaaaggt     240
ttagatgttc gactggttga tacaccgaaa cttacaaata ttttgcaacc gacatctacc     300
attcctctta ctgtctcatg ggcagggagg acattaagta caagtgctca gaagatcgca     360
gttggcgatc tgggttttgg ttccaccgga acggcaggtg tttcgaatag taagaattta     420
gtaattggag caactacatc cggaactgca ccaagtgcag gtaagtatca aggcgtcgtt     480
tccattgtaa tgactcaatc gacaaactaa                                      510

<210> SEQ ID NO 85
<211> LENGTH: 37
<212> TYPE: DNA
<213> ORGANISM: Escherichia coli

<400> SEQUENCE: 85
catgccatgg aaatggctct gagcacaata tttgtag                              37

<210> SEQ ID NO 86
<211> LENGTH: 42
<212> TYPE: DNA
<213> ORGANISM: Escherichia coli

<400> SEQUENCE: 86
gagtcggccg ctttagtttg tcgattgagt cattacaatg ga                        42

<210> SEQ ID NO 87
<211> LENGTH: 168
<212> TYPE: PRT
<213> ORGANISM: Escherichia coli

<400> SEQUENCE: 87

Met Lys Leu Lys Lys Thr Ile Gly Ala Met Ala Met Ala Thr Leu Phe
1               5                   10                  15

```
Ala Thr Met Ala Ala Ser Ala Val Glu Lys Asn Ile Thr Val Arg Ala
            20                  25                  30

Ser Val Asp Pro Lys Leu Asp Leu Leu Gln Ala Asp Gly Thr Ser Leu
        35                  40                  45

Pro Asp Ser Ile Ala Leu Thr Tyr Ser Ser Ala Ser Asn Asn Phe Glu
    50                  55                  60

Val Tyr Ser Leu Asn Thr Ala Ile His Thr Asn Asp Lys Ser Lys Gly
65                  70                  75                  80

Val Val Val Lys Leu Ser Ala Ser Pro Val Leu Ser Asn Ile Met Lys
                85                  90                  95

Pro Asn Ser Gln Ile Pro Met Lys Val Thr Leu Gly Gly Lys Thr Leu
            100                 105                 110

Asn Thr Thr Asp Thr Glu Phe Thr Val Asp Thr Leu Asn Phe Gly Thr
            115                 120                 125

Ser Gly Val Glu Asn Val Ser Ser Thr Gln Gln Leu Thr Ile His Ala
        130                 135                 140

Asp Thr Gln Gly Thr Ala Pro Glu Ala Gly Asn Tyr Gln Gly Ile Ile
145                 150                 155                 160

Ser Leu Ile Met Thr Gln Lys Thr
                165
```

<210> SEQ ID NO 88
<211> LENGTH: 507
<212> TYPE: DNA
<213> ORGANISM: Escherichia coli

<400> SEQUENCE: 88

```
atgaaactga agaaaacaat tggcgcaatg gctatggcga ctctgtttgc caccatggct      60
gcctctgcag tcgaaaaaaa tattactgtg agggcaagtg ttgaccctaa acttgatctt     120
ctgcaagcag atggaacttc actgccggac tctatcgcat taacctattc ttcggcttca     180
aataattttg aagtttactc tcttaatact gctattcata caaatgacaa agcaaggga      240
gttgtagtga agctgtcagc ttcaccagtt ctgtccaata ttatgaagcc aaactcgcaa     300
attccgatga agtgactttt ggggggggaag acgctgaata caactgatac tgagtttact     360
gttgatactc tgaactttgg tacatctggt gttgaaaacg tttcttccac tcaacagctt     420
acgattcatg cagacacaca aggaactgcg cctgaggcag gcaattacca aggtattatt     480
tctcttatca tgactcaaaa aacttaa                                         507
```

<210> SEQ ID NO 89
<211> LENGTH: 37
<212> TYPE: DNA
<213> ORGANISM: Escherichia coli

<400> SEQUENCE: 89

```
ctagctagct agatggctat ggcgactctg tttgcca                                37
```

<210> SEQ ID NO 90
<211> LENGTH: 41
<212> TYPE: DNA
<213> ORGANISM: Escherichia coli

<400> SEQUENCE: 90

```
gagtcggccg ctttataata ccttggtaat tgcctgcctc a                           41
```

<210> SEQ ID NO 91
<211> LENGTH: 166

```
<212> TYPE: PRT
<213> ORGANISM: Escherichia coli

<400> SEQUENCE: 91

Met Lys Leu Lys Lys Thr Ile Gly Ala Met Ala Met Ala Thr Leu Phe
1               5                   10                  15

Ala Thr Met Ala Ala Ser Ala Val Glu Lys Asn Ile Thr Val Arg Ala
            20                  25                  30

Ser Val Asp Pro Lys Leu Asp Leu Leu Gln Ala Asp Gly Thr Ser Leu
        35                  40                  45

Pro Asp Ser Ile Ala Leu Thr Tyr Ser Ser Ala Ser Asn Asn Phe Glu
    50                  55                  60

Val Tyr Ser Leu Asn Thr Ala Ile His Thr Asn Asp Lys Thr Lys Ala
65                  70                  75                  80

Val Val Val Lys Leu Ser Ala Pro Ala Val Leu Ser Asn Ile Met Lys
                85                  90                  95

Pro Ser Ser Gln Ile Pro Met Lys Val Thr Leu Gly Gly Lys Thr Leu
            100                 105                 110

Ser Thr Ala Asp Ala Glu Phe Ala Ala Asp Thr Leu Asn Phe Gly Ala
        115                 120                 125

Ser Gly Val Glu Asn Val Ser Ser Val Gln Gln Leu Thr Ile His Ala
    130                 135                 140

Glu Ala Ala Pro Pro Glu Ala Gly Asn Tyr Gln Gly Val Ile Ser Leu
145                 150                 155                 160

Ile Met Thr Gln Lys Thr
                165

<210> SEQ ID NO 92
<211> LENGTH: 501
<212> TYPE: DNA
<213> ORGANISM: Escherichia coli

<400> SEQUENCE: 92
atgaaactga agaaaacaat tggcgcaatg gctatggcga ctctgtttgc caccatggct    60
gcctctgcag tcgaaaaaaa tattactgtg agggcaagtg ttgaccctaa acttgatctt   120
ctgcaagcag atggaacttc actgccggac tctatcgcat taacctattc ttcggcttca   180
aataattttg aagtttactc tcttaatact gctattcata caaatgacaa aaccaaggca   240
gttgtagtga agctgtcagc tccagcagtt ctgtccaata ttatgaagcc aagctcgcaa   300
attccgatga agtgactttt ggggggggaag acgctgagta cagctgatgc tgagtttgct   360
gctgatactc tgaactttgg tgcatctggt gttgaaaacg tttcttccgt tcaacagctt   420
acgattcatg cagaagctgc tccgcctgag gcaggtaatt accaaggtgt tatttctctt   480
atcatgactc aaaaaactta a                                             501

<210> SEQ ID NO 93
<211> LENGTH: 37
<212> TYPE: DNA
<213> ORGANISM: Escherichia coli

<400> SEQUENCE: 93
ctagctagct agatggctat ggcgactctg tttgcca                             37

<210> SEQ ID NO 94
<211> LENGTH: 39
<212> TYPE: DNA
<213> ORGANISM: Escherichia coli
```

<400> SEQUENCE: 94
gagtcggccg ctttagagtc atgataagag aaataacac                                39

<210> SEQ ID NO 95
<211> LENGTH: 206
<212> TYPE: PRT
<213> ORGANISM: Escherichia coli

<400> SEQUENCE: 95

Met Ser Leu Leu Glu Val Ile Ile Val Leu Gly Ile Ile Gly Thr Ile
1               5                   10                  15

Ala Ala Gly Val Val Ile Leu Ala Gln Arg Ala Phe Asp Ser Arg Ala
            20                  25                  30

Val Thr Asp Leu Val Thr Asn Thr Asn Thr Val Arg Val Ala Met Lys
        35                  40                  45

Asp Ala Tyr Gln Arg Asp Gly Lys Tyr Pro Asp Phe Val Asp Pro Leu
    50                  55                  60

Ser Leu Thr Ala Asn Thr Ile Lys Thr Asp Thr Ser Gly Ile Pro Ala
65                  70                  75                  80

Ala Gln Leu Val Gln Leu Gly Lys Ile Thr Pro Asp Glu Val Arg Asn
                85                  90                  95

Asn Ile Ser Gly Asp Phe Ile Ala Ile Gly Gly Ala Leu Thr Ser Asn
            100                 105                 110

Gly Ala Gln Val Lys Lys Gly Phe Ala Ile Glu Leu Asn Gly Leu Ser
        115                 120                 125

Gln Glu Gln Cys Arg Ser Ile Leu Gly Gln Val Gly Asn Asn Trp Glu
    130                 135                 140

Tyr Val Ala Ile Gly Thr Ser Ala Ser Gly Ser Tyr Ala Met Thr Ala
145                 150                 155                 160

Thr Gly Val Asp Met Ser Val Ala Ala Ser Thr Thr Val Leu Arg Ser
                165                 170                 175

Leu Gly Asn Gly Gly Gln Thr Thr Leu Thr Ala Asp Lys Ile Leu Ser
            180                 185                 190

Thr Cys Thr Ala Gln Val Asn Ser Ile Thr Leu Gly Ser Arg
        195                 200                 205

<210> SEQ ID NO 96
<211> LENGTH: 621
<212> TYPE: DNA
<213> ORGANISM: Escherichia coli

<400> SEQUENCE: 96
atgagcctgc tggaagttat cattgttctt ggcattatcg gtacgattgc agccggtgtc    60
gtgattctgg ctcagcgtgc gtttgattca cgtgctgtga ctgatttagt aactaataca   120
aatacagtcc gcgtagcaat gaaagatgct tatcaacgtg atggtaaata tccagatttt   180
gtggacccat taagccttac tgcaaataca attaaaactg atacaagcgg aatacctgca   240
gcacagttag ttcagcttgg gaaaattaca ccagacgaag tgcgtaataa catttctggc   300
gactttatcg ctattggcgg tgctttaact tcgaatggtg ctcaagttaa aaaggttttt   360
gctatcgaac ttaatggatt aagccaagag cagtgccgtt ctattcttgg gcaagttggg   420
aataactggg aatatgttgc tattggtact tctgcgtctg gttcatatgc catgacagca   480
actggtgtag atatgtctgt ggccgcctct acaactgttt tacgctcttt aggtaacggt   540
ggacaaacaa ccttgactgc agacaaaatt ctaagtacct gtactgctca ggtaaactca   600

-continued attactttag gtagccgtta a                                      621

<210> SEQ ID NO 97
<211> LENGTH: 39
<212> TYPE: DNA
<213> ORGANISM: Escherichia coli

<400> SEQUENCE: 97
catgccatgg gcatgagcct gctggaagtt atcattgtt                   39

<210> SEQ ID NO 98
<211> LENGTH: 37
<212> TYPE: DNA
<213> ORGANISM: Escherichia coli

<400> SEQUENCE: 98
gagtcggccg ctttaacggc tacctaaagt aattgag                     37

<210> SEQ ID NO 99
<211> LENGTH: 216
<212> TYPE: PRT
<213> ORGANISM: Escherichia coli

<400> SEQUENCE: 99

Val Ser Glu Ile Thr Thr Gly Val Gly Asn Ala Lys Ala Thr Gly Ser
1               5                   10                  15

Val Glu Gly Glu Lys Ser Pro Arg Arg Gly Val Arg Ala Met Ala Leu
            20                  25                  30

Ser Leu Leu Ser Gly Met Met Ile Met Ala His Pro Ala Met Ser Ala
        35                  40                  45

Asn Leu Pro Thr Gly Gly Gln Ile Val Ala Gly Ser Gly Ser Ile Gln
    50                  55                  60

Thr Pro Ser Gly Asn Gln Met Asn Ile His Gln Asn Ser Gln Asn Met
65                  70                  75                  80

Val Ala Asn Trp Asn Ser Phe Asp Ile Gly Lys Gly Asn Thr Val Gln
                85                  90                  95

Phe Asp Gln Pro Ser Ser Ser Ala Val Ala Leu Asn Arg Val Val Gly
            100                 105                 110

Gly Gly Glu Ser Gln Ile Met Gly Asn Leu Lys Ala Asn Gly Gln Val
        115                 120                 125

Phe Leu Val Asn Pro Asn Gly Val Leu Phe Gly Glu Gly Ala Ser Val
    130                 135                 140

Ser Thr Ser Gly Phe Val Ala Ser Thr Arg Asp Ile Lys Asn Asp Asp
145                 150                 155                 160

Phe Met Asn Arg Arg Tyr Thr Phe Ser Gly Gly Gln Lys Ala Gly Ala
                165                 170                 175

Ala Ile Val Asn Gln Gly Glu Leu Thr Thr Asn Ala Gly Gly Tyr Ile
            180                 185                 190

Val Leu Ala Ala Asp Arg Val Ser Asn Ser Gly Thr Ile Arg Thr Pro
        195                 200                 205

Gly Gly Lys Thr Val Leu Ala Ala
    210                 215

<210> SEQ ID NO 100
<211> LENGTH: 5304
<212> TYPE: DNA
<213> ORGANISM: Escherichia coli

```
<400> SEQUENCE: 100
atgaaccgta tatataaact gaagtttgac aaacgccgca acgaactggt ggtggtgagt      60
gaaatcacca ccggcgtggg taatgcaaaa gccacgggca gcgtggaggg cgaaaagtcc     120
ccccgtcgtg gcgtgcgcgc catggcgctg agcctgctgt cgggtatgat gataatggcc     180
catccggcga tgtcagcaaa cctgccgacc ggtggccaga ttgtggcagg ttcaggcagt     240
atccagacgc cttccggcaa ccagatgaat attcatcaga acagccagaa catggtggcc     300
aactggaaca gctttgacat tggtaaagga aatacggtgc agtttgacca gcccagcagc     360
agtgcggtgg cgctgaaccg tgttgtgggt ggcggtgaat cgcagattat gggtaacctg     420
aaggcgaatg gtcaggtgtt cctggttaac ccgaacggcg tgctgtttgg tgaggggggcc    480 agtgtcagca cgtcaggttt tgtggcatcg acccgcgaca ttaaaaacga cgacttcatg     540
aaccgtcgtt acaccttcag cggcggacag aaagccgggg cagcgattgt gaaccagggg     600
gaactgacca caaatgccgg tggctatatt gtgctggcag cagacagggt cagcaacagt     660
ggcaccatcc gtacgccggg cggcaagacc gtcctggcgg ccagcgagcg catcacgctg     720
cagctggata tggtggcct gatgtccgtg caggtgacag agatgtggt taatgccctg       780 gtggaaaacc gcggtctggt cagtgcccgg gatggtcagg tgtacctgac cgcacttggc     840
cggggtatgc tgatgaacac ggtactgaac gtgagcgggg tggtggaagc cagcggtatg     900
caccgtcagg acggtaacat tgtactggac ggtggcgaca gtggtgtggt gcacctgagt     960
ggtaccctgc aggcggacaa tgcgtccggt cagggtggta aggttgtcgt gcagggtaag    1020
aatattctgc tggacaaggg cagcaacatc acagcaaccg tggtcagggg cggcggtgaa    1080
gtgtatgtcg gtggcggctg gcagggtaag gacagcaaca tccgtaatgc ggacaaggtg    1140
gtgatgcagg gcgcgcccg cattgacgtt tctgcaacgc agcagggtaa cggcggtacg    1200
gctgtgctgt ggtcagacag ctacaccaac ttccatggtc agattagcgc gaagggcggt    1260
gagaccggcg gtaacggtgg tcgggtggag acctcttcgc acggtaacct gcaggcattt    1320
ggtacggtca gtgcatccgc gaagaaaggc aaggcgggta actggctgct ggactcggcg    1380
gatatcacca ttgtgaatgg tagcaatgtt agcaaaactg agacgactca atcgccgccg    1440
cacacgcaat ttgcacccac cgctgcgggc tctgcggtca gcaataccag tatcaacaac    1500
aggctgaaca acgggaccag tgtcactatt ctgacccatc gcacaagaac aggcacagct    1560
cagggcggga atattaccgt taatgcggca attaacaaaa gcaacggaag tgatgtcaac    1620
ctgacgctgc aggctggcgg caacatcacg gtaaacaaca gcatcacgtc caccgagggt    1680
aagctgaatg ttaatctgtc gggcgccagg accagcaatg gcagtatcac cattagcaat    1740
aacgccaata taacgaccaa tggtgggat ataactgttg gacgacaaa tacttcaaac     1800 cgtgtgaata tatctattaa taacactacc ctgaatgcgt caaatggcaa catccagttg    1860
accgggaccg ggaccgatag cgggattctg tttgctggca acaacaggct gacggccagt    1920
aacattgctc ttaccgggaa cagtacgagt gggaatgcca tcaaccttac aggcactgcc    1980
acgctgaatg ccacgaataa cattactctt accgggagca gtacgagtgg gaatgccatc    2040
aaccttaaag gcaacaacac gctgacggcc agtaacatta ctcttaccgg ggaaagtacg    2100
agtgggaatg ccatcaacct tacagacact acaggcacta ccacgctgaa tgccacgaat    2160
aacatcacta tgcagggac ccgtgttcag attaaacact ccaacatcac cgcgggcaac     2220
tttgcgctga tgcgacagt ggccggctct gaaatcagca ataccacgct gacggccacc     2280
aacaacatca acctggcggc taagacgaac agtgcgagct ctggtgttta cctgaaagat    2340
```

```
gcaagaatta catccaccaa tggcagtatc acggctaacg gtactgccac agcaaacggc      2400
aaggccacgc atctggacgg caacgtcacc ctgaatgcgt caaatggcag aatcaagttg      2460
accgggaacg ggcacggtag cgcctccggg attctgtttg ctggcaacaa caggctgacg      2520
gccagtaaca ttgctcttac cgggaacagt acgagtggga atgccatcaa ccttacaggc      2580
actgccacgc tgaatgccac gaatgacatt actcttaccg ggagcagtac gagtgggaat      2640
gccatcaacc ttacaggcac tgccacgctg aatgccacga taacattac tcttaccggg       2700 agcagtacga gtgggaatgc catcaacctt aaaggcaaca cacgctgac ggccagtaac       2760 attactctta ccggggaaag tacgagtggg aatgccatca accttacaga cactacaggc      2820
actaccacgc tgaatgccac gaataacatc actatgcagg gacccgtgt tcagattaaa       2880 cactccaaca tcaccgcggg caactttgcg ctgaatgcga cagtggccgg ctctgaaatc      2940
agcaatacca cgctgacggc caccaacaac atcaacctgg cggctaagac gaacagtgcg      3000
agctctggtg tttacctgaa agatgcaaga attacatcca ccaatggcag tatcacggct      3060
aacggtactg ccacagcaaa cggcaaggcc acgcatctgg acggcaacgt caccctgaat      3120
gcgtcaaatg gcagaatcaa gttgaccggg aacgggcacg gtagcgcctc cgggattctg      3180
tttgctggca acaacaggct gacggccagt aacattgctc ttaccgggaa cagtacgagt      3240
gggaatgcca tcaaccttac aggcactgcc acgctgaatg ccacgaatga cattactctt      3300
accgggagca gtacgagtgg gaatgccatc aaccttacag gcactgccac gctgaatgcc      3360
acgaataaca ttactcttac cgggagcagt acgagtggga atgccatcaa ccttaaaggc      3420
aacaacacgc tgacggccag taacattact cttaccgggg aaagtacgag tgggaatgcc      3480
atcaacctta cagacactac aggcactacc acgctgaatg ccacgaataa catcactatg      3540
caggggaccc gtgttcagat taaacactcc aacatcaccg cgggcaactt tgcgctgaat      3600
gcgacagtgg ccggctctga atcagcaat accacgctga cggccaccaa caacatcaac      3660
ctggcggcta agacgaacag tgcgagctct ggtgtttacc tgaaagatgc aagaattaca      3720
tccaccaatg gcagtatcac ggctaacggt actgccacag caaacggcaa ggccacgcat      3780
ctggacggca acgtcaccct gaatgcgtca atggcagaa tcaagttgac cgggaacggg      3840
cacggtagcg cctccgggat tctgtttgct ggcaacaaca ggctgacggc cagtaacatt      3900
gctcttaccg gaacagtac gagtgggaat gccatcaacc ttacaggcac tgccacgctg       3960
aatgccacga atgacattac tcttaccggg agcagtacga gtgggaatgc catcaacctt      4020
acaggcactg ccacgctgaa tgccacgaat aacattactc ttaccgggag cagtacgagt      4080
gggaatgcca tcaaccttaa aggcaacaac acgctgacgg ccagtaacat tactcttacc      4140
ggggaaagta cgagtgggaa tgccatcaac cttacagaca ctacaggcac taccacgctg      4200
aatgccacga ataacatcac tatgcagggg acccgtgttc agattaaaca ctccaacatc      4260
accgcgggca actttgcgct gaatgcgaca gtggccggct ctgaaatcag caataccacg      4320
ctgacggcca ccaacaacat caacctggcg gctaagacga acagtgcgag ctctggtgtt      4380
tacctgaaag atgcaagaat tacatccact aatggcagta tcacgactaa cggtactgcc      4440
acagcaaacg gcaaggccac gcatctggac ggcaacgtca ccctgaatgc gtcaaatggc      4500
agaatcaagt tgaccgggaa cgggcacggt agcgcctccg ggattctgtt tgctggcaac      4560
aacaggctga cggccagtaa cattgctctt accgggaaca gtacgagtgg gaatgccatc      4620
aaccttacag gcactgccac gctgaatgcc acgaatgaca ttactcttac cgggagcagt      4680
```

-continued

```
acgagtggga atgccatcaa ccttacaggc actgccacgc tgaatgccac gaataacatt    4740
actcttaccg ggagcagtac gagtgggaat gccatcaacc ttaaaggcaa caacacgctg    4800
acggccagta acattactct taccggggaa agtacgagtg ggaatgccat caaccttaca    4860
gacactacag gcactaccac gctgaatgcc acgaataaca tcactatgca ggggacccgt    4920
gttcagatta aacactccaa catcaccgcg ggcaactttg cgctgaatgc gacagtggcc    4980
ggctctgaaa tcagcaatac cacgctgacg gccaccaaca acatcaacct ggcggctaag    5040
acgaacagtg cgagctctgg tgtttacctg aaagatgcaa gaattacatc caccaatggc    5100
agtatcacgg ctaacggtac tgccccagca acgacaatg ccacgtatct ggacggcaac    5160
gtcaccctga atgcgtcaaa tggcagcatc aagttgaccg ggaacgggaa cggtagcacc    5220
tccgggattc tgtttgctgg caacaacacg ctgacggcca gtaacattac tcttaccggg    5280
aacagtgagg tgtactggca atag                                          5304
```

<210> SEQ ID NO 101
<211> LENGTH: 33
<212> TYPE: DNA
<213> ORGANISM: Escherichia coli

<400> SEQUENCE: 101
ctagctagct agatgaaccg tatatataaa ctg                                 33

<210> SEQ ID NO 102
<211> LENGTH: 40
<212> TYPE: DNA
<213> ORGANISM: Escherichia coli

<400> SEQUENCE: 102
gagtcggccg ctttataatc tgaccatgga agttggtgta                          40

<210> SEQ ID NO 103
<211> LENGTH: 290
<212> TYPE: PRT
<213> ORGANISM: Escherichia coli

<400> SEQUENCE: 103

Met Ser His Tyr Lys Thr Gly His Lys Gln Pro Arg Phe Arg Tyr Ser
1               5                   10                  15

Val Leu Ala Arg Cys Val Ala Trp Ala Asn Ile Ser Val Gln Val Leu
            20                  25                  30

Phe Pro Leu Ala Val Thr Phe Thr Pro Val Met Ala Ala Arg Ala Gln
        35                  40                  45

His Ala Val Gln Pro Arg Leu Ser Met Gly Asn Thr Thr Val Thr Ala
    50                  55                  60

Asp Asn Asn Val Glu Lys Asn Val Ala Ser Phe Ala Ala Asn Ala Gly
65                  70                  75                  80

Thr Phe Leu Ser Ser Gln Pro Asp Ser Asp Ala Thr Arg Asn Phe Ile
                85                  90                  95

Thr Gly Met Ala Thr Ala Lys Ala Asn Gln Glu Ile Gln Glu Trp Leu
            100                 105                 110

Gly Lys Tyr Gly Thr Ala Arg Val Lys Leu Asn Val Asp Lys Asp Phe
        115                 120                 125

Ser Leu Lys Asp Ser Ser Leu Glu Met Leu Tyr Pro Ile Tyr Asp Thr
    130                 135                 140

Pro Thr Asn Met Leu Phe Thr Gln Gly Ala Ile His Arg Thr Asp Asp
145                 150                 155                 160

```
Arg Thr Gln Ser Asn Ile Gly Phe Gly Trp Arg His Phe Ser Gly Asn
                165                 170                 175

Asp Trp Met Ala Gly Val Asn Thr Phe Ile Asp His Asp Leu Ser Arg
            180                 185                 190

Ser His Thr Arg Ile Gly Val Gly Ala Glu Tyr Trp Arg Asp Tyr Leu
        195                 200                 205

Lys Leu Ser Ala Asn Gly Tyr Ile Arg Ala Ser Gly Trp Lys Lys Ser
    210                 215                 220

Pro Asp Ile Glu Asp Tyr Gln Glu Arg Pro Ala Asn Gly Trp Asp Ile
225                 230                 235                 240

Arg Ala Glu Gly Tyr Leu Pro Ala Trp Pro Gln Leu Gly Ala Ser Leu
                245                 250                 255

Met Tyr Glu Gln Tyr Tyr Gly Asp Glu Val Gly Leu Phe Gly Lys Asp
            260                 265                 270

Lys Arg Gln Lys Asp Pro His Ala Ile Ser Ala Glu Val Thr Tyr Thr
        275                 280                 285

Pro Val
    290

<210> SEQ ID NO 104
<211> LENGTH: 4257
<212> TYPE: DNA
<213> ORGANISM: Escherichia coli

<400> SEQUENCE: 104
```

| | |
|---|---:|
| atgtcacatt ataaaacagg tcataaacaa ccacgatttc gttattcagt tctggcccgc | 60 |
| tgcgtggcgt gggcaaatat ctctgttcag gttctttttc cactcgctgt cacctttacc | 120 |
| ccagtaatgg cggcacgtgc gcagcatgcg gttcagccac ggttgagcat gggaaatact | 180 |
| acggtaactg ctgataataa cgtggagaaa aatgtcgcgt cgtttgccgc aaatgccggg | 240 |
| acattttaa gcagtcagcc agatagcgat gcgacacgta actttattac cggaatggcc | 300 |
| acagctaaag ctaaccagga atacaggag tggctcggga aatatggtac tgcgcgcgtc | 360 |
| aaactgaatg tcgataaaga tttctcgctg aaggattctt cgctggaaat gctttatccg | 420 |
| atttatgata cgccgacaaa tatgttgttc actcaggggg caatacatcg tacagacgat | 480 |
| cgtactcagt caaatattgg ttttggctgg cgtcattttt caggaaatga ctggatggcg | 540 |
| ggggtgaata cttttatcga tcatgattta tcccgtagtc ataccgcat ggtgttggt | 600 |
| gcggaatact ggcgcgatta tctgaaactg agcgccaatg ttatattcg gcttctggc | 660 |
| tggaaaaaat cgccggatat tgaggattat caggaacgcc cggcgaatgg ctgggatatt | 720 |
| cgtgctgagg gctatttacc cgcctggccg cagcttggcg caagcctgat gtatgaacag | 780 |
| tattatggcg atgaagtcgg gctgtttggt aaagataagc gccagaaaga cccgcatgct | 840 |
| atttctgccg aggtgaccta tacgccagtc cctcttctga cactgagcgc cgggcataag | 900 |
| cagggcaaga gtggtgagaa tgacactcgc tttggcctgg aagttaatta tcggattggc | 960 |
| gaacctctgg cgaaacaact cgatacagac agcattcgcg agcgtcgggt actggcaggc | 1020 |
| agccgctatg acctggttga gcgtaataac aacatcgttc ttgagtaccg caaatctgaa | 1080 |
| gtgatccgta ttgctctgcc tgaacgtatt gaaggtaagg gtggtcagac actttccctg | 1140 |
| gggcttgtgg tcagcaaagc aactcacgga ctgaaaaatg tgcagtggga agcgccgtca | 1200 |
| ttactggctg agggtggcaa aattaccggt cagggtagtc agtggcaagt aacgctcccg | 1260 |
| gcttatcgtc caggcaaaga caattattat gcgatttctg cggttgccta cgataacaaa | 1320 |

-continued

```
ggcaatgcct caaaacgcgt gcagacagag gtggtcatta ccggagcagg tatgagcgcc    1380
gatcgcacgg cgttaacgct tgacggtcag agccgtattc aaatgcttgc taacggtaat    1440
gagcaaagac cgctggtgct gtctctgcgc gacgccgagg ggcagccagt cacgggcatg    1500
aaagatcaga tcaagactga actagccttc aaaccggctg gaaatattgt gactcgttcc    1560
ctgaaggcca ctaaatcaca ggcaaagcca acactgggtg agttcaccga aactgaagca    1620
ggggtgtatc agtctgtctt tactaccgga acgcagtcag gtgaggcaac gattactgtt    1680
agcgttgatg gcatgagcaa aaccgtcact gcagaactgc gggccacgat gatggatgtg    1740
gcaaactcca ccctgagcgc taacgagccg tcaggtgatg tggttgctga tggtcagcaa    1800
gcctatacgt tgacgttgac tgcggtggac tccgagggta atccggtgac gggagaagcc    1860
agccgcttgc gatttgttcc gcaagacact aatggtgtaa ccgttggtgc catttcggaa    1920
ataaaaccag gcgtttacag cgccacggtt tcttcgaccc gtgccggaaa cgttgttgtg    1980
cgtgctttca gcgagcagta tcagctgggc acattacaac aaacgctgaa gtttgttgcc    2040
ggtccgcttg atgcagcaca ttcgtccatc ccctgaatc ctgataaacc ggtggttggc    2100
ggtacagtta cggcaatctg gacggcaaaa gatgcctatg acaaccctgt gaccagcctc    2160
acgccggaag cgccgtcatt agcgggtgcc gctgctgtag gttctacggc atctggctgg    2220
acaaataatg gtgatgggac gtggactgcg cagattactc tcggctctac ggcgggtgaa    2280
ttagaagtta tgccgaagct aaatggacag gatgcggcag caaatgcggc aaaagtaacc    2340
gtggtggctg atgcgttatc ttcaaaccag tcgaaagtct ctgtcgcaga agatcacgta    2400
aaagccggcg aaagcacaac cgtgacgctt attgcaaaag atgcacatgg caacactatc    2460
agtggtcttt cgttgtcggc aagtttgacg gggaccgcct ctgaaggggc gaccgtttcc    2520
agttggaccg aaaaaggtga ctgttcctat gttgctacgt taactacagg cggaaagacg    2580
ggcgagcttc gtgtcatgcc gctcttcaac ggccagccag cagccaccga agccgcgcag    2640
ttgacggtca tcgccggaga gatgtcatca gcgaactcta cgcttgttgc ggacaataag    2700
gctccgaccg tcaaaatgac gacgaaactc accttcaccg tgaaggatgc gtacgggaac    2760
ccggtcaccg ggctgaagcc agatgcacca gtgtttagcg gtgccgccag cacggggagt    2820
gagcgtcctt cagcaggaaa ctggacagag aaaggtaatg gggtctacgt ggcgaccta    2880
acgctgggat ctgccgcggg tcagttgtct gtgatgccgc gagtgaacgg ccaaaatgcc    2940
gttgctcagc cactggtgct gaacgttgca ggtgacgcat ctaaggctga gattcgtgat    3000
atgacagtga aggttaataa ccaactggct aatggacagt ctgctaacca gataaccctg    3060
accgtcgtgg acagctatgg taacccgttg caggggcaag aagttacgct gactttaccg    3120
cagggtgtga ccagcaagac ggggaataca gtaacaacca atgcggcagg aaagtggac    3180
attgagctta tgtcaacggt tgcgggggaa cacagcatca cggcctcagt gaataatgct    3240
cagaagacgt tacggtgaa attcaaggcg gatttcagta ccggtcaggc gaccctggag    3300
gttgatggca gcacgccaaa agtggcaaac gacaatgatg cctttacgct gacggcaacg    3360
gttaaggatc aatacggcaa ccttctgcct ggcgctgtgg tcgtctttaa tctgcctcgg    3420
ggcgtcaaac cgcttgcaga cggtaatatc atggtgaacg ccgacaagga gggtaaagcg    3480
gaactgaaag tggtctccgt gactgccgga acgtatgaga tcacggcgtc ggcaggaaat    3540
gaccagcctt cgaatgcgca gtctgtaacg tttgtggccg ataagactac ggcgaccatc    3600
tccagtattg aggtgattgg caaccgtgca gtggcggatg gcaaaaccaa acagacgtat    3660
```

```
aaagttacgg tgactgatgc caataacaac ctgttgaagg atagcgacgt gacgctgact    3720
gccagctcgg aaaatttagt tctggatcct aaagggacgg cgaaaactaa tgagcaagga    3780
caggctgttt tcaccggctc taccactatc gcagcgacat atacactcac ggcgaaagtg    3840
gaacaggcca acggtcaggt atcgacgaaa actgctgaat ctaaaattcgt cgcggatgat   3900 aaaaacgcgg tgctcgccgc atctccagaa cgtgtagatt ctctggtggc ggacgggaag    3960
actactgcaa caatgacggt taccctgatg gcgggagtca atcccgtagg aggaagtatg    4020
tgggtcgaca ttgaggctcc ggaaggagtg acggagaagg attatcaatt cctgccgtcg    4080
aaggctgacc atttctcagg tgggaaaatc acgcgtacat ttagtaccag caagccaggt    4140
gtctatacgt tcacattcaa cgcactgacg tatggcgggt acgaaatgac gcctgtgaag    4200
gtgacaatta acgccgttgc tgcagagact gaaaatggcg aggaggagat gccataa       4257

<210> SEQ ID NO 105
<211> LENGTH: 35
<212> TYPE: DNA
<213> ORGANISM: Escherichia coli

<400> SEQUENCE: 105
catgccatgg aaatgggaaa tactacggta actgc                                35

<210> SEQ ID NO 106
<211> LENGTH: 40
<212> TYPE: DNA
<213> ORGANISM: Escherichia coli

<400> SEQUENCE: 106
gagtcggccg cattaggttc gccaatccga taattaactt                           40

<210> SEQ ID NO 107
<211> LENGTH: 13
<212> TYPE: PRT
<213> ORGANISM: Escherichia coli

<400> SEQUENCE: 107

Asn Thr Ile Lys Thr Asp Thr Ser Gly Ile Pro Ala Ala
1               5                   10

<210> SEQ ID NO 108
<211> LENGTH: 12
<212> TYPE: PRT
<213> ORGANISM: Escherichia coli

<400> SEQUENCE: 108

Asp Ala Tyr Gln Arg Asp Gly Lys Tyr Pro Asp Phe
1               5                   10

<210> SEQ ID NO 109
<211> LENGTH: 1086
<212> TYPE: DNA
<213> ORGANISM: Escherichia coli

<400> SEQUENCE: 109
atgaataaga ttttatttat ttttacattg ttttctctct cagtactttt tacatttgct    60
gtatcggcag ataaaattcc cggagatgag aatataacta atattttttgg cccgcgtgac   120 aggaacgaat cttccccccaa acataatata ttaaatgact atattacagc atacagtgaa   180
agtcatactc tgtatgatag gatgattttt ttatgtttgt cttctcaaaa tacacttaat    240
ggagcatgtc caaccagtga gaatcctagc agttcatcgg tcagtggcga aacaaatata    300
```

```
acattacaat ttacggaaaa aagaagttta attaaaagag agctacaaat taaaggctat    360
aaacgattat tgttcaaagg tgctaactgc ccatcctacc taacacttaa ctcagctcat    420
tatacctgca atagaaactc ggcttcaggt gcaagtttat atttatatat tcctgctggc    480
gaactaaaaa atttacccttt tggtggtatc tgggatgcta ctctgaagtt aagagtaaaa    540
agacgatatg atcagaccta tggaacttac actataaata tcactgttaa attaactgat    600
aagggaaata ttcagatatg gttacctcag ttcaaaagtg acgctcgcgt cgatcttaac    660
ttgcgtccaa ctggtggggg cacatatatt ggaagaaatt ctgttgatat gtgcttttat    720
gatggatata gtactaacag cagctctttg gagctaagat tcaggataaa caatcctaaa    780
tctgatggga aattttatct aaggaaaata aatgatgaca ccaaagaaat tgcatatact    840
ttgtcacttc tcttggcggg taaaagttta actccaacaa atggaacgtc attaaatatt    900
gctgacgcag cttctctgga aataaactgg aatagaatta cagctgtcac catgccagaa    960
atcagtgttc cggtgttgtg ttggcctgga cgtttgcaat ggatgcaaa agtggaaaat    1020 cccgaggccg acaatatat gggtaatatt aatattactt tcacaccaag tagtcaaaca    1080
ctctag                                                              1086

<210> SEQ ID NO 110
<211> LENGTH: 534
<212> TYPE: DNA
<213> ORGANISM: Escherichia coli

<400> SEQUENCE: 110
atgttgaaaa gaatatcgtg tataattttt gttttttttt cagggctgat ttatgctgcg     60
gaaattacaa atcagataga gctttcggta aaggttaata tatctaagcc tatgtgtaaa    120
cttaattctg gaacgcaaac aatagacttc ggcgattttg atgtactgga tattattacg    180
gagaacagaa aattaaatgg tcatgcgacc tttaaattta ctgagtgtag ttctgtcaaa    240
aacatgaaga taaaatttaa acaggcagga caaaatccag cgttagatat cgtaaacaat    300
tatatcccta atagtaaggg agatagaatg caaagggggg tagcggtaaa gcttctggat    360
gataaaaagc aagaaattca actgaacaag gaaatgaatg ttattgtgga ggagagtctg    420
acatttaaag atttaacgtt aaatgctcag gttatctcta ttaataaaga cggagaggga    480
gtttcacctg gctacttca gaccgcaata ggaatggaga tatcctatga atga           534

<210> SEQ ID NO 111
<211> LENGTH: 1092
<212> TYPE: DNA
<213> ORGANISM: Escherichia coli

<400> SEQUENCE: 111
atgaaaaaga tatttatttt tttgtctatc atattttctg cggtggtcag tgccgggcga     60
tacccggaaa ctacagtagg taatctgacg aagagttttc aagcccctcg tcaggataga    120
agcgtacaat caccaatata taacatcttt acgaatcatg tggctggata tagtttgagt    180
cataacttat atgacaggat tgttttttta tgtacatcct cgtcgaatcc ggttaatggt    240
gcttgcccaa cccttggaac atctggagtt caatacggta ctacaaccat aaccttgcag    300
tttacagaaa aaagaagtct gataaaaaga atattaatc ttgcaggtaa taagaaacca    360
atatgggaga atcagagttg cgacactagc aatctaatgg tgttgaattc gaagtccttgg    420 tcctgtgggc attacggaaa tgctaacgga acacttctaa atctgtatat ccctgcagga    480
```

```
gaaatcaaca aattgccttt tgggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacct attcatctga atataatctt tataagatag ggggcactga aaaattacca    840
tatgctgttt cactgcttat gggagaaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttat ga                                                       1092

<210> SEQ ID NO 112
<211> LENGTH: 1092
<212> TYPE: DNA
<213> ORGANISM: Escherichia coli

<400> SEQUENCE: 112
atgaaaaaga tatttatttt tttgtctatc atattttctg cggtggtcag tgccgggcga     60
tacccggaaa ctacagtagg taatctgacg aagagttttc aagcccctcg tctggataga    120
agcgtacaat caccaatata taacatcttt acgaatcatg tggctggata tagtttgagt    180
catagattat atgacaggat tgttttttgta tgtacatcct cgtcgaatcc ggttaatggt    240
gcttgcccaa ccattggaac atctagagtt gaatacggta ctacaaccat aaccttgcag    300
tttacagaaa aaagagtcct gataaaaaga aatattaatc ttgcaggtaa taagaaacca    360
atatgggaga tcagagttg cgacactagc aatctaatgg tgttgaattc gaagtcttgg    420
tcctgtgggg ctctaggaaa tgctaacgga acacttctaa atctgtatat ccctgcagga    480
gaaatcaaca aattgccttt tgggagggata tgggaggcaa ctctgatctt acgcttatca    540
agatatggcg aagtcagtag cacccattac ggcaattata ccgtaaatat tacggttgat    600
ttaactgata aaggtaatat tcaggtatgg cttccagggt ttcacagcaa cccgcgtgta    660
gacctgaatc tgcaccctat cggtaattat aaatatagtg gtagtaattc actcgacatg    720
tgtttctatg atggatatag tacaaacagt gatagcatgg taataaagtt ccaggatgat    780
aatcctacca attcatctga atataatctt tataagatag ggggcactga aaaattacca    840
tatgctgttt cactgcttat gggaggaaaa atattttatc cagtgaatgg tcaatcattt    900
actatcaatg acagtagtgt actcgaaaca aactggaatc gagtaaccgc agttgctatg    960
ccggaagtta atgttccagt attatgctgg ccagcaagat tgctattaaa tgctgatgta   1020
aatgctcccg atgcaggaca gtattcagga cagatatata taacatttac acccagtgtc   1080
gaaaatttat ga                                                       1092

<210> SEQ ID NO 113
<211> LENGTH: 872
<212> TYPE: DNA
<213> ORGANISM: Escherichia coli

<400> SEQUENCE: 113
atgtcacatt ataaaacagg tcataaacaa ccacgatttc gttattcagt tctggcccgc     60
tgcgtggcgt gggcaaatat ctctgttcag gttcttttttc cactcgctgt caccttacc    120
```

```
ccagtaatgg cggcacgtgc gcagcatgcg gttcagccac ggttgagcat gggaaatact    180
acggtaactg ctgataataa cgtggagaaa aatgtcgcgt cgtttgccgc aaatgccggg    240
acatttttaa gcagtcagcc agatagcgat gcgacacgta actttattac cggaatggcc    300
acagctaaag ctaaccagga aatacaggag tggctcggga aatatggtac tgcgcgcgtc    360
aaactgaatg tcgataaaga tttctcgctg aaggattctt cgctggaaat gctttatccg    420
atttatgata cgccgacaaa tatgttgttc actcagggg  caatacatcg tacagacgat    480
cgtactcagt caaatattgg ttttggctgg cgtcattttt caggaaatga ctggatggcg    540
ggggtgaata cttttatcga tcatgattta tcccgtagtc atacccgcat ggtgttggt    600 gcggaatact ggcgcgatta tctgaaactg agcgccaatg gttatattcg ggcttctggc    660
tggaaaaaat cgccggatat tgaggattat caggaacgcc cggcgaatgg ctgggatatt    720
cgtgctgagg gctatttacc cgcctggccg cagcttggcg caagcctgat gtatgaacag    780
tattatggcg atgaagtcgg gctgtttggt aaagataagc gccagaaaga cccgcatgct    840
atttctgccg aggtgaccta tacgccagtg cc                                  872

<210> SEQ ID NO 114
<211> LENGTH: 33
<212> TYPE: DNA
<213> ORGANISM: Escherichia coli

<400> SEQUENCE: 114
atatccatgg ctatgtgtaa acttaattct gga                                 33

<210> SEQ ID NO 115
<211> LENGTH: 30
<212> TYPE: DNA
<213> ORGANISM: Escherichia coli

<400> SEQUENCE: 115
atctcggccg ctattgcggt ctgaagtagc                                     30

<210> SEQ ID NO 116
<211> LENGTH: 33
<212> TYPE: DNA
<213> ORGANISM: Escherichia coli

<400> SEQUENCE: 116
ttttccatgg gcatgaaaaa gatatttatt ttt                                 33

<210> SEQ ID NO 117
<211> LENGTH: 30
<212> TYPE: DNA
<213> ORGANISM: Escherichia coli

<400> SEQUENCE: 117
ggtgcggccg ttatatatat ctgtcctgaa                                     30

<210> SEQ ID NO 118
<211> LENGTH: 33
<212> TYPE: DNA
<213> ORGANISM: Escherichia coli

<400> SEQUENCE: 118
gtcaccatgg atatgacagg attgttttg tac                                  33

<210> SEQ ID NO 119
```

```
<211> LENGTH: 30
<212> TYPE: DNA
<213> ORGANISM: Escherichia coli

<400> SEQUENCE: 119
ggtgcggccg ttatatatat ctgtcctgaa                                      30

<210> SEQ ID NO 120
<211> LENGTH: 33
<212> TYPE: DNA
<213> ORGANISM: Escherichia coli

<400> SEQUENCE: 120
tttaccatgg taatggcggc acgtgcgcag cat                                  33

<210> SEQ ID NO 121
<211> LENGTH: 30
<212> TYPE: DNA
<213> ORGANISM: Escherichia coli

<400> SEQUENCE: 121
tttccggccg ttatctttac caaacagccc                                      30
```

ADHESIN TIP MULTIEPITOPE FUSION ANTIGEN PLATFORM AND VACCINES AND THEIR USE IN THE TREATMENT OF ENTEROTOXIGENIC DIARRHEA

This invention was made with government support under grant no. AI109209 awarded by The National Institutes of Health. The government has certain rights to the invention.

BACKGROUND OF THE INVENTION

Diarrhea continues to be a leading cause of death in children younger than 5 years who living in developing countries. Enterotoxigenic *Escherichia coli* (ETEC) is a leading bacterial cause of children's diarrhea and travelers' diarrhea. ETEC bacteria attaching host receptors at epithelial cells and colonizing in the small intestine initiate ETEC-associated diarrheal disease. Therefore, preventing ETEC attachment has been considered the first line of defense against ETEC diarrhea. However, ETEC strains produce over 23 immunologically heterogeneous adhesins, which makes developing vaccines that broadly protect against ETEC bacterial attachment challenging. Accordingly, what is needed is a composition that provides a protective effect against ETEC. What is further needed is a composition that induces antibody responses to multiple ETEC adhesins. What is also needed is a composition that impairs, reduces, or even prevents ETEC attachment.

SUMMARY OF THE INVENTION

The present disclosure overcomes the problems inherent in the prior art by applying a MEFA (multiepitope fusion antigen) approach to integrate epitopes from adhesin tips or adhesive subunits of CFA/I, CS1, CS2, CS3, CS4, CS5, CS6, CS21, EtpA, or other ETEC adhesins and to construct representative adhesin tip MEFA peptides (tip MEFA-I, tip MEFA-II), or epitopes from the major structural subunits of CS7, CS12, CS14, CS17, CS19, CS21, EtpA, and EaeH adhesins for a major subunit CFA MEFA (CFA MEFA-II). The antigenicity of each tip MEFA or the CFA MEFA was then examined in mouse immunization, and assessed for potential application for ETEC vaccine development. Data showed mice intraperitoneally immunized with ETEC adhesin tip MEFA-I developed IgG antibody responses to all nine ETEC adhesins (CFA/I, CS1-CS6, CS21, EtpA). Moreover, ETEC and *E. coli* bacteria expressing these nine adhesins, after incubation with serum of the immunized mice, had significant reduction of attachment to Caco-2 cells. Similarly, mice immunized with ETEC adhesin tip MEFA-II developed IgG antibodies against attachment of CS12, CS14, CS17, CS19 and EaeH, and mice immunized with major subunit CFA MEFA-II developed IgG antibodies against CS7, CS12, CS14, CS17, CS19, CS21, EtpA and EaeH adhesins. These results indicated that anti-adhesin antibodies induced by an adhesin tip MEFA or a CFA major subunit MEFA blocked adherence of the most important ETEC adhesins, suggesting that multivalent tip MEFA-I, tip MEFA-II, and the CFA MEFA-II can be useful for developing a broadly protective anti-adhesin vaccine against ETEC diarrhea.

Thus, the present disclosure utilizes an MEFA (multiepitope fusion antigen) approach to integrate epitopes from adhesin tips or adhesive subunits of CFA/I, CS1, CS2, CS3, CS4, CS5, CS6, CS21 CS7, CS12, CS14, CS17, CS19, EaeH, and EtpA adhesins to construct at least one adhesin tip MEFA peptide(s). Data showed mice intraperitoneally or subcutaneously immunized with an adhesin tip MEFA developed IgG antibody responses to all representing ETEC adhesins. Moreover, after incubation with serum of the immunized mice, ETEC and *E. coli* bacteria expressing these adhesins had significant reduction of attachment to Caco-2 cells. This MEFA approach was also used to integrate epitopes from the major structural subunits of CS7, CS12, CS14, CS17, CS19, CS21, EtpA and EaeH adhesins into a CFA major structural subunit MEFA (CFA MEFA-II). This CFA MEFA-II was then examined for immunogenicity in mouse immunization studies. Data showed that immunized mice developed strong IgG antibodies to each of eight target adhesins; moreover, the induced antibodies significantly reduced adherence of ETEC strains expressing each of these eight adhesins to Caco-2 cells. These results indicated that anti-adhesin antibodies induced by each adhesin tip MEFA or the CFA MEFA-II blocked adherence of the most important ETEC adhesins, suggesting the multivalent tip MEFA (tip MEFA-I, tip MEFA-II) or the major structural subunit MEFA (CFA MEFA-II) can be useful for developing a broadly protective anti-adhesin vaccine against ETEC diarrhea. "MEFA" refers to and encompasses both adhesin tip and major structural subunit MEFA.

The present disclosure provides for at least three, preferably, four, more preferably five, still more preferably six, even more preferably seven, still more preferably eight or more multi epitope fusion antigens (MEFA) comprising a nucleotide fragment encoding a polypeptide backbone from a colonization factor antigen (CFA) having epitopes from adhesin tips, adhesive subunits or major structural subunits of Enterotoxigenic *Escherichia coli* (ETEC) incorporated therein. In one embodiment, the epitopes from adhesin tips or adhesive subunits of ETEC are preferably selected from the group consisting of CFA/I, CS1, CS2, CS3, CS4, CS5, CS6, CS12, CS14, CS17, CS19, CS21, EtpA, EaeH, and any combination thereof. In one embodiment, there may be a single or multiple copies of each epitope present in the MEFA from the structural major subunits of CS7, CS12, CS14, CS17, CS19, CS21, EtpA and EaeH adhesins present in a MEFA.

In a further aspect, the present disclosure provides for an adhesin tip MEFA comprising nucleotides encoding a polypeptide backbone from a colonization factor antigen (CFA) having epitopes from adhesin tips or adhesive subunits of ETEC incorporated therein, wherein the backbone to which the epitopes are attached is preferably selected from, but not limited to, CfaE, CS14, and CS21. The present disclosure also provides for an adhesin major structural subunit CFA MEFA-II composing nucleotides encoding a polypeptide backbone from a colonization factor antigen (CFA) having epitopes from adhesin major structural subunits of CS7, CS12, CS14, CS17, CS19, CS21, EtpA, and EaeH ETEC adhesins incorporated therein.

The adhesin tip or major subunit MEFAs disclosed herein may further comprise additional elements, where such elements are selected from the group consisting of, but not limited to, heat liable toxin (LT), heat stable toxin (STa), an epitope from adhesin of enteroaggregative *E. coli* (EAEC), epitopes of cholera, epitopes of rotavirus, and any combination thereof. There may be one or more copies of LT and/or STa in any given adhesin tip MEFA of the present disclosure.

In one aspect, the present disclosure provides for a nucleic acid molecule that encodes for the polypeptide molecules described herein.

Further, the present disclosure provides for an expression vector comprising a nucleic acid molecule encoding the polypeptide molecules described herein.

In another aspect, the present disclosure provides for an immunogenic composition or vaccine composition comprising the polypeptide molecules described herein and a pharmaceutically acceptable vehicle, adjuvant, carrier and any combination thereof.

In a further aspect, a method of inducing an immune response against ETEC is provided. Preferably, the steps of the method include, but are not limited to, administration of one or more of the polypeptide(s) described herein to a human or animal in need thereof.

In yet another aspect, a method of reducing the severity or incidence of the clinical signs of ETEC infection is also provided in the present disclosure. The method of reducing the clinical signs of ETEC infection includes, but is not limited to, the step of administration of one or more the polypeptide(s) and/or adhesin tip MEFA(s) and/or CFA major subunit MEFA(s) disclosed herein to a human or animal in need thereof. The reduction in severity or incidence is in comparison to an animal or human, or group of animals or humans, that has not received an administration of one or more polypeptide(s) of the present disclosure.

Another aspect of the present disclosure includes a method of treating or reducing the incidence or severity of diarrhea. The method preferably comprises the steps of administration of one or more of the polypeptide(s) and/or adhesin tip MEFA(s) and/or CFA major subunit MEFA(s), as described herein, to a human or animal in need thereof. The treating or reducing the incidence or severity of diarrhea is in comparison to an animal or human, or group of animals or humans, that has not received an administration of one or more polypeptide(s) and/or adhesin tip MEFA(s) and/or CFA major subunit MEFA(s) of the present disclosure.

A method of reducing adherence of the ETEC bacteria to the intestine is also provided. The method preferably comprises the steps of administration of one or more of the polypeptide(s) and/or adhesion tip MEFA(s) and/or CFA major subunit MEFA(s) to a human or animal in need thereof. The adherence is in comparison to an animal or human, or group of animals or humans, that has not received an administration of one or more polypeptide(s) and/or adhesin tip MEFA(s) and/or CFA major subunit MEFA(s) of the present disclosure.

BRIEF DESCRIPTION OF THE DRAWINGS

The drawings described herein are for illustration purposes only and are not intended to limit the scope of the present teachings in any way.

DETAILED DESCRIPTION

Figure 1:
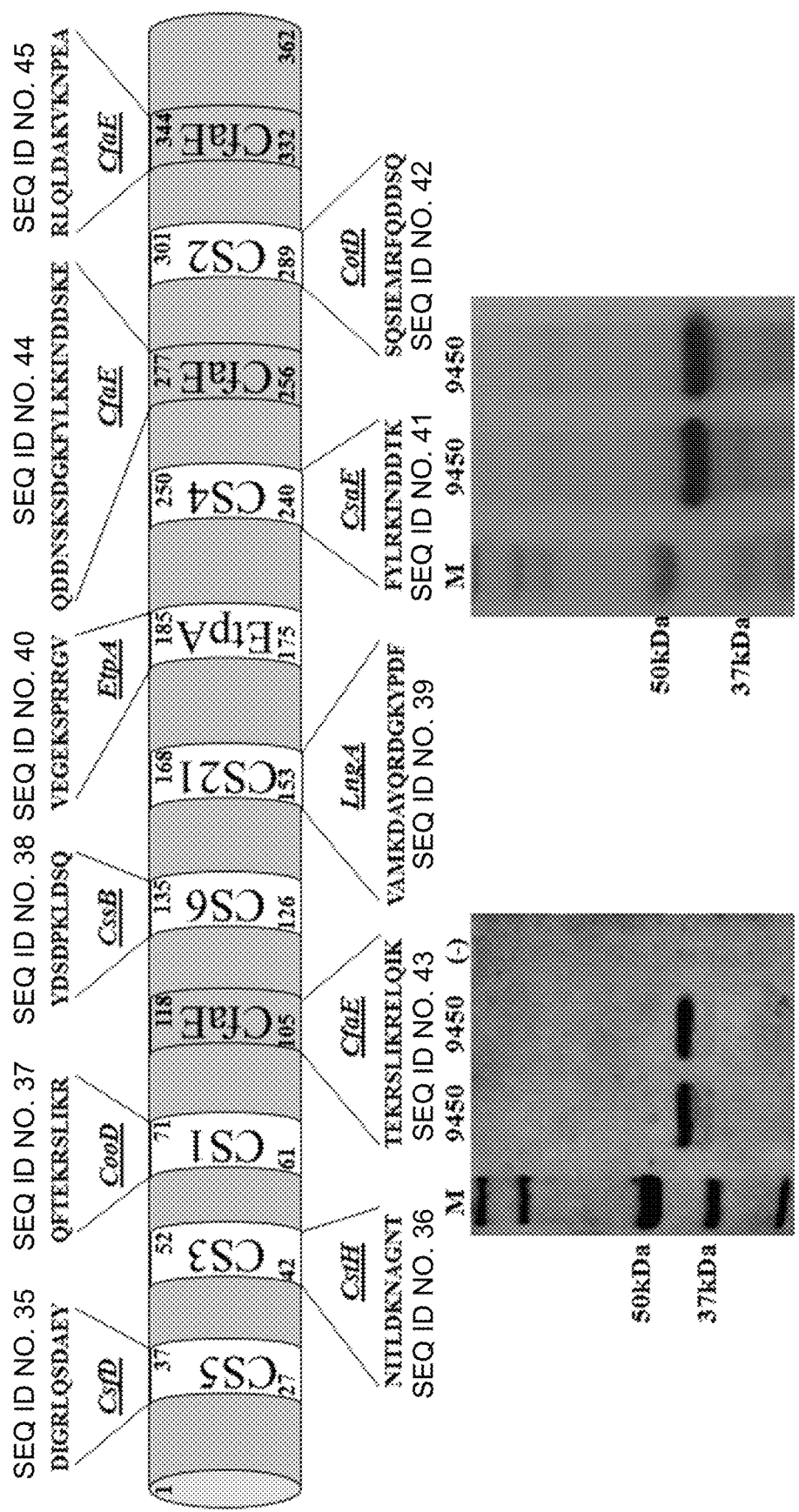
FIG. 1 is a schematic illustration of the constructed ETEC adhesin tip MEFA-I protein. Amino acid sequences of the epitopes from each adhesin tip or adhesive subunit are shown in the top panel. The bottom left panel shows results of Western blot with mouse anti-CFA/I antiserum, 9450 was the adhesin tip MEFA protein (25 and 30 µl), and (−) was the total proteins from BL21 $E.\ coli$. The bottom right panel showed Coomassie blue staining of refolded solubilized adhesin tip MEFA proteins (lane 1: protein marker; lane 2: 25 µl tip MEFA protein; lane 3: 30 µl tip MEFA protein)

The present disclosure provides for a multi epitope fusion antigen (MEFA) comprising a polypeptide including epitopes from adhesin tips or adhesive subunits of Enterotoxigenic $Escherichia\ coli$ (ETEC). In one embodiment, the epitopes from adhesin tips or adhesive subunits of ETEC are preferably selected from the group consisting of the adhesin tip or adhesive subunit of CFA/I, CS1, CS2, CS3, CS4, CS5, CS6, CS7, CS12, CS14, CS17, CS19, CS21, EtpA, EaeH and combinations thereof. In one embodiment, the polypeptide comprises at least 2 epitopes, at least 3 epitopes, at least 4 epitopes, at least 5 epitopes, at least 6 epitopes, at least 7 epitopes, at least 8 epitopes, at least 9 epitopes, at least 10 epitopes, at least 11 epitopes, at least 12 epitopes, at least 13 epitopes, at least 14 epitopes, and at least 15 epitopes.

The CS1 epitope for purposes of the present disclosure includes any nucleotide sequence or the amino acid sequence encoded by a nucleotide sequence that is associated with the CS1 genome from ETEC, including any fragment or portion thereof. The CS1 genome is preferably the nucleotide sequence encoding SEQ ID No. 47 or any sequence having at least 80%, at least 85%, at least 90%, or at least 95% sequence identity or homology with SEQ ID No. 47. In one embodiment, the CS1 epitope nucleotide sequence is generated from the primers selected from SEQ ID No. 3 and SEQ ID No. 4. One such preferred nucleotide sequence is SEQ ID No. 55. In an alternate embodiment, the CS1 epitope nucleotide sequence is selected from a sequence that has at least 80%, at least 85%, at least 90%, or at least 95% sequence identity or homology with a sequence generated from the primers selected from SEQ ID No. 3 and SEQ ID No. 4. Preferably, the CS1 epitope is an adhesin tip or adhesive subunit. In one embodiment, the epitope from CS1 is selected from the nucleotide sequence encoding SEQ ID No. 37 and a sequence that has at least 80%, at least 85%, at least 90%, or at least 95% sequence identity or homology with the nucleotide sequence encoding SEQ ID No. 37.

The CS2 epitope for purposes of the present disclosure includes any nucleotide sequence or the amino acid sequence encoded by the nucleotide sequence that is associated with the CS2 genome from ETEC, including any fragment or portion thereof. The CS2 genome is preferably the nucleotide sequence encoding SEQ ID No. 48 or any sequence having at least 80%, at least 85%, at least 90%, or at least 95% sequence identity or homology with SEQ ID No. 48. In one embodiment, the CS2 epitope nucleotide sequence is generated from the primers selected from SEQ ID No. 5 and SEQ ID No. 6. One such preferred nucleotide sequence is SEQ ID No. 56. In an alternate embodiment, the CS2 epitope is selected from a sequence that has at least 80%, at least 85%, at least 90%, or at least 95% sequence identity or homology with a sequence generated from the primers selected from SEQ ID No. 5 and SEQ ID No. 6. Preferably, the CS2 epitope is an adhesin tip or adhesive subunit. In one embodiment, the epitope from CS2 is selected from the nucleotide sequence encoding SEQ ID No. 42 and a sequence that has at least 80%, at least 85%, at least 90%, or at least 95% sequence identity or homology with the nucleotide sequence encoding SEQ ID No. 42.

The CS3 epitope for purposes of the present disclosure includes any nucleotide sequence or the amino acid sequence encoded by the nucleotide sequence that is associated with the CS3 genome from ETEC, including any fragment or portion thereof. The CS3 genome is preferably the nucleotide sequence encoding SEQ ID No. 49 or any sequence having at least 80%, at least 85%, at least 90%, or at least 95% sequence identity or homology with SEQ ID No. 49. In one embodiment, the CS3 epitope nucleotide sequence is generated from the primers selected from SEQ ID No. 7 and SEQ ID No. 8. One such preferred nucleotide sequence is SEQ ID No. 57. In an alternate embodiment, the CS3 epitope is selected from a sequence that has at least 80%, at least 85%, at least 90%, or at least 95% sequence identity or homology with a sequence generated from the primers selected from SEQ ID No. 7 and SEQ ID No. 8. Preferably, the CS3 epitope is an adhesin tip or adhesive subunit. In one embodiment, the epitope from CS3 is selected from the nucleotide sequence encoding SEQ ID No. 36 and a sequence that has at least 80%, at least 85%, at least 90%, or at least 95% sequence identity or homology with the nucleotide sequence encoding SEQ ID No. 36.

The CS4 epitope for purposes of the present disclosure includes any nucleotide sequence or the amino acid sequence encoded by the nucleotide sequence that is associated with the CS4 genome from ETEC, including any fragment or portion thereof. The CS4 genome is preferably the nucleotide sequence encoding SEQ ID No. 50 or any sequence having at least 80%, at least 85%, at least 90%, or at least 95% sequence identity or homology with SEQ ID No. 50. In one embodiment, the CS4 epitope nucleotide sequence is generated from the primers selected from SEQ ID No. 9 and SEQ ID No. 10. One such preferred nucleotide sequence is SEQ ID No. 58. In an alternate embodiment, the CS4 epitope is selected from a sequence that has at least 80%, at least 85%, at least 90%, or at least 95% sequence identity or homology with a sequence generated from the primers selected from SEQ ID No. 9 and SEQ ID No. 10. Preferably, the CS4 epitope is an adhesin tip or adhesive subunit. In one embodiment, the epitope from CS4 is selected from the nucleotide sequence encoding SEQ ID No. 41 and a sequence that has at least 80%, at least 85%, at least 90%, or at least 95% sequence identity or homology with the nucleotide sequence encoding SEQ ID No. 41.

The CS5 epitope for purposes of the present disclosure includes any nucleotide sequence or the amino acid sequence encoded by the nucleotide sequence that is associated with the CS5 genome from ETEC, including any fragment or portion thereof. The CS5 genome is preferably the nucleotide sequence encoding SEQ ID No. 51 or any sequence having at least 80%, at least 85%, at least 90%, or at least 95% sequence identity or homology with SEQ ID No. 51. In one embodiment, the CS5 epitope nucleotide sequence is generated from the primers selected from SEQ ID No. 11 and SEQ ID No. 12. One such preferred nucleotide sequence is SEQ ID No. 59. In an alternate embodiment, the CS5 epitope is selected from a sequence that has at least 80%, at least 85%, at least 90%, or at least 95% sequence identity or homology with a sequence generated from the primers selected from SEQ ID No. 11 and SEQ ID No. 12. Preferably, the CS5 epitope is an adhesin tip or adhesive subunit. In one embodiment, the epitope from CS5 is selected from the nucleotide sequence encoding SEQ ID No. 35 and a sequence that has at least 80%, at least 85%, at least 90%, or at least 95% sequence identity or homology with the nucleotide sequence encoding SEQ ID No. 35.

The CS6 epitope for purposes of the present disclosure includes any nucleotide sequence or the amino acid sequence encoded by the nucleotide sequence that is associated with the CS6 genome from ETEC, including any fragment or portion thereof. The CS6 genome is preferably the nucleotide sequence encoding SEQ ID No. 52 or any sequence having at least 80%, at least 85%, at least 90%, or at least 95% sequence identity or homology with SEQ ID No. 52. In one embodiment, the CS6 epitope nucleotide sequence is generated from the primers selected from SEQ ID No. 15 and SEQ ID No. 16. One such preferred nucleotide sequence is SEQ ID No. 60 or any sequence having at least 80%, at least 85%, at least 90%, or at least 95% sequence identity or homology with SEQ ID No. 60.

In an alternate embodiment, the CS6 epitope is selected from a sequence that has at least 80%, at least 85%, at least 90%, or at least 95% sequence identity or homology with a sequence generated from the primers selected from SEQ ID No. 13 and SEQ ID No. 14. Preferably, the CS6 epitope is an adhesin tip or adhesive subunit. In one embodiment, the epitope from CS6 is selected from the nucleotide sequence encoding SEQ ID No. 38 and a sequence that has at least 80%, at least 85%, at least 90%, or at least 95% sequence identity or homology with the nucleotide sequence encoding SEQ ID No. 38.

The CS21 epitope for purposes of the present disclosure includes any nucleotide sequence or the amino acid sequence encoded by the nucleotide sequence that is associated with the CS21 genome from ETEC, including any fragment or portion thereof. The CS21 genome is preferably the nucleotide sequence encoding SEQ ID No. 53 or any sequence having at least 80%, at least 85%, at least 90%, or at least 95% sequence identity or homology with SEQ ID No. 53. In one embodiment, the CS21 epitope nucleotide sequence is generated from the primers selected from SEQ ID No. 15 and SEQ ID No. 16. One such preferred nucleotide sequence is SEQ ID No. 61. In an alternate embodiment, the CS21 epitope is selected from a sequence that has at least 80%, at least 85%, at least 90%, or at least 95% sequence identity or homology with a sequence generated from the primers selected from SEQ ID No. 15 and SEQ ID No. 16. Preferably, the CS21 epitope is an adhesin tip or adhesive subunit. In one embodiment, the epitope from CS21 is selected from the nucleotide sequence encoding SEQ ID No. 39 and a sequence that has at least 80%, at least 85%, at least 90%, or at least 95% sequence identity or homology with the nucleotide sequence encoding SEQ ID No. 39.

The EtpA epitope for purposes of the present disclosure includes any nucleotide sequence or the amino acid sequence encoded by the nucleotide sequence that is associated with the EtpA genome from ETEC, including any fragment or portion thereof. The EtpA genome is preferably the nucleotide sequence encoding SEQ ID No. 2 or any sequence having at least 80%, at least 85%, at least 90%, or at least 95% sequence identity or homology with SEQ ID No. 2. In one embodiment, the EtpA epitope nucleotide sequence is generated from the primers selected from SEQ ID No. 17 and SEQ ID No. 34. One such preferred nucleotide sequence is SEQ ID No. 62. In an alternate embodiment, the EtpA epitope is selected from a sequence that has at least 80%, at least 85%, at least 90%, or at least 95% sequence identity or homology with a sequence generated from the primers selected from SEQ ID No. 17 and SEQ ID No. 34. Preferably, the EtpA epitope is an adhesin tip or adhesive subunit. In one embodiment, the epitope from EtpA is selected from the nucleotide sequence encoding SEQ ID No. 40 and a sequence that has at least 80%, at least 85%, at least 90%, or at least 95% sequence identity or homology with the nucleotide sequence encoding SEQ ID No. 40.

The CS7 epitope for purposes of the present disclosure includes any nucleotide sequence or the amino acid sequence encoded by the nucleotide sequence that is associated with the CS7 genome from ETEC, including any fragment or portion thereof. In one embodiment, the CS7 epitope is selected from the nucleic acid sequence encoding SEQ ID No. 22 and/or the nucleic acid sequence encoding SEQ ID No. 29 and/or the nucleic acid sequence encoding SEQ Id NO. 68. In an alternate embodiment, the CS7 epitope is selected from a sequence that has at least 80%, at least 85%, at least 90%, or at least 95% sequence identity or homology with either the nucleic acid sequence encoding SEQ ID No. 22 and/or the nucleic acid sequence encoding SEQ ID No. 29 and/or the nucleic acid sequence encoding SEQ Id NO. 68. In another alternate embodiment, the CS7 epitope is selected from a sequence that has at least 80%, at least 85%, at least 90%, or at least 95% sequence identity or homology with SEQ ID No. 22 and/or SEQ ID No. 29 and/or the nucleic acid sequence encoding SEQ Id NO. 68. Preferably, the CS7 epitope is an adhesin tip or adhesive subunit.

The CS12 epitope for purposes of the present disclosure includes any nucleotide sequence or the amino acid sequence encoded by the nucleotide sequence that is associated with the CS12 genome from ETEC, including any fragment or portion thereof. In one embodiment, the CS12 epitope is selected from the nucleic acid sequence encoding SEQ ID No. 24 and/or the nucleic acid sequence encoding SEQ ID No. 30 and/or the nucleic acid sequence encoding SEQ Id NO. 69. In an alternate embodiment, the CS12 epitope is selected from a sequence that has at least 80%, at least 85%, at least 90%, or at least 95% sequence identity or homology with either the nucleic acid sequence encoding SEQ ID No. 24 or the nucleic acid sequence encoding SEQ ID No. 30 and/or the nucleic acid sequence encoding SEQ Id NO. 69. In another alternate embodiment, the CS12 epitope is selected from a sequence that has at least 80%, at least 85%, at least 90%, or at least 95% sequence identity or homology with SEQ ID No. 24 and/or SEQ ID No. 30 and/or the nucleic acid sequence encoding SEQ Id NO. 69. Preferably, the CS12 epitope is an adhesin tip or adhesive subunit.

The CS14 epitope for purposes of the present disclosure includes any nucleotide sequence or the amino acid sequence encoded by the nucleotide sequence that is associated with the CS14 genome from ETEC, including any fragment or portion thereof. In one embodiment, the CS14 epitope is selected from the nucleic acid sequence encoding SEQ ID No. 21, and/or the nucleic acid sequence encoding SEQ ID No. 23, and/or the nucleic acid sequence encoding SEQ ID No. 26 and/or the nucleic acid sequence encoding SEQ Id NO. 70. In an alternate embodiment, the CS14 epitope is selected from a sequence that has at least 80%, at least 85%, at least 90%, or at least 95% sequence identity or homology with one or more of the nucleic acid sequence encoding SEQ ID No. 21, the nucleic acid sequence encoding SEQ ID No. 23, and the nucleic acid sequence encoding SEQ ID No. 26 and/or the nucleic acid sequence encoding SEQ Id NO. 70. In another alternate embodiment, the CS14 epitope is selected from a sequence that has at least 80%, at least 85%, at least 90%, or at least 95% sequence identity or homology with SEQ ID No. 21, SEQ ID No. 23, and/or SEQ ID No. 26 and/or the nucleic acid sequence encoding SEQ Id NO. 70. Preferably, the CS14 epitope is an adhesin tip or adhesive subunit.

The CS17 epitope for purposes of the present disclosure includes any nucleotide sequence or the amino acid sequence encoded by the nucleotide sequence that is associated with the CS17 genome from ETEC, including any fragment or portion thereof. In one embodiment, the CS17 epitope is selected from the nucleotide sequence encoding SEQ ID No. 25 and/or the nucleotide sequence encoding SEQ ID No. 31 and/or the nucleic acid sequence encoding SEQ ID NO. 71. In an alternate embodiment, the CS17 epitope is selected from a sequence that has at least 80%, at least 85%, at least 90%, or at least 95% sequence identity or homology with either the nucleotide sequence encoding SEQ ID No. 25 or the nucleotide sequence encoding SEQ ID No. 31 and/or the nucleic acid sequence encoding SEQ ID NO. 71. In another alternate embodiment, the CS17 epitope is selected from a sequence that has at least 80%, at least 85%, at least 90%, or at least 95% sequence identity or homology with SEQ ID No. 25 and/or SEQ ID No. 31 and/or the nucleic acid sequence encoding SEQ ID NO. 71. Preferably, the CS17 epitope is an adhesin tip or adhesive subunit.

The CS19 epitope for purposes of the present disclosure includes any nucleotide sequence or the amino acid sequence encoded by the nucleotide sequence that is associated with the CS19 genome from ETEC, including any fragment or portion thereof. In one embodiment, the CS19 epitope is selected from the nucleotide sequence encoding SEQ ID No. 27 and/or the nucleotide sequence encoding SEQ ID No. 32 and/or the nucleic acid sequence encoding SEQ ID NO. 72. In an alternate embodiment, the CS19 epitope is selected from a sequence that has at least 80%, at least 85%, at least 90%, or at least 95% sequence identity or homology with either the nucleotide sequence encoding SEQ ID No. 27 or the nucleotide sequence encoding SEQ ID No. 32 and/or the nucleic acid sequence encoding SEQ ID NO. 72. In another alternate embodiment, the CS19 epitope is selected from SEQ ID No. 27 and/or SEQ ID No. 32 and/or the nucleic acid sequence encoding SEQ ID NO. 72. Preferably, the CS19 epitope is an adhesin tip or adhesive subunit.

The EaeH epitope for purposes of the present disclosure includes any nucleotide sequence or the amino acid sequence encoded by the nucleotide sequence that is associated with the EaeH genome from ETEC, including any fragment or portion thereof. In one embodiment, the EaeH epitope is selected from the nucleotide sequence encoding SEQ ID No. 28 and/or the nucleotide sequence encoding SEQ ID No. 33 and/or the nucleic acid sequence encoding SEQ ID NO. 73. In an alternate embodiment, the EaeH epitope is selected from a sequence that has at least 80%, at least 85%, at least 90%, or at least 95% sequence identity or homology with either the nucleotide sequence encoding SEQ ID No. 28 and/or the nucleotide sequence encoding SEQ ID No. 33 and/or the nucleic acid sequence encoding SEQ ID NO. 73. In an alternate embodiment, the EaeH epitope is selected from a sequence that has at least 80%, at least 85%, at least 90%, or at least 95% sequence identity or homology with SEQ ID No. 28 and/or SEQ ID No. 33 and/or the nucleic acid sequence encoding SEQ ID NO. 73. Preferably, the EaeH epitope is an adhesin tip or adhesive subunit.

In a further aspect, the present disclosure provides for an adhesin tip MEFA comprising a polypeptide encoding epitopes from adhesion tips or adhesive subunits of ETEC, wherein the polypeptide encodes a colonization factor antigen (CFA) backbone to which the epitopes are attached. The backbone is preferably selected from, but not limited to, CfaE, CfaA, CfaB, CfaC, CS14, CS7, CS12, CS17, CS19, CS21, and combinations thereof. In a particularly preferred embodiment, the backbone is selected from CfaE, CS14, and CS21.

The CfaE backbone for purposes of the present disclosure includes any nucleotide sequence or amino acid sequence or the product produced by the nucleotide sequence associated with the CfaE genome from ETEC, including any fragment or portion thereof. In one embodiment, the CfaE backbone is selected from the sequence generated by the primers SEQ ID No. 18 and SEQ ID No. 19. In an alternate embodiment, the CfaE backbone is selected from a sequence that has at least 80%, at least 85%, at least 90%, or at least 95% sequence identity or homology with a sequence generated by the primers SEQ ID No. 18 and SEQ ID No. 19. In some preferred forms, the CfaE backbone has at least 80%, at least 85%, at least 90%, or at least 95% sequence identity or homology with SEQ ID No. 46. In another embodiment, the amino acid sequence of the CfaE backbone is SEQ ID No. 46. In a further embodiment, the CfaE backbone retains one or more epitopes of CfaE. Such CfaE epitopes are preferably selected from the nucleotide sequence encoding SEQ ID No. 43, the nucleotide sequence encoding SEQ ID No. 44, the nucleotide sequence encoding SEQ ID No. 45, and sequences having at least 80%, at least 85%, at least 90%, or at least 95% sequence identity or homology with the nucleotide sequence encoding SEQ ID No. 43, SEQ ID NO. 44, or SEQ ID No. 45.

In a further aspect, the present disclosure provides for an adhesin major subunit MEFA of CS21 comprising a polypeptide encoding epitopes from adhesion tips or adhesive subunits of CS7, CS12, CS14, CS17, CS19, EtpA, and EaeH, wherein the polypeptide encodes a colonization factor antigen (CFA) backbone to which the epitopes are attached. In a preferred aspect, the CS21 backbone retains two epitopes.

The CS14 backbone for purposes of the present disclosure includes any nucleotide sequence or amino acid sequence or the product produced by the nucleotide sequence associated with the CS14 genome from ETEC, including any fragment or portion thereof. In one embodiment, the CS14 backbone is selected from the nucleotide sequence encoding SEQ ID No. 21 and a sequence that has at least 80%, at least 85%, at least 90%, or at least 95% sequence identity or homology with the nucleotide sequence encoding SEQ ID No. 21. In an alternative embodiment, the CS14 backbone is selected from the a sequence that has at least 80%, at least 85%, at least 90%, or at least 95% sequence identity or homology with SEQ ID No. 21. In a further embodiment, the CS14 backbone retains one or more epitopes of CS14. Such CS14 epitopes are preferably selected from the nucleotide sequence encoding SEQ ID No. 23, the nucleotide sequence encoding SEQ ID No. 26, and sequences having at least 80%, at least 85%, at least 90%, or at least 95% sequence identity or homology with the nucleotide sequence encoding SEQ ID No. 23 or SEQ ID No. 26.

The CS7 backbone for purposes of the present disclosure includes any nucleotide sequence or amino acid sequence that is associated with the CS7 genome from ETEC, including any fragment or portion thereof. In one embodiment, the CS7 backbone is selected from the nucleotide sequence encoding SEQ ID No. 29 and/or a sequence that has at least 80%, at least 85%, at least 90%, or at least 95% sequence identity or homology with a nucleotide sequence encoding SEQ ID No. 29. In an alternative embodiment, the CS7 backbone is selected from the a sequence that has at least 80%, at least 85%, at least 90%, or at least 95% sequence identity or homology with SEQ ID No. 29.

The CS12 backbone for purposes of the present disclosure includes any nucleotide sequence or amino acid sequence that is associated with the CS12 genome from ETEC, including any fragment or portion thereof. In one embodiment, the CS12 backbone is selected from the nucleotide sequence encoding SEQ ID No. 30 and/or a sequence that has at least 80%, at least 85%, at least 90%, or at least 95% sequence identity or homology with the nucleotide sequence encoding SEQ ID No. 30. In an alternative embodiment, the CS12 backbone is selected from the a sequence that has at least 80%, at least 85%, at least 90%, or at least 95% sequence identity or homology with SEQ ID No. 30.

The CS17 backbone for purposes of the present disclosure includes any nucleotide sequence or amino acid that is associated with the CS17 genome from ETEC, including any fragment or portion thereof. In one embodiment, the CS17 backbone is selected from the nucleotide sequence encoding SEQ ID No. 31 and/or a sequence that has at least 80%, at least 85%, at least 90%, or at least 95% sequence identity or homology with the nucleotide sequence encoding SEQ ID No. 31. In an alternative embodiment, the CS17 backbone is selected from the a sequence that has at least 80%, at least 85%, at least 90%, or at least 95% sequence identity or homology with SEQ ID No. 31.

The CS19 backbone for purposes of the present disclosure includes any nucleotide sequence or amino acid sequence that is associated with the CS19 genome from ETEC, including any fragment or portion thereof. In one embodiment, the CS19 backbone is selected from the nucleotide sequence encoding SEQ ID No. 21 and/or a sequence that has at least 80%, at least 85%, at least 90%, or at least 95% sequence identity or homology with the nucleotide sequence encoding SEQ ID No. 32. In an alternative embodiment, the CS19 backbone is selected from the a sequence that has at least 80%, at least 85%, at least 90%, or at least 95% sequence identity or homology with SEQ ID No. 32.

The adhesin tip MEFAs disclosed herein may further comprise additional elements, where such elements are selected from, but not limited to, heat liable toxin (LT), heat stable toxin (STa), epitopes from adhesin of enteroaggregative E. coli (EAEC), epitopes of cholera, epitopes of rotavirus and any combination thereof. In one embodiment, there may be one or more copies of LT, STa, and any combination thereof.

For purposes of the present invention, the adhesin tip MEFA may be comprised of any nucleotide encoding the backbone of a CFA from ETEC having at least one of the epitopes from ETEC inserted therein. One non-limiting example of such an adhesin tip MEFA is the nucleotide sequence of SEQ ID No. 1 or the amino acid sequence of SEQ ID No. 20, however, the disclosure is not so limited as those of skill in the art can appreciate that many combinations are possible. In one embodiment, the complete adhesin tip MEFA of the present invention is a sequence that is at least 80%, at least 85% at least 90%, at least 95%, or 100% identical to the nucleotide sequence of SEQ ID No. 1 or the amino acid sequence of SEQ ID No. 20. In another embodiment, the complete adhesin tip MEFA of the present invention is a sequence that is at least 80%, at least 85% at least 90%, at least 95%, or 100% identical to the nucleotide sequence of SEQ ID No. 63 or the amino acid sequence of SEQ ID No. 64. In another embodiment, the complete adhesin tip MEFA of the present invention is a sequence that is at least 80%, at least 85% at least 90%, at least 95%, or 100% identical to the nucleotide sequence of SEQ ID No. 65 or the amino acid sequence of SEQ ID No. 66.

In one aspect, the present disclosure provides for a nucleic acid molecule that encodes for the polypeptide molecules described herein.

Further, the present disclosure provides for an expression vector comprising the nucleic acid molecule encoding the polypeptide molecules described herein. The expression vector is preferably selected from, but not limited to, *E. coli, Salmonella*, and combinations thereof.

The *E. coli* preferably used for purposes of the present disclosure is selected from, but not limited to, H10407, THK/38/pEU405, DH5α/pEU588. E116 (E19446), E106 (E11881/9), UM 75688, JF2423 ETP98066, JF2101, JF2318 ETP050008, CFA/I knockout, 9573, 9474, 9475, 9505, 9504, 9533, 9506, 9468, 9507, 9450, and any combination thereof.

In another aspect, the present disclosure provides for an immunogenic composition or vaccine composition comprising one or more of the adhesin tip MEFAs encoding polypeptide molecules described herein and a pharmaceutically acceptable vehicle. The one or more polypeptide molecules may be multiple copies of the same polypeptide or more than one polypeptide, each having a different structure. It is appreciated that there are many combinations of adhesin tip MEFAs encoding polypeptide molecules that may be present in an immunogenic composition or vaccine.

In one embodiment, the immunogenic composition or vaccine disclosed herein comprises an adhesin tip MEFA comprising a polypeptide encoding for a backbone, preferably the CfaE backbone, having the epitopes for CS1, CS2, CS3, CS4, CS5, CS6, CS21, and EtpA.

In a further embodiment, the immunogenic composition or vaccine disclosed herein comprises an adhesin tip MEFA comprising a polypeptide encoding for a backbone, preferably the CS14 backbone, having the epitopes for CS7, CS12, CS17, CS14, CS19, and EaeH.

In yet another embodiment, the immunogenic composition or vaccine disclosed herein comprises two adhesin tip MEFAs. It is appreciated that any combination of a plurality of backbones with different epitopes thereon is contemplated in the present disclosure. In one preferred embodiment, the first adhesin tip MEFA comprises a polypeptide encoding for a CfaE backbone having the epitopes for CS1, CS2, CS3, CS4, CS5, CS6, CS21, and EtpA; and the second adhesin tip MEFA comprises a polypeptide encoding for a CS14 backbone having the epitopes for CS7, CS12, CS17, CS14, CS19, and EaeH.

The immunogenic composition of the present disclosure may further comprise a preservative, stabilizer, carrier, adjuvant, and/or pharmaceutical vehicle. "Adjuvants" as used herein, can include aluminum hydroxide and aluminum phosphate, saponins e.g., Quil A, QS-21 (Cambridge Biotech Inc., Cambridge Mass.), GPI-0100 (Galenica Pharmaceuticals, Inc., Birmingham, Ala.), water-in-oil emulsion, oil-in-water emulsion, water-in-oil-in-water emulsion. The emulsion can be based in particular on light liquid paraffin oil (European Pharmacopea type); isoprenoid oil such as squalane or squalene; oil resulting from the oligomerization of alkenes, in particular of isobutene or decene; esters of acids or of alcohols containing a linear alkyl group, more particularly plant oils, ethyl oleate, propylene glycol di-(caprylate/caprate), glyceryl tri-(caprylate/caprate) or propylene glycol dioleate; esters of branched fatty acids or alcohols, in particular isostearic acid esters. The oil is used in combination with emulsifiers to form the emulsion. The emulsifiers are preferably nonionic surfactants, in particular esters of sorbitan, of mannide (e.g. anhydromannitol oleate), of glycol, of polyglycerol, of propylene glycol and of oleic, isostearic, ricinoleic or hydroxystearic acid, which are optionally ethoxylated, and polyoxypropylene-polyoxyethylene copolymer blocks, in particular the Pluronic products, especially L121. See Hunter et al., The Theory and Practical Application of Adjuvants (Ed. Stewart-Tull, D. E. S.). John Wiley and Sons, NY, pp 51-94 (1995) and Todd et al., Vaccine 15:564-570 (1997).

For example, it is possible to use the SPT emulsion described on page 147 of "Vaccine Design, The Subunit and Adjuvant Approach" edited by M. Powell and M. Newman, Plenum Press, 1995, and the emulsion MF59 described on page 183 of this same book.

A further instance of an adjuvant is a compound chosen from the polymers of acrylic or methacrylic acid and the copolymers of maleic anhydride and alkenyl derivative. Advantageous adjuvant compounds are the polymers of acrylic or methacrylic acid which are cross-linked, especially with polyalkenyl ethers of sugars or polyalcohols. These compounds are known by the term carbomer (*Pharmeuropa* Vol. 8, No. 2, June 1996). Persons skilled in the art can also refer to U.S. Pat. No. 2,909,462 which describes such acrylic polymers cross-linked with a polyhydroxylated compound having at least 3 hydroxyl groups, preferably not more than 8, the hydrogen atoms of at least three hydroxyls being replaced by unsaturated aliphatic radicals having at least 2 carbon atoms. The preferred radicals are those containing from 2 to 4 carbon atoms, e.g. vinyls, allyls and other ethylenically unsaturated groups. The unsaturated radicals may themselves contain other substituents, such as methyl. The products sold under the name Carbopol; (BF Goodrich, Ohio, USA) are particularly appropriate. They are cross-linked with an allyl sucrose or with allyl pentaerythritol. Among then, there may be mentioned Carbopol 974P, 934P and 971P. Most preferred is the use of Carbopol 971P. Among the copolymers of maleic anhydride and alkenyl derivative, the copolymers EMA (Monsanto) which are copolymers of maleic anhydride and ethylene. The dissolution of these polymers in water leads to an acid solution that will be neutralized, preferably to physiological pH, in order to give the adjuvant solution into which the immunogenic, immunological or vaccine composition itself will be incorporated.

Further suitable adjuvants include, but are not limited to, the RIBI adjuvant system (Ribi Inc.), Block co-polymer (CytRx, Atlanta Ga.), SAF-M (Chiron, Emeryville Calif.), monophosphoryl lipid A, Avridine lipid-amine adjuvant, heat-labile enterotoxin from *E. coli* (recombinant or otherwise), cholera toxin, IMS 1314 or muramyl dipeptide among many others. Most preferably, heat-labile enterotoxin mutants are used as the adjuvant.

In a further aspect, a method of inducing an immune response against ETEC is provided. Preferably, the steps of the method include, but are not limited to, administration of one or more of the polypeptide(s) described herein to a human or animal in need thereof.

A method of reducing the incidence of or severity of clinical signs of ETEC infection is also provided in the present disclosure. The method of reducing the incidence or severity clinical signs of ETEC infection includes, but is not limited to, the step of administration of one or more the polypeptide(s) disclosed herein to a human or animal in need thereof. In one embodiment, the severity or incidence of clinical signs of ETEC are reduced by at least 10%, at least 20%, at least 30%, at least 40%, at least 50%, at least 60%, at least 70%, at least 80%, at least 90%, and 100% when compared to a human or animal, or group of humans or animals not having received the adhesin tip MEFA. The MEFA is preferably administered in an amount of less than 50 micrograms, where values such as 1-30 micrograms, 10-30 micrograms, 10-20 micrograms, 10-50 micrograms, 20-50 micrograms, 30-50 micrograms, 40-50 micrograms, 1 microgram, 5 micrograms, 10 micrograms, 15 micrograms, 20 micrograms, 25 micrograms, 30 micrograms, 35 micrograms, 40 micrograms, 45 micrograms, and 50 micrograms are envisioned. The route of administration is preferably selected from intradermal, intramuscular, or subcutaneous immunization.

A method of treating or reducing the incidence or severity of diarrhea is also provided in the present disclosure. The method preferably comprises the steps of administration of one or more of the adhesin tip MEFA(s) of the present disclosure to a human or animal, or group of humans or animals in need thereof. In one embodiment, diarrhea incidence or severity is reduced by at least 10%, at least 20%, at least 30%, at least 40%, at least 50%, at least 60%, at least 70%, at least 80%, at least 90%, and 100% when compared to a human or animal, or group of humans or animals not having received the administration of the adhesin tip MEFA.

A method of reducing the adhesion of ETEC to the gut is also provided by the present disclosure. The method preferably comprises the steps of administration of one of more of the adhesin tip MEFA(s) of the present disclosure to a human or animal in need thereof. In one embodiment, adhesion to the gut is reduced by at least 10%, at least 20%, at least 30%, at least 40%, at least 50%, at least 60%, at least 70%, at least 80%, at least 90%, and 100% when compared to a human or animal not having received the adhesin tip MEFA As used herein "multiepitope fusion antigen" (MEFA) refers to a molecule that is created by combining the fusion and epitope strategies for making vaccines or immunogenic compositions. The method of producing an MEFA allows for use of a backbone molecule and the addition of any antigenic element or identified virulence factors, as well as additional elements. In the present disclosure, the MEFA may have a single copy or multiple copies of any one component. The "adhesin tip MEFA" means that the MEFA is created using the "tip" or end of the genome or a subunit that is on the "tip" of the gene.

The "adhesin tip" for purposes of the present disclosure refers to a subunit protein located at the tip of an ETEC bacteria adhesion.

For purposes of the present disclosure, "adhesive subunit" refers to a subunit protein of ETEC adhesion which is not located at the tip, but is involved in bacterial adherence to host receptors.

For purposes of the present disclosure, "sequence identity" refers to a relationship between two or more polypeptide sequences or two or more polynucleotide sequences, namely a reference sequence and a given sequence to be compared with the reference sequence. Sequence identity is determined by comparing the given sequence to the reference sequence after the sequences have been optimally aligned to produce the highest degree of sequence similarity, as determined by the match between strings of such sequences. Upon such alignment, sequence identity is ascertained on a position-by-position basis, e.g., the sequences are "identical" at a particular position if at that position, the nucleotides or amino acid residues are identical. The total number of such position identities is then divided by the total number of nucleotides or residues in the reference sequence to give % sequence identity. Sequence identity can be readily calculated by known methods, including but not limited to, those described in Computational Molecular Biology, Lesk, A. N., ed., Oxford University Press, New York (1988), Biocomputing: Informatics and Genome Projects, Smith, D. W., ed., Academic Press, New York (1993); Computer Analysis of Sequence Data, Part I, Griffin, A. M., and Griffin, H. G., eds., Humana Press, New Jersey (1994); Sequence Analysis in Molecular Biology, von Heinge, G., Academic Press (1987); Sequence Analysis Primer, Gribskov, M. and Devereux, J., eds., M. Stockton Press, New York (1991); and Carillo, H., and Lipman, D., SIAM J. Applied Math., 48: 1073 (1988), the teachings of which are incorporated herein by reference. Preferred methods to determine the sequence identity are designed to give the largest match between the sequences tested. Methods to determine sequence identity are codified in publicly available computer programs which determine sequence identity between given sequences. Examples of such programs include, but are not limited to, the GCG program package (Devereux, J., et al., Nucleic Acids Research, 12(1):387 (1984)), BLASTP, BLASTN and FASTA (Altschul, S. F. et al., J. Molec. Biol., 215:403-410 (1990). The BLASTX program is publicly available from NCBI and other sources (BLAST Manual, Altschul, S. et al., NCVI NLM NIH Bethesda, Md. 20894, Altschul, S. F. et al., J. Molec. Biol., 215:403-410 (1990), the teachings of which are incorporated herein by reference). These programs optimally align sequences using default gap weights in order to produce the highest level of sequence identity between the given and reference sequences.

For purposes of the present disclosure, "sequence homology refers to a method of determining the relatedness of two sequences. To determine sequence homology, two or more sequences are optimally aligned, and gaps are introduced if necessary. However, in contrast to "sequence identity", conservative amino acid substitutions are counted as a match when determining sequence homology. In other words, to obtain a polypeptide or polynucleotide having 95% sequence homology with a reference sequence, 85%, preferably 90%, even more preferably 95% of the amino acid residues or nucleotides in the reference sequence must match or comprise a conservative substitution with another amino acid or nucleotide, or a number of amino acids or nucleotides up to 15%, preferably up to 10%, even more preferably up to 5% of the total amino acid residues or nucleotides, not including conservative substitutions, in the reference sequence may be inserted into the reference sequence.

For purposes of the present disclosure, "epitope" refers to a short peptide which functions as an antigen molecule to induce antibody response.

For purposes of the present disclosure, "backbone" refers to a protein that serves as a support of the molecule to maintain a stable protein structure and also to present foreign epitopes of interest.

The MEFA of the present invention is not a nucleotide or amino acid sequence found in nature, as it has been constructed by the hand of man. Therefore, the MEFA of the present invention is markedly different from what is found in nature. Similar to Example 5 for the Nature-Based Product Examples of eligible subject matter under 35 U.S.C. 101 issued by the US Patent Office in 2014, the MEFA of the present invention is like claim 2 of that example because the MEFA gene has additional elements, such as the epitopes that provides it with a functionally different characteristic than naturally occurring ETEC bacteria. Most notably, the MEFA of the present invention fails to adhere to the intestine, which is a marked difference from ETEC bacteria found in nature.

All ranges provided herein include each and every value in the range as well as all sub-ranges there-in-between as if each such value or sub-range was disclosed. Further, all aspects and embodiments of the disclosure comprise, consist essentially of, or consist of any aspect or embodiment, or combination of aspects and embodiments disclosed herein.

EXAMPLES

The following examples are simply intended to further illustrate and explain the present invention. The invention, therefore, should not be limited to any of the details in these examples.

Example 1

Materials and Methods
Bacterial strains and plasmids: *E. coli* and ETEC strains used as DNA templates for PCR amplification of the adhesin tip or adhesive subunit genes of CFA/I, CS1-CS6, CS21 and EtpA adhesins and for in vitro antibody adherence inhibition assay, as well as recombinant *E. coli* strains expressing each adhesin tip, adhesive subunit protein and the tip MEFA-I protein are listed below in Table 1. Plasmid pET28α (Novagen, Madison, Wis.) and *E. coli* strain BL21 (GE Healthcare, Piscataway, N.J.) were used to express adhesin tips, adhesive subunits, and the adhesin tip MEFA-I protein.

TABLE 1

A list of *Escherichia coli* strains used in this study. *E. coli* and ETEC strains were used as templates for amplification of adhesin tip genes, and also used in antibody adherence inhibition assay. Recombinant *E. coli* strains expressing each adhesin tip constructed in this study were also included.

| Strain | Relevant characteristics | Source |
|---|---|---|
| H10407 | O78:H11; CFA/I, LT, STa | Johns Hopkins University |
| THK38/pEU405 | CS1 | Emory University |
| DH5α/pEU588 | CS2 | Emory University |
| E116 (E19446) | CS3, LT, STa | University of Gothenburg |
| E106 (E11881/9) | CS4/CS6, LT, STa | University of Gothenburg |
| UM 75688 | CS5/CS6, LT, STa | Johns Hopkins University |
| JF2423 ETP98066 | CS6, LT, STa | Washington University |
| JF2101 | CS21, EtpA, STa | Washington University |
| JF2318 ETP050008 | EtpA, STa | Washington University |
| CFA/I knockout | ΔCFA/I H10407, EtpA, LT, STa | University of Maryland |
| 9473 | CfaE (CFA/I) in pET28α/BL21 Kan+ | this study |
| 9474 | CooD (CS1) in pET28α/BL21 Kan+ | this study |
| 9475 | CotD (CS2) in pET28α/BL21 Kan+ | this study |
| 9505 | CstH (CS3) in pET28α/BL21 Kan+ | this study |
| 9504 | CsaE (CS4) in pET28α/BL21 Kan+ | this study |
| 9533 | CsfD (CS5) in pET28α/BL21 Kan+ | this study |
| 9506 | CssB (CS6) in pET28α/BL21 Kan+ | this study |
| 9468 | LngA (CS21) in pET28α/BL21 Kan+ | this study |
| 9507 | EtpA in pET28α/BL21 Kan+ | this study |
| 9450 | adhesin tip MEFA-I in pET28α/BL21 Kan+ | this study |

Cloning and expression of adhesin tips, adhesive subunits and adhesin tip MEFA-I: PCR primers used to amplify the adhesin tip genes of CFA/I, CS1, CS2, CS3, CS4 and CS5, and adhesive subunit (major structural subunit involving in adhesion) genes of CS6, CS21 and EtpA, are listed in Table 2. PCR amplified adhesin tip or adhesive subunit gene products were digested with restriction enzymes EagI and NcoI or NheI (New England BioLabs Inc, Ipswich, Mass.). Digested products were cloned into vector pET28α and expressed in *E. coli* strain BL21.

TABLE 2

PCR primers used to amplify adhesin tip subunits in this study. Restriction sites, NheI or NcoI in forward primers and EagI in reverse primers, are underlined.

| Primer | Sequence (5'→3') |
|---|---|
| CfaE-F | CTA<u>GCTAGC</u>GATAAAAATCCCGGAAGTG (SEQ ID No. 18) |
| CfaE-R | GAT<u>CGGCCG</u>CTAGAGTGTTTGACTACTTG (SEQ ID No. 19) |
| CS1 (CooD)-F | CTA<u>GCTAGC</u>GGGCGATACCCGGAAACTACAG (SEQ ID No. 3) |

TABLE 2-continued

PCR primers used to amplify adhesin tip subunits in this study. Restriction sites, NheI or NcoI in forward primers and EagI in reverse primers, are underlined.

| Primer | Sequence (5'→3') |
|---|---|
| CS1 (CooD)-R | GATCGGCCGTCATAAATTTTCGACACTGG (SEQ ID No. 4) |
| CS2 (CotD)-F | CTAGCTAGCCAATCATGGCATACGAACGTAG (SEQ ID No. 5) |
| CS2 (CotD)-R | GATCGGCCGTTACAGACTTGAACTACTAGGAG (SEQ ID No. 6) |
| CS3 (CstH)-F | AGTTACATCCATGGGCACTCTAACCAAAGAACTGGCATTAAATGTGC (SEQ ID No. 7) |
| CS3 (CstH)-R | TACATGATCGGCCGTTAATTACCTGAAACTAAATGTTCGTTACC (SEQ ID No. 8) |
| CS4 (CsaE)-F | CTAGCTAGCGATAAAATTCCCGGAGATGAAAG (SEQ ID No. 9) |
| CS4 (CsaE)-R | GATCGGCCGCTAGAGTGTTTGACTACTTGGTGTG (SEQ ID No. 10) |
| CS5 (CsfD)-F | TTTTCCATGGTTATGGTTCAGGCTGCTACA (SEQ ID No. 11) |
| CS5 (CsfD)-R | AGATCGGCCGTTATTTATTGTAACATTTCC (SEQ ID No. 12) |
| CS6 (CssB)-F | AGTTACATCCATGGGCTGGCAATATAAATCTCTGGATGTAAATG (SEQ ID No. 13) |
| CS6 (CssB)-R | ATGTAGATCGGCCGTTAAGTCAAATTTCCTGCATAAGTACCAGAC (SEQ ID No. 14) |
| CS21 (LngA)-F | CTAGCTAGCATGAGCCTGCTGGAAGTTATCATTG (SEQ ID No. 15) |
| CS21 (LngA)-R | GATCGGCCGTTAACGGCTACCTAAAGTAATTG (SEQ ID No. 16) |
| EtpA-F | CTAGCTAGCGGCGTGGGTAATGCAAAAGCCACG (SEQ ID No. 17) |
| EtpA-R | ATGTAGATCGGCCGTTAGCTGAAGGTGTAACGACGGTTCATG (SEQ ID No. 34) |

To construct the adhesin tip MEFA-I gene, first web-based B-cell epitope prediction software was used to in silico identify B-cell epitopes from the adhesin tips of the six adhesins (CFA/I, CS1-CS5) and adhesive subunits of three adhesins (CS6, CS21, EtpA). Then the CFA/I tip CfaE gene (cfaE) was applied as backbone, then eight nucleotide fragments coding surface-exposed but less antigenic peptides were truncated, as confirmed by DNA sequencing, and the nucleotide fragments coding the most antigenic epitope of the other eight adhesin tips or adhesive subunits were inserted into the truncated positions of the cfaE gene. After in silico optimization of epitope presentation, this adhesin tip MEFA-I gene was synthesized (gene synthesis performed by Genewiz, South Plainfield, N.J.). The synthetic gene was digested with enzymes NcoI and EagI, and were cloned in vector pET28α and expressed in *E. coli* BL21.

A single colony from each recombinant strain was cultured in 5 ml Luria-Bertani (LB) broth supplemented with kanamycin (30 μg/ml) at 37° C. overnight. Overnight grown culture was added to 200 ml 2× YT medium (2× Yeast Extract Tryptone). After optical density (OD) reached 0.6, bacteria were induced with 0.1 mM Isopropyl β-D-1-thiogalactopyranoside (IPTG; Sigma, St. Louis, Mo.) and grew for four more hours. Bacteria were collected with centrifugation of 12,000-13,000 rpm for 15 minutes. Pellets, after frozen and thaw, were suspended in 10 ml bacterial protein extraction reagent (B-PER; Pierce, Rockford, Ill.) with vortex. After 30 min at room temperature, bacteria lysates were centrifuged at 12,000-13,000 rpm for 15 min at 4° C. Pellets were suspended in 10-20 ml B-PER with vigorous vortex and pipetting with a 20-ml syringe, mixed with 200-400 μl freshly prepared lysozyme (10 mg/ml, in B-PER), and incubated at room temperature for 20 min. Suspensions were centrifuged; resultant pellets were suspended and then incubated with lysozyme again. After centrifugation, pellets were suspended in 100 ml 1:10 diluted B-PER, vortexed, and centrifuged. Pellets were washed three times with 100 ml PBS, vortexed vigorously, centrifuged at 12,000 rpm for 15 min at 4° C. Final pellets were dissolved in 10 ml PBS.

Extracted proteins were then refolded using a protein refolding kit by following manufacturer's protocol (Novagen). Refolded solubilized proteins were transferred to molecular porous membrane tubing (Spectrum Laboratories, Inc., Rancho Dominguez, Calif.), and dialyzed in 20 mM Tris-HCl, pH8.5 (supplemented with 0.1 mM DTT) at 4° C. After 3-4 h, protein samples were moved to dialysis buffer without DTT, and followed by two more buffer changes. Solubilized proteins (in supernatant) were collected with centrifugation at 12,000 rpm for 10 min at 4° C., and were stored at −80° C.

Mouse immunization with adhesin tip MEFA-I was performed by the following steps. Before being used in mouse immunization, 25 or 30 μl refolded solubilized adhesin tip MEFA-I protein samples (1 mg/ml) were examined in 12% sodium dodecyl sulfate-polyacrylamide gel electrophoresis (SDS-PAGE) with mouse anti-CFA/I antiserum (1:3000). IRDye-labeled goat anti-mouse IgG (1:5000; LI-COR, Lincoln, Nebr.) was used as the secondary antibody. LI-COR Odyssey premium infrared gel imaging system was used to visualize bound proteins. In addition, Coomassie blue staining was used to assess purity of the extracted adhesin tip MEFA-I proteins.

Seven-week-old female BALB/c mice (Charlies River Laboratories International, Inc., Wilmington, Mass.) were used in mouse immunization. A group of eight mice were each intraperitoneally immunized with 150 µg (in 200 µl PBS) adhesin tip MEFA-I protein generated above, together with 1 µg dmLT ($LT_{R192G/L211A}$; provided by Walter Reed Army Institute of Research, Silver Spring, Md.) as adjuvant. Immunized mice received two booster injections intraperitoneally at the same dosage amount of the primary, in an interval of two weeks. Two weeks after the second booster, mice were sacrificed. A group of eight mice without immunization were served as the control group.

Serum samples were collected from each mouse before the primary and two weeks after the final booster, and were stored at −80° C. until use. The mouse immunization study complied with the American Welfare Act by following the 1996 National Research Council guidance and was approved by the Kansas State University's Institutional Animal Care and Use Committee.

Mouse anti-CFA IgG antibody titration was performed by the following steps. Recombinant adhesin tip and adhesive subunit proteins were used as coating antigens respectively in ELISAs to titrate mouse serum anti-CfaE (CFA/I), -CooD (CS1), -CotD (CS2), -CstH (CS3), -CsaE (CS4), -CsfD (CS5), -CssB (CS6), anti-LngA (CS21) and anti-EtpA IgG antibodies in this study. Serum samples collected from each mouse prior to the primary immunization and two weeks after the final booster were initially diluted in 1:400 and then two-folded diluted till to 1:51,200. Four hundred nanogram of each adhesin tip or subunit recombinant protein, in 100 µl coating buffer (41), was added to each well of Immulon 2HB 96-well plates (Thermo Fisher Scientific, Rochester, N.Y.). Plates were incubated at 37° C. for 1 h and then 4° C. overnight. Coated plates were washed three times with PBS-0.05% Tween 20 (PBST), and uncoated sites were blocked with 5% nonfat milk at 37° C. for 1 h. After washing three times with PBST, wells were incubated with mouse serum dilutions at 37° C. for 1 hour. After washing 3 times with PBST, wells were incubated with horseradish peroxidase (HRP) conjugated goat-anti-mouse IgG antibodies (1:3000; Sigma) at 37° c. for 1 h. After 3 washes with PBST and 2 washes with PBS, wells were incubated with 100 µl 3,3',5,5'-tetramethylbezidine (TMB) Microwell Peroxidase Substrate (KPL, Gaithersburg, Md.) at room temperature for 30 min, and were measured for optical density (OD) at 650-nm wavelength. OD readings from the highest dilution that gave readings above 0.3 after subtraction of background readings (OD×dilution) were calculated to antibody titers and presented in $log_{10}$ scale.

A mouse serum antibody adherence inhibition assay was performed by the following steps. Mouse serum in vitro antibody adherence inhibition assay was carried out. Briefly, 30 µl serum pooled from the immunized mice or the control mice was added to ETEC or E. coli bacteria ($4.5 \times 10^6$ CFUs; in 150 µl PBS) that express CFA/I, CS1, CS2, CS3, CS4/CS6, CS5/CS6, CS6, CS21, or EtpA. Incubated at room temperature for 1 h on a shaker (50 rpm), the serum/bacteria mixture was brought to 300 µl with PBS and added to Caco-2 cells ($3 \times 10^5$ cells, in 700 µl DMEM-10% FBS; at a multiplicity-of-infection ratio of 15 bacteria to 1 cell). After incubation at 37° C. for 1 h in a $CO_2$ incubator (5% $CO_2$), Caco-2 cells were gently washed 3 times with PBS to remove non-adherent bacteria, and then dislodged with 0.5% triton X (300 µl per well; 37° C. for 20 min at room temperature). Adherent bacteria (and dislodged Caco-2 cells) were collected with centrifugation, suspended in 1 ml PBS, serially diluted and plated on LB plates. Plates were cultured at 37° C. overnight, and counted for CFUs.

Statistical analysis: Data of antibody adherence inhibition assay were analyzed using the mixed procedure (SAS for windows, version 8; SAS Institute, Cary, N.C.). Results were expressed in means±standard deviations. Student's t-test was used to compare differences between the immunization group and the control group. Differences were considered significant if p<0.05 when treatments were compared at two-tailed distribution and two-sample unequal variance.

Results and Conclusions

Adhesin tip MEFA-I protein carried epitopes of nine adhesin tips or subunits. Epitopes 'QFTEKRSLIKR' (CS1/SEQ ID No. 37), 'SQSIEMRFQDDSQ' (CS2/SEQ ID No. 42), 'NITLDKNAGNT' (CS3/SEQ ID No. 36), 'FYLRKINDDTK' (CS4/SEQ ID No. 41), 'DIGRLQSDAEY' (CS5/SEQ ID No. 35), 'YDSDPKLDSQ' (CS6/SEQ ID No. 38), 'VAMKDAYQRDGKYPDF' (CS21/SEQ ID No. 39), and 'VEGEKSPRRGV' (EtpA/SEQ ID No. 40) were in silico predicted from CooD of CS1, CotD of CS2, CstH of CS3, CsaE of CS4, CsfD of CS5, CssB of CS6, LngA of CS21 and EtpA of EtpA, respectively. Three epitopes from CfaE of CFA/I: 'TEKRSLIKRELQIK' (SEQ ID No. 43), 'QDDNSKSDGKFYLKKINDDSKE' (SEQ ID No. 44) and 'RLQLDAKVKNPEA' (SEQ ID No. 45) were retained in the tip MEFA-I (FIG. 1). This 362-amino acid polypeptide was expressed, extracted, and recognized by mouse anti-CFA/I antiserum (FIG. 1).

Figure 2:
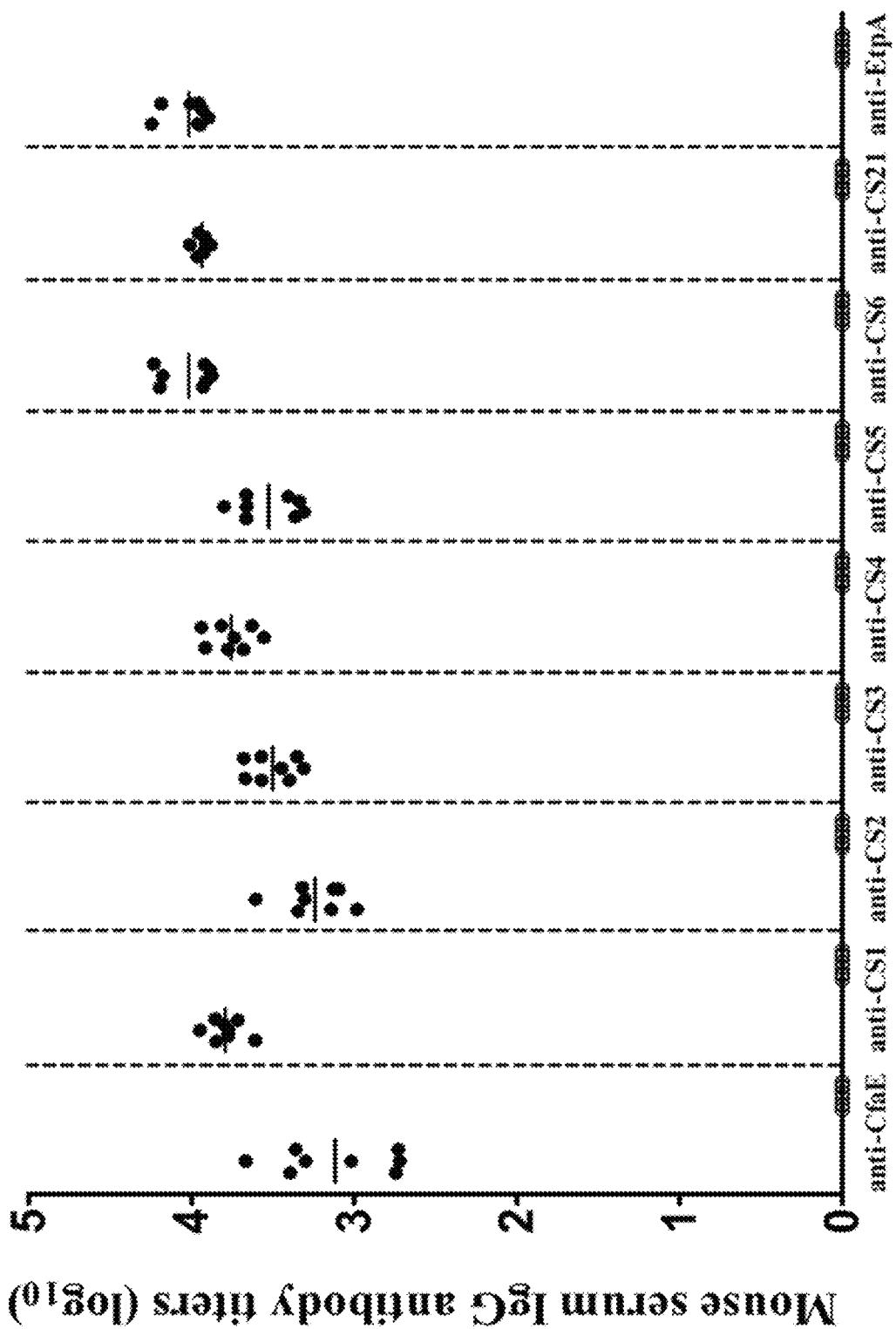
FIG. 2 is a plot of serum anti-CfaE (CFA/I), -CooD (CS1), -CotD (CS2), -CstH (CS3), -CsaE (CS4), -CsfD (CS5), -CssB (CS6), anti-LngA (CS21) and anti-EtpA (EtpA) IgG antibody titers ($\log_{10}$) from mice immunized with tip MEFA-I. Solid circles (●) are titers of mice intraperitoneally immunized with the adhesin tip MEFA-I protein. Each circle represented the IgG titer from an individual mouse. Bars indicated the mean titers of the group specific to each adhesin.
Figure 3:
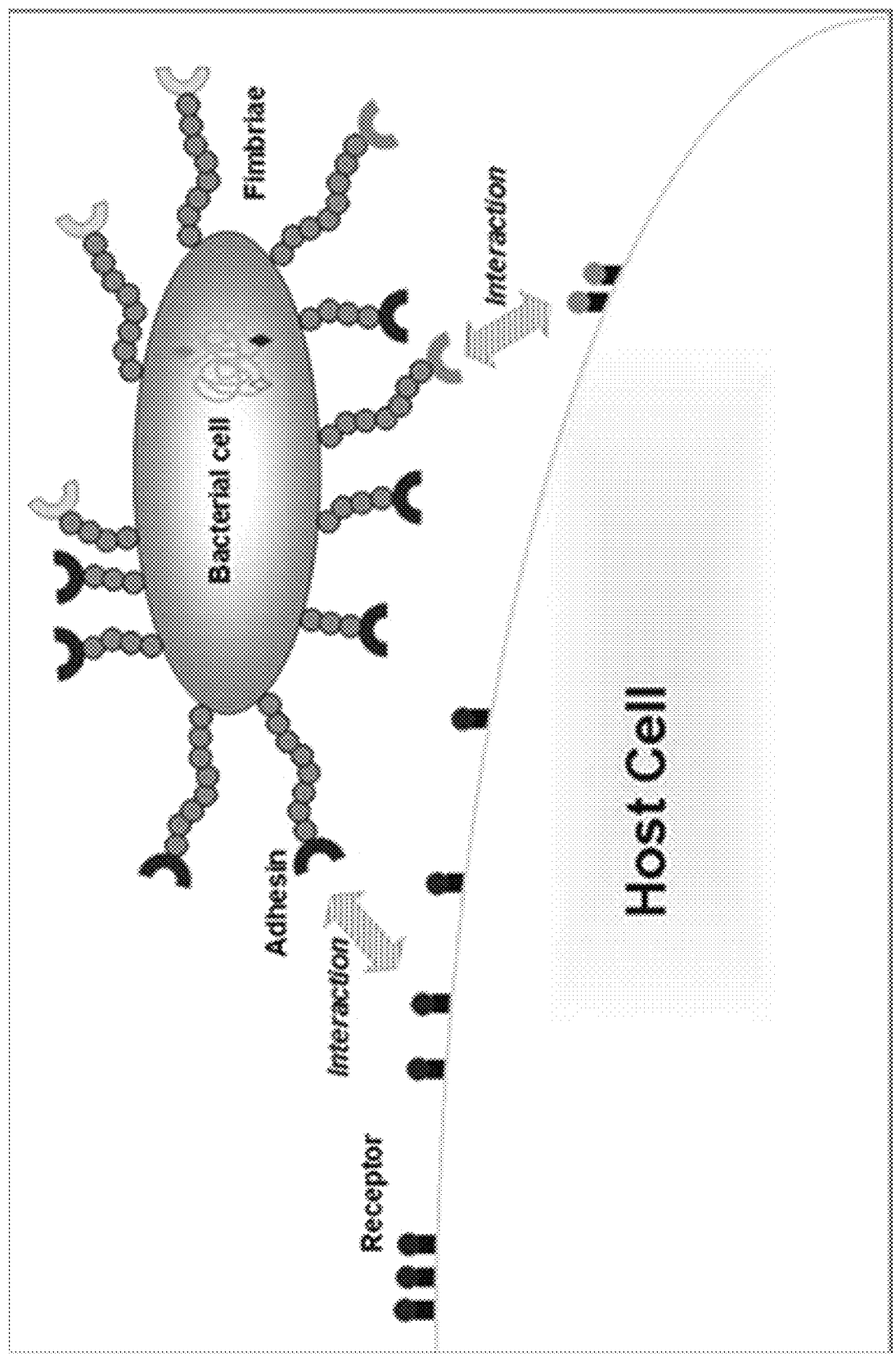
FIG. 3 is an illustration of a host cell and bacterial cell showing adhesin interaction.
Figure 4:
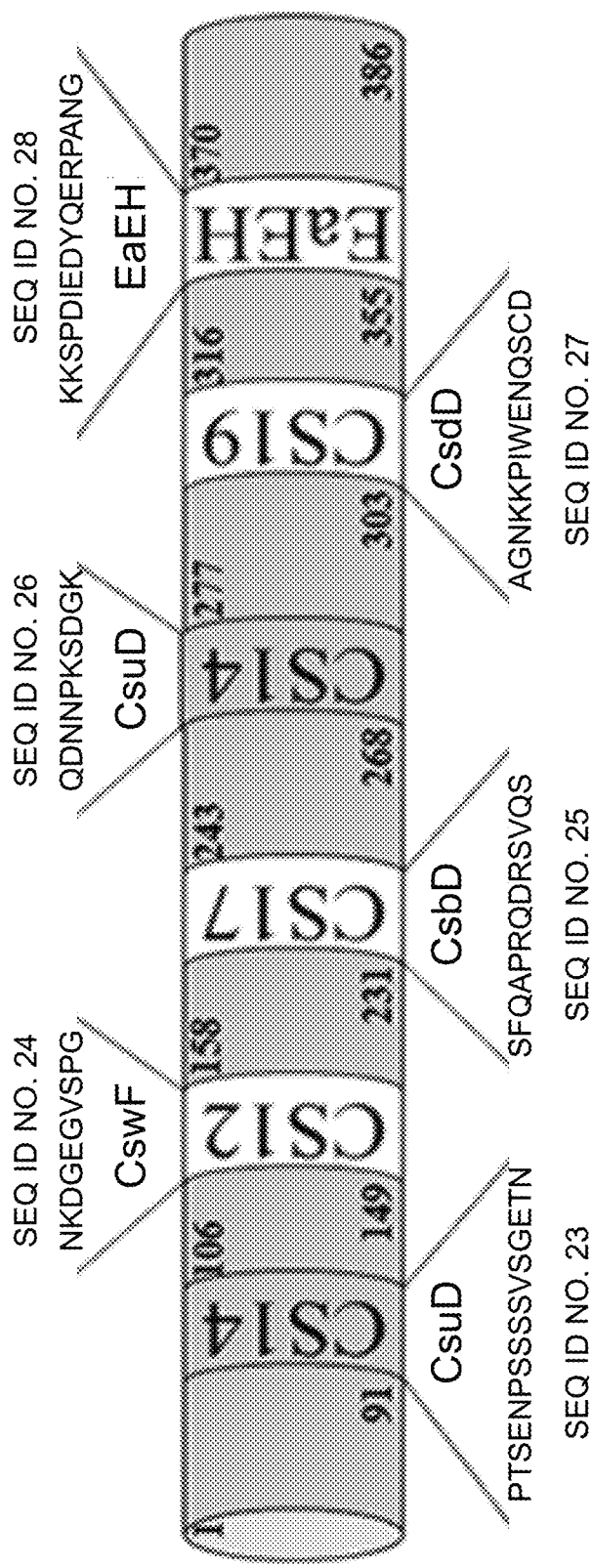
FIG. 4 is an illustration of the genetic structure of adhesin MEFA-I with a CS14 adhesin tip subunit CsuD as the backbone, with two CsuD epitopes retained, where 4 epitopes were substituted with epitopes from tip subunits of CS12 (CswF), CS17 (CsbD), CS19 (CsdD) and EaeH adhesins.

It was found that mice intraperitoneally immunized with the adhesin tip MEFA-I developed immune responses to all nine adhesins. All eight mice intraperitoneally immunized with the adhesin tip MEFA-I recombinant protein developed antibody responses to each of the nine adhesin tips or adhesive subunits (FIG. 2). Anti-CfaE, -CooD, -CotD, -CstH, -CsaE, -CsfD, -CssB, and -LngA and anti-EtpA IgG antibody titers in the immunized mice were 3.1±0.36, 3.8±0.10, 3.2±0.19, 3.5±0.14, 3.8±0.13, 3.5±0.19, 4.0±0.16, 3.9±0.04 and 4.0±0.13 (in $log_{10}$), respectively. No antibody titers to these adhesin tip or subunit antigens were detected in the serum samples of the control mice, or serum collected before the primary immunization.

It was further discovered that mouse serum antibodies inhibited adherence of ETEC or E. coli bacteria expressing these nine adhesins. ETEC bacteria expressing CFA/I, CS3, CS4/CS6, CS5/CS6, CS6, CS21 or EtpA, or H10407 CfaE knock out mutant which expresses EtpA, and recombinant E. coli strains expressing CS1 or CS2 showed significant reduction in adherence to Caco-2 cells, after being incubated with the pooled serum sample of the immunized mice, compared to the same bacteria incubated with the pooled serum of the control mice.

Discussion

The adhesin tip MEFA-I created from this study carried epitopes from nine different ETEC adhesins and induced antibody responses to each of these nine adhesins. That may rejuvenate the concept of epitope vaccinology for developing safe and broadly protective vaccines against immunologically heterogeneous pathogens. Differing from the conceptual epitope vaccine strategy that stacks multiple epitopes into a linear peptide antigen and often leads to inferior immunogenicity or protection, the present disclosure applied the MEFA (multiepitope fusion antigen) approach to use a backbone protein and to substitute surface-exposed peptides of the backbone protein with epitopes of foreign antigens. This MEFA approach results in a protein which better presents the antigenic epitopes of interest.

Future protein structural studies will help to understand antigenic topology of this MEFA-I protein.

The present disclosure included a CssB epitope to represent CS6 adhesin in this tip MEFA construction. Both CssA and CssB are the major structural subunits and play key roles in CS6 adherence. CssA epitope '[72]QVTVYPV[78]' (SEQ ID No. 54) was found capable of inducing in vitro protective antibodies against CS6 adhesin adherence. Data from this study showed that the CssB epitope 'YDSDPKLDSQ' (SEQ ID No. 52) also induced antibodies that inhibited CS6 adherence to Caco-2 cells.

CstH is the major structural subunit and also the adhesive subunit for CS3 adhesin. CstH epitope 'NITLDKNAGNT' (SEQ ID No. 49) in this tip MEFA-I was able to induce strong anti-CstH antibody response. Comparison of antibody titers derived from the major subunit MEFA-I and this tip MEFA-I may not be much informative since different coating antigens were used in antibody titration ELISAs. In vitro antibody adherence inhibition assays suggested antibodies derived against these two CstH epitopes showed similar rates (50% vs. 58% from anti-CFA MEFA-I antibodies and anti-adhesin tip MEFA-I antibodies) inhibiting adherence of CS3 adhesin to Caco-2 cells. Future studies to identify optimal epitopes for ETEC adhesin tips or major subunits will help to improve efficacy of vaccine candidates.

Results from this study showed that the adhesin tip MEFA-I carried adhesin tip or adhesive subunit epitopes induced antibody responses to nine ETEC adhesins, and derived antibodies inhibited adherence of *E. coli* and ETEC bacteria expressing these nine adhesins to Caco-2 cells. Future studies using different immunization routes, different animals and challenge studies will be needed to further characterize antigen antigenicity and potential vaccine application against ETEC diarrhea.

Example 2

Materials and Methods

The method described above will be completed for another embodiment of the present disclosure, an adhesin tip MEFA (tip MEFA-I utilizing the backbone of CS14 having epitopes for CS7, CS12, CS17, CS14, CS19, and EaEH.

TABLE 3

This table shows the sequences of the complete MEFA-II sequence, as well as its constituent elements.

```
Adhesin Tip MEFA-II (final product for 6 adhesins) (SEQ ID No. 20)
MNKILFIFTLFFSSVLFTFAVSAQEGSSNRAKIDQTGDYTNIFGPRDRNESSPKHNILNDYI
TAYSESHTLYDRMIFLCLSSQNTLNGACPTSENPSSSSVSGETNITLQFTEKRSLIKRELQI
KGYKRLLFKGANCPSYLTLNSAHYNKDGEGVSPGGASLYLYIPAGELKNLPFGGIWDAT
LKLRVKRRYDQTYGTYTINITVKLTDKGNIQIWLPQFKSDARVDLNLSFQAPRQDRSVQ
SGRNSVDMCFYDGYSTNSSSLELRFQDNNPKSDGKFYLRKINDDTKEIAYTLSLLLAGK
SAGNKKPIWENQSCDNIADAASLEINWNRITAVTMPEISVPVLCWPGRLQLDAKKSPDIE
DYQERPANGYMGNINITFTPSSQTL Note: underlined amino acids are the epitopes from the tips of 6 adhesins.

CS14-CsuD Backbone:
CS14 Amino Acid (386) (SEQ ID No., 21)
MNKILFIFTLFFSSVLFTFAVSADKIPGDENITNIFGPRDRNESSPKHNILNDYITAYSESHT
LYDRMIFLCLSSQNTLNGACPTSENPSSSSVSGETNITLQFTEKRSLIKRELQIKGYKRLLF
KGANCPSYLTLNSAHYTCNRNSASGASLYLYIPAGELKNLPFGGIWDATLKLRVKRRYD
QTYGTYTINITVKLTDKGNIQIWLPQFKSDARVDLNLRPTGGGTYIGRNSVDMCFYDGY
STNSSSLELRFQDNNPKSDGKFYLRKINDDTKEIAYTLSLLLAGKSLTPTNGTSLNIADAA
SLEINWNRITAVTMPEISVPVLCWPGRLQLDAKVENPEAGQYMGNINITFTPSSQTL
Epitopes predicted: 23-33, 84-99, 141-150, 221-231, 255-264, 289-299, 336-346.

Replacement Epitopes substituted for predicted epitopes above.

CS7: QEGSSNRAKIDQTGDY 24-39 (SEQ ID No. 22)

CS14: PTSENPSSSSVSGETN 91-106 (retained from the backbone) (SEQ ID No. 23)

CS12: NKDGEGVSPG 149-158 (SEQ ID No. 24)

CS17: SFQAPRQDRSVQS 231-243 (SEQ ID No. 25)

CS14: QDNNPKSDGK; 268-277 (SEQ ID No. 26)

CS19: AGNKKPIWENQSCD 303-316 (SEQ ID No. 27)

EaEH: KKSPDIEDYQERPANG 355-370 (SEQ ID No. 28)

CS14 tip CSuD Backbone Nucleotide sequence (SEQ ID NO. 109)
ATGAATAAGATTTTATTTATTTTTACATTGTTTTTCTCTTCAGTACTTTTTACATTTGC
TGTATCGGCAGATAAAATTCCCGGAGATGAGAATATAACTAATATTTTTGGCCCGCG
TGACAGGAACGAATCTTCCCCCAAACATAATATATTAAATGACTATATTACAGCATA
CAGTGAAAGTCATACTCTGTATGATAGGATGATTTTTTTATGTTTGTCTTCTCAAAAT
ACACTTAATGGAGCATGTCCAACCAGTGAGAATCCTAGCAGTTCATCGGTCAGTGGC
GAAACAAATATAACATTACAATTTACGGAAAAAAGAAGTTTAATTAAAAGAGAGCT
ACAAATTAAAGGCTATAAACGATTATTGTTCAAAGGTGCTAACTGCCCATCCTACCT
AACACTTAACTCAGCTCATTATACCTGCAATAGAAACTCGGCTTCAGGTGCAAGTTT
ATATTTATATATTCCTGCTGGCGAACTAAAAAATTTACCTTTTGGTGGTATCTGGGAT
GCTACTCTGAAGTTAAGAGTAAAAAGACGATATGATCAGACCTATGGAACTTACAC
TATAAATATCACTGTTAAATTAACTGATAAGGGAAATATTCAGATATGGTTACCTCA
GTTCAAAAGTGACGCTCGCGTCGATCTTAACTTGCGTCCAACTGGTGGGGGCACATA
```

TABLE 3-continued

This table shows the sequences of the complete MEFA-II sequence, as well as its constituent elements.

<u>TATTGGAAGAAATTCTGTTGATATGTGCTTTTATGATGGATATAGTACTAACAGCAG</u>
CTCTTTGGAGCTAAGATTT<u>CAGGATAACAATCCTAAATCTGATGGGAAATTTTATCT</u>
AAGGAAAATAAATGATGACACCAAAGAAATTGCATATACTTTGTCACTTCTCTTGGC
GGGTAAA<u>AGTTTAACTCCAACAAATGGAACGTCATTAAAT</u>ATTGCTGACGCAGCTTC
TCTGGAAATAAACTGGAATAGAATTACAGCTGTCACCATGCCAGAAATCAGTGTTCC
GGTGTTGTGTTGGCCTGGACGTTTGCAATTGGAT<u>GCAAAAGTGGAAAATCCCGAGGC</u>
<u>CGGACAATATAT</u>GGGTAATATTAATATTACTTTCACACCAAGTAGTCAAACACTCTA
G

CS7-Cs213 (SEQ ID No. 29)
MKNKLLFMMLTILGAPGIAAAAGYDLANSEYNFAVNELSKSSFNQAAIIGQAGTNNSAQ
LRQGGSKLLAVVAQ<u>EGSSNRAKIDQTGDY</u>NLAYIDQAGSANDASISQGAYGNTAMIIQK
GSGNKANITQYGTQKTAIVVQRQSQMAIRVTQR

Epitope [73-88 (16)]: QEGSSNRAKIDQTGDY (SEQ ID No. 22)

CS12-CswF (SEQ ID No. 30)
MLKRISCIIFVFFSGLIYAAEITNQIELSVKVNISKPMCKLNSGTQTIDEGDFDVLDIITENR
KLNGHATFKFTECSSVKNMKIKEKQAGQNPALDIVNNYIPNSKGDRMAKGVAVKLLDD
KKQEIQLNKEMNVIVEESLTEKDLTLNAQVIS<u>INKDGEGVSPG</u>LLQTAIGMEISYE

Epitope (155-164): NKDGEGVSPG (SEQ ID No. 24)

CS12-CswF Nucleotide Sequence (SEQ ID No. 110)
atgttgaaaag aatatcgtgt ataattttg ttttttttc
agggctgatt tatgctgcgg aaattacaaa tcagatagag ctttcggtaa aggttaatat
atctaagcct atgtgtaaac ttaattctgg aacgcaaaca atagacttcg gcgattttga
tgtactggat attattacgg agaacagaaa attaaatggt catgcgacct ttaaatttac
tgagtgtagt tctgtcaaaa acatgaagat aaaatttaaa caggcaggac aaaatccagc
gttagatatc gtaaacaatt atatccctaa tagtaaggga gatagaatgg caaggggt
agcggtaaag cttctggatg ataaaaagca agaaattcaa ctgaacaagg aaatgaatgt
tattgtggag gagagtctga catttaaaga tttaacgtta aatgctcagg ttatctctat
<u>taataaagac ggagagggag tttcacctgg g</u>ctacttcag accgcaatag gaatggagat
atcctatgaa tga Primers to amplify the segment for coating antigen in antibody titration ELISA
RN-CS12-F: ATA <u>TCC ATG GCT</u> ATG TGT AAA CTT AAT TCT GGA (SEQ ID No. 114)

RN-CS12-R: ATC <u>TCG GCC GCT</u> ATT GCG GTC TGA AGT AGC (SEQ ID No. 115)

CS17-CsbD (SEQ ID No. 31)
MKKIFIFLSIIFSAVVSAGRYPETTVGNLTK<u>SFQAPRQDRSVQS</u>PIYNIFTNHVAGYSLSHN
LYDRIVELCTSSSNPVNGACPTLGTSGVQYGTTTITLQFTEKRSLIKRNINLAGNKKPIWE
NQSCDTSNLMVLNSKSWSCGHYGNANGTLLNLYIPAGEINKLPFGGIWEATLILRLSRY
GEVSSTHYGNYTVNITVDLTDKGNIQVWLPGEHSNPRVDLNLHPIGNYKYSGSNSLDMC
FYDGYSTNSDSMVIKFQDDNPTYSSEYNLYKIGGTEKLPYAVSLLMGEKIFYPVNGQSFT
INDSSVLETNWNRVTAVAMPEVNVPVLCWPARLLLNADVNAPDAGQYSGQIYITFTPS
VENL

Epitope (32-44): SFQAPRQDRSVQS (SEQ ID No. 25)

CS17 CsbD Nucleotide Sequence (SEQ ID No. 111)
atgaaaaa agatatttat tttttgtct atcatattt
ctgcggtggt cagtgccggg cgatacccgg aaactacagt aggtaatctg acgaag<u>agtt</u>
<u>ttcaagcccc tcgtcaggat agaagcgtac aatc</u>accaat atataacatc tttacgaatc
atgtggctgg atatagtttg agtcataact tatatgacag gattgttttt ttatgtacat
cctcgtcgaa tccggttaat ggtgcttgcc caacccttgg aacatctgga gttcaatacg
gtactacaac cataaccttg cagtttacag aaaaagaag tctgataaaa agaaatatta
atcttgcagg taataagaaa ccaatatggg agaatcagag ttgcgacact agcaatctaa
tggtgttgaa ttcgaagtct tggtcctgtg ggcattacgg aaatgctaac ggaacacttc
taaatctgta tatccctgca ggagaaatca acaaattgcc ttttggaggg atatgggagg
caactctgat cttacgctta tcaagatatg gcgaagtcag tagcacccat acggcaatt
ataccgtaaa tattacggtt gatttaactg ataaaggtaa tattcaggta tggcttccag
ggtttcacag caacccgcgt gtagacctga atctgcaacc tatcggtaat tataaatata
gtggtagtaa ttcactcgac atgtgttct atgatggata tagtacaaac agtgatagca
tggtaataaa gttccaggat gataatccta cctattcatc tgaatataat ctttataaga
taggggcac tgaaaaatta ccatatgctg tttcactgct tatgggagaa aaatatttt
atccagtgaa tggtcaatca tttactatca atgacagtag tgtactcgaa acaaactgga
atcgagtaac cgcagttgct atgccggaag ttaatgttcc agtattatgc tggccagcaa
gattgctatt aaatgctgat gtaaatgctc ccgatgcagg acagtattca ggacagatat
ataacatt tacacccagt gtcgaaaatt tatga Primers to amplify the segment for coating antigen in antibody titration ELISA
RN-CS17-F: TTT <u>TCC ATG GGC</u> ATG AAA AAG ATA TTT ATT TTT (SEQ ID No. 116)

RN-CS17-R: GGT <u>GCG GCC GTT</u> ATA TAT ATC TGT CCT GAA (SEQ ID No. 117)

TABLE 3-continued

This table shows the sequences of the complete MEFA-II sequence, as well as its constituent elements.

CS19-CsdD (SEQ ID No. 32)
MKKIFIFLSIIFSAVVSAGRYPETTVGNLTKSFQAPRLDRSVQSPIYNIFTNEIVAGYSLSHR
LYDRIVFVCTSSSNPVNGACPTIGTSRVEYGTTTITLQFTEKRSLIKRNINL<u>AGNKKPIWEN</u>
<u>QSCD</u>TSNLMVLNSKSWSCGALGNANGTLLNLYIPAGEINKLPFGGIWEATLILRLSRYGE
VSSTHYGNYTVNITVDLTDKGNIQVWLPGFHSNPRVDLNLHPIGNYKYSGSNSLDMCFY
DGYSTNSDSMVIKFQDDNPTNSSEYNTLYKIGGTEKLPYAVSLLMGGKIFYPVNGQSFTIN
DSSVLETNWNRVTAVAMPEVNPVLCWPARLLLLNADVNAPDAGQYSGQIYITFTPSVE
NL

Epitope (115-128): AGNKKPIWENQSCD (SEQ ID No. 27)
C519-CsdD (SEQ ID No. 112) Nucleotide Sequence
atgaaaaa gatatttatt tttttgtcta tcatattttc tgcggtggtc
agtgccgggc gataccgga aactacagta ggtaatctga cgaagagttt caagcccct
cgtctggata aagcgtaca atcaccaata tataacatct ttacgaatca tgtggctgga
tatagtttga gtcatagatt atatgacagg attgtttttg tatgtacatc ctcgtcgaat
ccggttaatg gtgcttgccc aaccattgga acatctagga ttgaatacgg tactacaacc
ataaccttgc agtttacaga aaaaagaagt ctgataaaaa gaaatattaa tctt<u>gcaggt</u>
<u>aataagaaac caatatggga gaatcagagt tgcgac</u>acta gcaatctaat ggtgttgaat
tcgaagtctt ggtcctgtgg ggctctagga atgctaacg aacacttct aaatctgtat
atccctgcag gagaaatcaa caaattgcct tttggaggga tatgggaggc aactctgatc
ttacgcttat caagatatgg cgaagtcagt agcacccatt acggcaatta taccgtaaat
attacggttg atttaactga taaggtaat attcaggtat ggcttccagg gttcacagc
aacccgcgtg tagacctgaa tctgcaccct atcggtaatt ataaatatag tggtagtaat
tcactcgaca tgtgtttcta tgatggatat agtacaaaca gtgatagcat ggtaataaag
ttccaggatg ataatcctac caattcatct gaatataatc tttataagat aggggggcact
gaaaaattac catatgctgt ttcactgctt atgggaggaa aaatattta tccagtgaat
ggtcaatcat ttactatcaa tgacagtagt gtactcgaaa caaactggaa tcgagtaacc
gcagttgcta tgccggaagt taatgttcca gtattatgct ggccagcaag attgctatta
aatgctgatg taaatgctcc cgatgcagga cagtattcag acagatata tataacattt
acacccagtg tcgaaaattt atga Primers to amplify the segment for coating antigen in antibody titration ELISA
RN-CS19-F: GTC <u>ACC ATG GA</u>T ATG ACA GGA TTG TTT TTG TAC (SEQ ID No. 118)

RN-CS19-R: GGT <u>GCG GCC G</u>TT ATA TAT ATC TGT CCT GAA (SEQ ID No. 119)

EaeH (SEQ ID No. 33)
M S H Y K T G H K Q P R F R Y S V L A R C V A W A N I S V Q V L F P L A V T F T P V
M A A R A Q H A V Q P R L S M G N T T V T A D N N V E K N V A S F A A N A G T F L
S S Q P D S D A T R N F I T G M A T A K A N Q E I Q E W L G K Y G T A R V K L N V D
K D F S L K D S S L E M L Y P I Y D T P T N M L F T Q G A I H R T D D R T Q S N I G F
G W R H F S G N D W M A G V N T F I D H D L S R S H T R I G V G A E Y W R D Y L K L
S A N G Y I R A S G W K K S P D I E D Y Q E R P A N G W D I R A E G Y L P A W P Q L
G A S L M Y E Q Y Y G D E V G L F G K D K R Q K D P H A I S A E V T Y T P V

Epitope (222-237): KKSPDIEDYQERPANG (SEQ ID No. 28)

EaeH Nucleotide Sequence (SEQ ID No. 113)
ATGTCACATTATAAAACAGGTCATAAACAACCACGATTTCGTTATTCAGTTCTGGCC
CGCTGCGTGGCGT
GGGCAAATATCTCTGTTCAGGTTCTTTTTCCACTCGCTGTCACCTTTACCCCAGTAAT
GGCGGCACGTGC
GCAGCATGCGGTTCAGCCACGGTTGAGCATGGGAAATACTACGGTAACTGCTGATA
ATAACGTGGAGAAA
AATGTCGCGTCGTTTGCCGCAAATGCCGGGACATTTTTAAGCAGTCAGCCAGATAGC
GATGCGACACGTA
ACTTTATTACCGGAATGGCCACAGCTAAAGCTAACCAGGAAATACAGGAGTGGCTC
GGGAAATATGGTAC
TGCGCGCGTCAAACTGAATGTCGATAAAGATTTCTCGCTGAAGGATTCTTCGCTGGA
AATGCTTTATCCG
ATTTATGATACGCCGACAAATATGTTGTTCACTCAGGGGGCAATACATCGTACAGAC
GATCGTACTCAGT
CAAATATTGGTTTTGGCTGGCGTCATTTTTCAGGAAATGACTGGATGGCGGGGGTGA
ATACTTTTATCGA
TCATGATTTATCCCGTAGTCATACCCGCATTGGTGTTGGTGCGGAATACTGGCGCGA
TTATCTGAAACTG
AGCGCCAATGGTTATATTCGGGCTTCTGGCTGGAAAAAATCGCCGGATATTGAGGAT
TATCAGGAACGCC
CGGCGAATGGCTGGGATATTCGTGCTGAGGGCTATTTACCCGCCTGGCCGCAGCTTG
GCGCAAGCCTGAT
GTATGAACAGTATTATGGCGATGAAGTCGGGCTGTTTGGTAAAGATAAGCGCCAGA
AAGACCCGCATGCT
ATTTCTGCCGAGGTGACCTATACGCCAGTGCC

TABLE 3-continued

This table shows the sequences of the complete MEFA-II sequence, as well as its constituent elements.

```
Primers to amplify the segment for coating antigen in antibody titration ELISA
RN-EaEH-F: TTT ACC ATG GTA ATG GCG GCA CGT GCG CAG CAT (SEQ ID No. 120)

RN-EaEH-R: TTT CCG GCC GTT ATC TTT ACC AAA CAG CCC (SEQ ID No. 121
```

Figure 5:
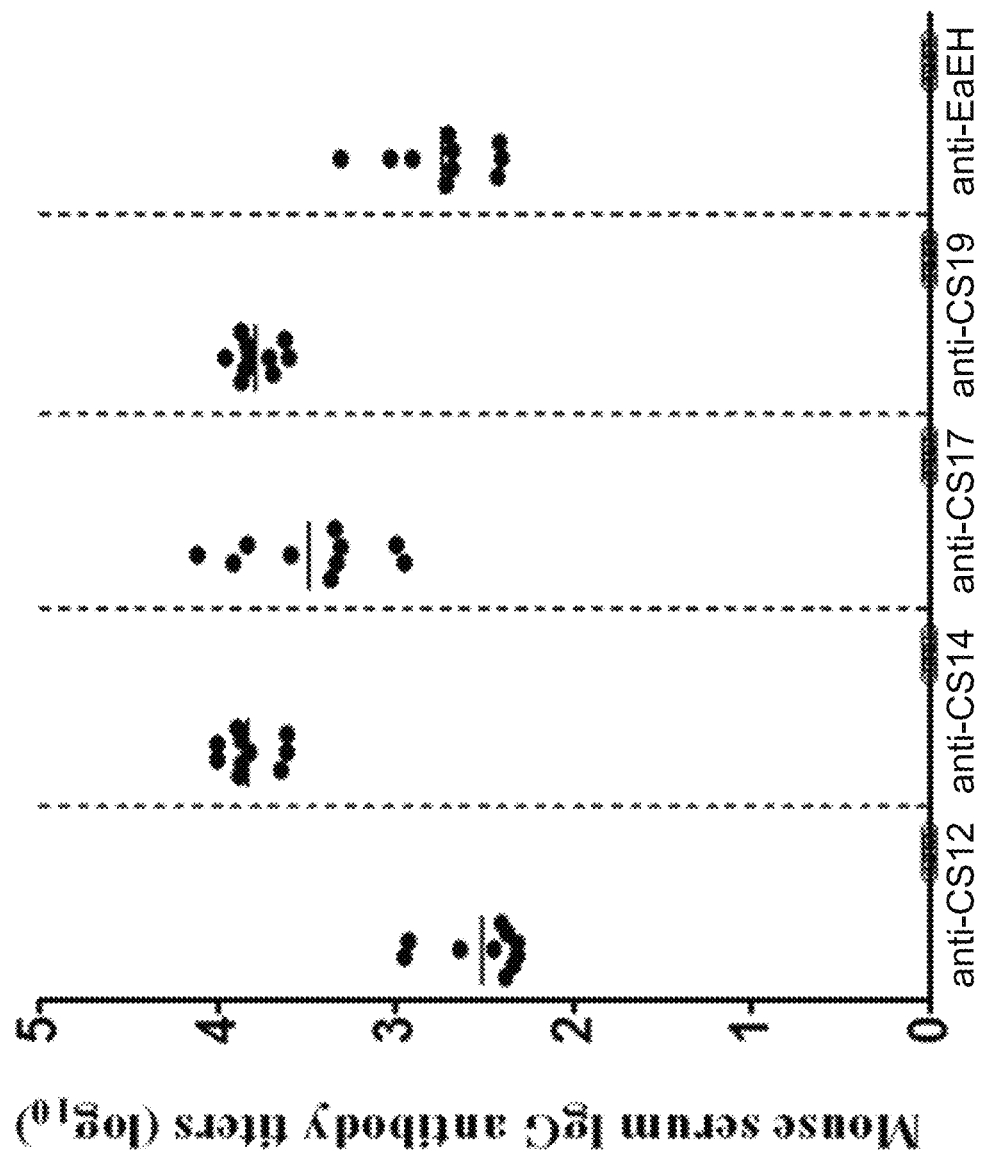
FIG. 5 is a plot of serum IgG antibody titers ($\log_{10}$) for anti-CS12, anti-CS14, anti CS17, anti-CS19, and anti-EaeH IgG antibodies from mice subcutaneously immunized with adhesin tip MEFA-II protein, where each dot represented an IgG titer from an individual mouse and bars indicated mean titers.

Results and Conclusions:

Adult female Balb/C mice subcutaneously immunized with 40 μg tip MEFA-II, with 2 μg dmLT (double mutant LT, $LT_{R192G/L211A}$) adjuvant, one primary and two boosters at an interval of two weeks, developed antibody responses to CS12, CS14, CS17, CS19 and EaeH adhesins (FIG. 5). No antigen-specific antibody response was detected in the control mice.

FIG. 5 shows mouse serum IgG antibody titers ($\log_{10}$), where mice immunized with adhesion tip MEFA-II developed anti-CS12, anti-CS14, anti-CS17, and anti-EaeH IgG antibodies. Each dot in FIG. 5 represented IgG titer from an individual mouse, where the bars indicate mean IgG titers.

ETEC field isolates expressing CS12, CS14, CS17, CS19 or EaeH, after incubated with serum of mice SC immunized with the adhesin tip MEFA-II, showed significant reduction in adherence to Caco-2 cells, compared to ETEC strains incubated with serum of the control mice. That suggested serum antibodies of the immunized mice were neutralizing, inhibited adherence of ETEC bacteria expressing any of these five adhesins.

TABLE 4

Results from mouse serum antibody in vitro adherence inhibition assays. Caco-2 cells (5 × 10$^5$) were incubated with each ETEC bacteria strain expressing a different adhesin (in PBS), ETEC bacterial premixed with serum of the control mice, or ETEC bacteria premixed with serum of the mice immunized with adhesin tip MEFA-II.

| ETEC strains | serum of control mice | serum of immunized mice |
|---|---|---|
| 3276, CS12/CS20/LT/STa (×10$^3$) | 227.6 ± 21.2 | 156 ± 17.1<br>p = 0.01 |
| E7476A, CS14 (×10$^2$) | 91.8 ± 7.0 | 63.4 ± 6.3<br>p < 0.01 |
| E20738A, CS17 (×10$^2$) | 137.2 ± 8.1 | 19.4 ± 3.0<br>p < 0.001 |
| D526-1, CS19 (×10$^2$) | 92.2 ± 6.7 | 70.2 ± 9.2<br>p = 0.02 |
| H10407-EaeH/EtpA/CFA/I/LT/STa (×10$^2$) | 126.6 ± 32.4 | 67.2 ± 15.3<br>p = 0.04 |

Example 3

The method described in Example 1 above will be completed for another embodiment of the present disclosure, a major subunit CFA MEFA-II utilizing the backbone of CS21 having epitopes for CS19, CS17, EtpA, CS14, CS7, CS12, and EaeH.

Materials and Methods

This CFA MEFA-II used CS21 major subunit LngA as the backbone, and has LngA surface-exposed and less antigenic epitopes substituted by the most antigenic epitopes from the major subunits of CS7, CS12, CS14, CS17, CS19, EtpA and EaeH adhesins. Therefore, CFA MEFA-II carried antigenic elements of 8 adhesins of enterotoxigenic Escherichia coli (ETEC), and is expected to induce antibodies against all these 8 ETEC adhesins (CS7, CS12, CS14, CS17, CS19, CS21, EtpA and EaeH).

Figure 6:
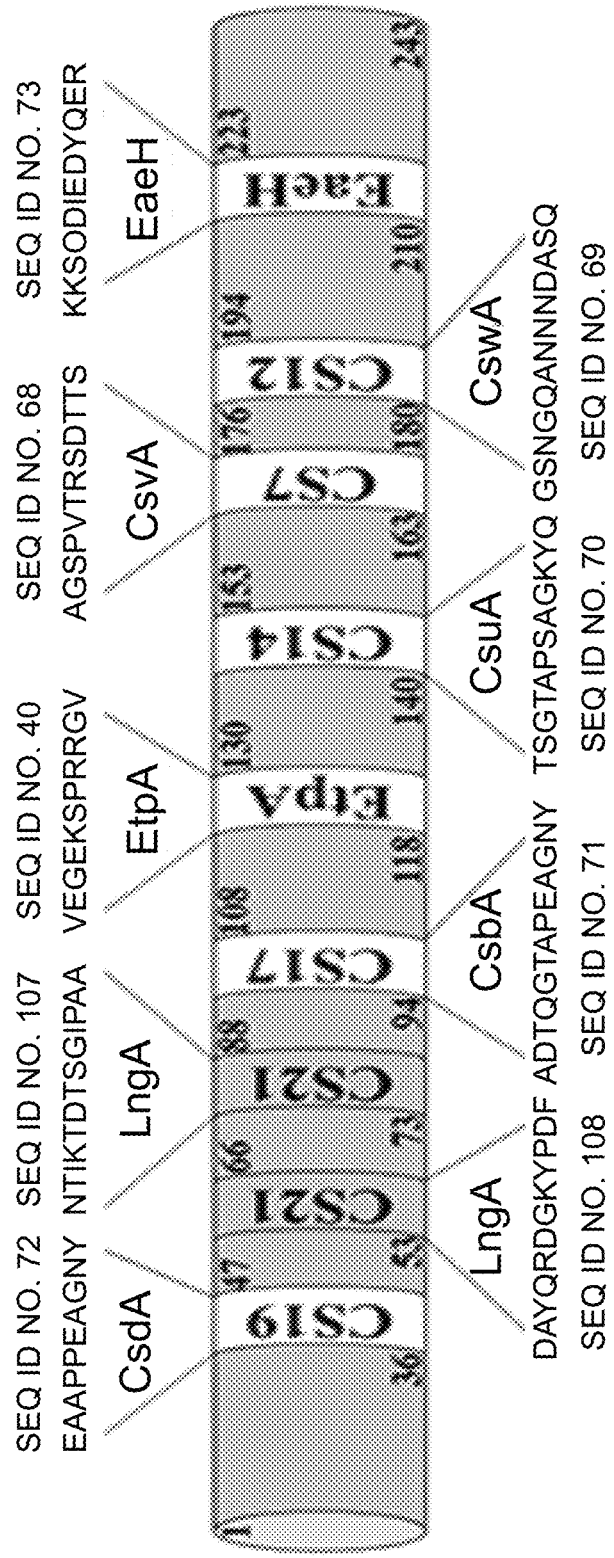
FIG. 6 is an illustration of the genetic structure of major subunit CFA MEFA-II with a CS21 major subunit LngA as the backbone, with a LngA surface-exposed and epitopes from the major subunits of CS7, CS12, CS14, CS17, CS19, EtpA and EaeH adhesins.

The structure of CFA MEFA-II of Example 3 is shown in FIG. 6.

```
CFA MEFA-H amino acid sequence (SEQ ID No. 67))
MSLLEVIIVLGIIGTIAAGVVILAQRAFDSRAVTDLEAAPPEAGNYTVRVAMKDAYQRD
GKYPDFVDPLSLTANTIKTDTSGIPAAQLVQLGKADTQGTAPEAGNYISGDFIAIGGAVE
GEKSPRRGVKKGFAIELNGLTSGTAPSAGKYQEQCRSILGQVGAGSPVTRSDTTSWEYV
AGSNGQANNNDASQVDMSVAASTTVLRSLGNKKSPDIEDYQERTADKILSTCTAQVNSI
TLGSR CS7 Epitope: AGSPVTRSDTTS (SEQ ID No. 68)

CS12 Epitope: GSNGQANNNDASQ (SEQ ID No. 69)

CS14 Epitope: TSGTAPSAGKYQ (SEQ ID No. 70)

CS17 Epitope: ADTQGTAPEAGNY (SEQ ID No. 71)

CS19 Epitope: EAAPPEAGNY (SEQ ID No. 72)

EtpA Epitope: VEGEKSPRRGV (SEQ ID No. 40)

EaeH Epitope: KKSPDIEDYQER (SEQ ID No. 73)
```

CFA MEFA-H DNA sequence (SEQ ID No. 74)
ATGAGCCTGCTGGAAGTTATCATTGTTCTTGGCATTATCGGTACGAT -continued CS14 major subunit (CsuA) (SEQ ID No. 83)
Amino acid sequence
MKLKKTIGAMALSTIFVAVSASAVEKNITVTASVDPTIDILQANGSALPTAVDLTYLPGA
KTFENYSVLTQIYTNDPSKGLDVRLVDTPKLTNILQPTSTIPLTVSWAGKTLSTSAQKIAV
GDLGFGSTGTAGVSNSKELVIGATTSGTAPSAGKYQGVVSIVMTQSTDTAAPVP Epitope: 146-157 (12aa)

Nucleotide sequence (SEQ ID No. 84)
ATGAAATTAAAAAAAACTATTGGCGCAATGGCTCTGAGCACAATATTTGTAGCGG
TGAGTGCTTCAGCAGTAGAGAAAAATATTACTGTGACAGCCAGTGTTGATCCTACTA
TTGATATTCTTCAAGCAAATGGTTCTGCGCTACCGACAGCTGTAGATTTAACTTATCT
ACCTGGTGCAAAAACTTTTGAAAATTACAGTGTTCTAACCCAGATTTACACAAATGA
CCCTTCAAAAGGTTTAGATGTTCGACTGGTTGATACACCGAAACTTACAAATATTTT
GCAACCGACATCTACCATTCCTCTTACTGTCTCATGGGCAGGGAGGACATTAAGTAC
AAGTGCTCAGAAGATCGCAGTTGGCGATCTGGGTTTTGGTTCCACCGGAACGGCAG
GTGTTTCGAATAGTAAAGAATTAGTAATTGGAGCAACTACATCCGGAACTGCACCA
AGTGCAGGTAAGTATCAAGGCGTCGTT**TCCATTGTAATGACTCAATCGACAAACT
AA**

Primer to amplify the subunit the segment as antibody titration ELISA coating antigen:
CA14-CsuA-F: CATG<u>CCATGG</u>AAATGGCTCTGAGCACAATATTTGTAG (NcoI) (SEA
ID No. 85)

CA14-CsuA-R: GAGT<u>CGGCCG</u>CTTTAGTTTGTCGATTGAGTCATTACAATGGA (EagI)
(SEQ ID No. 86)

CS17 major subunit gene (CsbA) (SEQ ID No. 87)
Amino acid sequence
MKLKKTIGAMAMATLFATMAASAVEKNITVRASVDPKLDLLQADGTSLPDSIALTYSS
ASNNFEVYSLNTAIHTNDKSKGVVVKLSASPVLSNIMKPNSQIPMKVTLGGKTLNTTDT
EFTVDTLNFGTSGVENVSSTQQLTIHADTQGTAPEAGNYQGIISLIMTQKT Epitope: 144-156 (13aa)

Nucleotide sequence (SEQ ID No. 88)
ATGAAACTGAAGAAAACAATTGGCGCAATGGCTATGGCGACTCTGTTTGCCACCA
TGGCTGCCTCTGCAGTCGAAAAAAATATTACTGTGAGGGCAAGTGTTGACCCTAAAC
TTGATCTTCTGCAAGCAGATGGAACTTCACTGCCGGACTCTATCGCATTAACCTATTC
TTCGGCTTCAAATAATTTTGAAGTTTACTCTCTTAATACTGCTATTCATACAAATGAC
AAAAGCAAGGGAGTTGTAGTGAAGCTGTCAGCTTCACCAGTTCTGTCCAATATTATG
AAGCCAAACTCGCAAATTCCGATGAAAGTGACTTTGGGGGGGAAGACGCTGAATAC
AACTGATACTGAGTTTACTGTTGATACTCTGAACTTTGGTACATCTGGTGTTGAAAA
CGTTTCTTCCACTCAACAGCTTACGATTCATGCAGACACACAAGGAACTGCGCC**TGA
GGCAGGCAATTACCAAGGTATTATTTCTCTTATCATGACTCAAAAAACTTAA**

Primers to amplify the segment as antibody titration ELISA coating antigen:
CA17-CsbA-F: CTA<u>GCTAGC</u>TAGATGGCTATGGCGACTCTGTTTGCCA (Nhe I) (SEQ ID
No. 89)

CA17-CsbA-R: GAGT<u>CGGCCGC</u>TTTATAATACCTTGGTAATTGCCTGCCTCA (EagI)
(SEQ ID No. 90)

CS19 major subunit (CsdA) (SEQ ID No. 91)
Amino acid sequence:
MKLKKTIGAMAMATLFATMAASAVEKNITVRASVDPKLDLLQADGTSLPDSIALTYSS
ASNNFEVYSLNTAIHTNDKTKAVVVKLSAPVLSNIMKPSSQIPMKVTLGGKTLSTADA
EFAADTLNFGASGVENVSSVQQLTIHAEAAPPEAGNYQGVISLIMTQKT Epitope: 145-154 (10aa)

Nucleotide sequence (SEQ ID No. 92)
ATGAAACTGAAGAAAACAATTGGCGCAATGGCTATGGCGACTCTGTTTGCCACCA
TGGCTGCCTCTGCAGTCGAAAAAAATATTACTGTGAGGGCAAGTGTTGACCCTAAAC
TTGATCTTCTGCAAGCAGATGGAACTTCACTGCCGGACTCTATCGCATTAACCTATTC
TTCGGCTTCAAATAATTTTGAAGTTTACTCTCTTAATACTGCTATTCATACAAATGAC
AAAACCAAGGCAGTTGTAGTGAAGCTGTCAGCTCCAGCAGTTCTGTCCAATATTATG
AAGCCAAGCTCGCAAATTCCGATGAAAGTGACTTTGGGGGGGAAGACGCTGAGTAC
AGCTGATGCTGAGTTTGCTGCTGATACTCTGAACTTTGGTGCATCTGGTGTTGAAAA
CGTTTCTTCCGTTCAACAGCTTACGATTCATGCAGAAGCTGCTCCGCCTGAGGCAGG
TAATTACCAAGGTGTTATTTCTCTTATCATGACTCAAAAAACTTAA

Primers to amplify the subunit segment as antibody titration ELISA coating antigen:
CA19-CsdA-F: CTA<u>GCTAGC</u>TAGATGGCTATGGCGACTCTGTTTGCCA (Nhe I) (SEQ ID
No. 93)

CA19-CsdA-R: GAGT<u>CGGCCG</u>CTTTAGAGTCATGATAAGAGAAATAACAC (EagI) (SEQ
ID No. 94)

-continued

CS21 major subunit (LngA) (SEQ ID No. 95)
Amino acid sequence
MSLLEVIIVLGIIGTIAAGVVILAQRAFDSRAVTDLVTNTNTVRVAMKDAYQRDGKYPD
FVDPLSLTANTIKTDTSGIPAAQLVQLGKITPDEVRNNISGDFIAIGGALTSNGAQVKKGF
AIELNGLSQEQCRSILGQVGNNWEYVAIGTSASGSYAMTATGVDMSVAASTTVLRSLG
NGGQTTLTADKILSTCTAQVNSITLGSR Epitope: 49-60 (12aa) 69-81 (13aa)

Nucleotide sequence (SEQ ID No. 96)
ATGAGCCTGCTGGAAGTTATCATTGTTCTTGGCATTATCGGTACGATTGCAGCCG
GTGTCGTGATTCTGGCTCAGCGTGCGTTTGATTCACGTGCTGTGACTGATTTAGTAAC
TAATACAAATACAGTCCGCGTAGCAATGAAAGATGCTTATCAACGTGATGGTAAAT
ATCCAGATTTTGTGGACCCATTAAGCCTTACTGCAAATACAATTAAAACTGATACAA
GCGGAATACCTGCAGCACAGTTAGTTCAGCTTGGGAAAATTACACCAGACGAAGTG
CGTAATAACATTTCTGGCGACTTTATCGCTATTGGCGGTGCTTTAACTTCGAATGGTG
CTCAAGTTAAAAAAGGTTTTGCTATCGAACTTAATGGATTAAGCCAAGAGCAGTGCC
GTTCTATTCTTGGGCAAGTTGGGAATAACTGGGAATATGTTGCTATTGGTACTTCTGC
GTCTGGTTCATATGCCATGACAGCAACTGGTGTAGATATGTCTGTGGCCGCCTCTAC
AACTGTTTTACGCTCTTTAGGTAACGGTGGACAAACAACCTTGACTGCAGACAAAAT
TCTAAGTACCTGTACTGCTCAGGTAAACTCAATTACTTTAGGTAGCCGTTAA

Primers to amplify LngA gene the segment as antibody titration ELISA coating antigen:
CA21-LngA-F: CATG<u>CCATGG</u>GCATGAGCCTGCTGGAAGTTATCATTGTT (NcoI) (SEQ
ID No. 97)

CA21-LngA-R: GAGT<u>CGGCCG</u>CTTTAACGGCTACCTAAAGTAATTGAG (EagI) (SEQ ID
No. 98)

EtpA adhesive subunit
Amino acid sequence (SEQ ID No. 99)
VSEITTGVGNAKATGSVEGEKSPRRGVRAMALSLLSGMMINIAHPAMSANLPTGGQIVA
GSGSIQTPSGNQMNIHQNSQNMVANWNSFDIGKGNTVQFDQPSSSAVALNRVVGGGES
QIMGNLKANGQVFLVNPNGVLFGEGASVSTSGFVASTRDIKNDDFMNRRYTFSGGQKA
GAAIVNQGELTTNAGGYIVLAADRVSNSGTIRTPGGKTVLAA Epitope: 17-27 (11aa)

Nucleotide sequence (SEQ ID No. 100)
ATGAACCGTATATATAAACTGAAGTTTGACAAACGCCGCAACGAACTGGTGGTGG
TGAGTGAAATCACCACCGGCGTGGGTAATGCAAAAGCCACGGGCAGCGTGGAGGGC
GAAAAGTCCCCCGTCGTGGCGTGCGCGCATGGCGCTGAGCCTGCTGTCGGGTATG
ATGATAATGGCCCATCCGGCGATGTCAGCAAACCTGCCGACCGGTGGCCAGATTGT
GGCAGGTTCAGGCAGTATCCAGACGCCTTCCGGCAACCAGATGAATATTCATCAGA
ACAGCCAGAACATGGTGGCCAACTGGAACAGCTTTGACATTGGTAAAGGAAATACG
GTGCAGTTTGACCAGCCCAGCAGCAGTGCGGTGGCGCTGAACGTGTTGTGGGTGG
CGGTGAATCGCAGATTATGGGTAACCTGAAGGCGAATGGTCAGGTGTTCCTGGTTAA
CCCGAACGGCGTGCTGTTTGGTGAGGGGGCCAGTGTCAGCACGTCAGGTTTTGTGGC
ATCGACCCGCGACATTAAAAACGACGACTTCATGAACCGTCGTTACACCTTCAGCGG
CGGACAGAAAGCCGGGGCAGCGATTGTGAACCAGGGGGAACTGACCACAAATGCC
GGTGGCTATATTGTGCTGGCAGCAGACAGGGTCAGCAACAGTGGCACCATCCGTAC
GCCGGGCGGCAAGACCGTCCTGGCGGCCAGCGAGCGCATCACGCTGCAGCTGGATA
ATGGTGGCCTGATGTCCGTGCAGGTGACAGGAGATGTGGTTAATGCCCTGGTGGAA
AACCGCGGTCTGGTCAGTGCCCGGGATGGTCAGGTGTACCTGACCGCCACTTGGTCG
GGGTATGCTGATGAACACGGTACTGAACGTGAGCGGGGTGGTGGAAGCCAGCGGTA
TGCACCGTCAGGACGGTAACATTGTACTGGACGGTGCGACAGTGGTGTGGTGCAC
CTGAGTGGTACCCTGCAGGCGGACAATGCGTCCGGTCAGGGTGGTAAGGTTGTCGT
GCAGGGTAAGAATATTCTGCTGGACAAGGGCAGCAACATCACAGCCAACGGTGGTC
AGGGCGGCGGTGAAGTGTATGTCGGTGGCGGCTGGCAGGGTAAGGACAGCAACATC
CGTAATGCGGACAAGGTGGTGATGCAGGGCGGCGCCCGCATTGACGTTTCTGCAAC
GCAGCAGGGTAACGGCGGTACGGCTGTGCTGTGGTCAGACAGC**TACACCAACTTCC
ATGGTCAGATTA**GCGCGAAGGGCGGTGAGACCGGCGGTAACGGTGGTCGGGTGGA
GACCTCTTCGCACGGTAACCTGCAGGCATTTGGTACGGTCAGTGCATCCGCGAAGAA
AGGCAAGGCGGGTAACTGGCTGCTGGACTCGGCGGATATCACCATTGTGAATGGTA
GCAATGTTAGCAAAACTGAGACGACTCAATCGCCGCCGCACACGCAATTTGCACCC
ACCGCTGCGGGCTCTGCGGTCAGCAATACCAGTATCAACAACAGGCTGAACAACGG
GACCAGTGTCACTATTCTGACCCATCGCACAAGAACAGGCACAGCTCAGGGCGGGA
ATATTACCGTTAATGCGGCAATTAACAAAAGCAACGGAAGTGATGTCAACCTGACG
CTGCAGGCTGGCGGCAACATCACGGTAAACAACAGCATCACGTCCACCGAGGGTAA
GCTGAATGTTAATCTGTCGGGCGCCAGGACCAGCAATGGCAGTATCACCATTAGCA
ATAACGCCAATATAACGACCAATGGTGGGGATATAACTGTTGGGACGACAAATACT
TCAAACCGTGTGAATATATCTATTAATAACACTACCCTGAATGCGTCAAATGGCAAC
ATCCAGTTGACCGGGACCGGGACCGATAGCGGGATTCTGTTTGCTGGCAACAACAG
GCTGACGGCCAGTAACATTGCTCTTACCGGGAACAGTACGAGTGGGAATGCCATCA
ACCTTACAGGCACTGCCACGCTGAATGCCACGAATAACATTACTCTTACCGGGAGCA
GTACGAGTGGGAATGCCATCAACCTTAAAGGCAACAACACGCTGACGGCCAGTAAC
ATTACTCTTACCGGGGAAAGTACGAGTGGGAATGCCATCAACCTTACAGACACTAC
AGGCACTACCACGCTGAATGCCACGAATAACATCACTATGCAGGGGACCCGTGTTC -continued AGATTAAACACTCCAACATCACCGCGGGCAACTTTGCGCTGAATGCGACAGTGGCC
GGCTCTGAAATCAGCAATACCACGCTGACGGCCACCAACAACATCAACCTGGCGGC
TAAGACGAACAGTGCGAGCTCTGGTGTTTACCTGAAAGATGCAAGAATTACATCCA
CCAATGGCAGTATCACGGCTAACGGTACTGCCACAGCAAACGGCAAGGCCACGCAT
CTGGACGGCAACGTCACCCTGAATGCGTCAAATGGCAGAATCAAGTTGACCGGGAA
CGGGCACGGTAGCGCCTCCGGGATTCTGTTTGCTGGCAACAACAGGCTGACGGCCA
GTAACATTGCTCTTACCGGGAACAGTACGAGTGGGAATGCCATCAACCTTACAGGC
ACTGCCACGCTGAATGCCACGAATGACATTACTCTTACCGGGAGCAGTACGAGTGG
GAATGCCATCAACCTTACAGGCACTGCCACGCTGAATGCCACGAATAACATTACTCT
TACCGGGAGCAGTACGAGTGGGAATGC
CATCAACCTTAAAGGCAACAACACGCTGACGGCCAGTAACATTACTCTTACCGGGG
AAAGTACGAGTGGGAATGCCATCAACCTTACAGACACTACAGGCACTACCACGCTG
AATGCCACGAATAACATCACTATGCAGGGGACCCGTGTTCAGATTAAACACTCCAA
CATCACCGCGGGCAACTTTGCGCTGAATGCGACAGTGGCCGGCTCTGAAATCAGCA
ATACCACGCTGACGGCCACCAACAACATCAACCTGGCGGCTAAGACGAACAGTGCG
AGCTCTGGTGTTTACCTGAAAGATGCAAGAATTACATCCACCAATGGCAGTATCACG
GCTAACGGTACTGCCACAGCAAACGGCAAGGCCACGCATCTGGACGGCAACGTCAC
CCTGAATGCGTCAAATGGCAGAATCAAGTTGACCGGGAACGGGCACGGTAGCGCCT
CCGGGATTCTGTTTGCTGGCAACAACAGGCTGACGGCCAGTAACATTGCTCTTACCG
GGAACAGTACGAGTGGGAATGCCATCAACCTTACAGGCACTGCCACGCTGAATG
CCACGAATGACATTACTCTTACCGGGAGCAGTACGAGTGGGAATGCCATCAACCTTA
CAGGCACTGCCACGCTGAATGCCACGAATAACATTACTCTTACCGGGAGCAGTACG
AGTGGGAATGCCATCAACCTTAAAGGCAACAACACGCTGACGGCCAGTAACATTAC
TCTTACCGGGGAAAGTACGAGTGGGAATGCCATCAACCTTACAGACACTACAGGCA
CTACCACGCTGAATGCCACGAATAACATCACTATGCAGGGGACCCGTGTTCAGATTA
AACACTCCAACATCACCGCGGGCAACTTTGCGCTGAATGCGACAGTGGCCGGCTCT
GAAATCAGCAATACCACGCTGACGGCCACCAACAACATCAACCTGGCGGCTAAGAC
GAACAGTGCGAGCTCTGGTGTTTACCTGAAAGATGCAAGAATTACATCCACCAATG
GCAGTATCACGGCTAACGGTACTGCCACAGCAAACGGCAAGGCCACGCATCTGGAC
GGCAACGTCACCCTGAATGCGTCAAATGGCAGAATCAAGTTGACCGGGAACGGG
CACGGTAGCGCCTCCGGGATTCTGTTTGCTGGCAACAACAGGCTGACGGCCAGTAA
CATTGCTCTTACCGGGAACAGTACGAGTGGGAATGCCATCAACCTTACAGGCACTGC
CACGCTGAATGCCACGAATGACATTACTCTTACCGGGAGCAGTACGAGTGGGAATG
CCATCAACCTTACAGGCACTGCCACGCTGAATGCCACGAATAACATTACTCTTACCG
GGAGCAGTACGAGTGGGAATGCCATCAACCTTAAAGGCAACAACACGCTGACGGCC
AGTAACATTACTCTTACCGGGGAAAGTACGAGTGGGAATGCCATCAACCTTACAGA
CACTACAGGCACTACCACGCTGAATGCCACGAATAACATCACTATGCAGGGGACCC
GTGTTCAGATTAAACACTCCAACATCACCGCGGGCAACTTTGCGCTGAATGCGACAG
TGGCCGGCTCTGAAATCAGCAATACCACGCTGACGGCCACCAACAACATCAACCTG
GCGGCTAAGACGAACAGTGCGAGCTCTGGTGTTTACCTGAAAGATGCAAGAATTAC
ATCCACTAATGGCAGTATCACGACTAACGGTACTGCCACAGCAAACGGCAAGGCCA
CGCATCTGGACGGCAACGTCACCCTGAATGCGTCAAATGGCAGAATCAAGTTGACC
GGGAACGGGCACGGTAGCGCCTCCGGGATTCTGTTTGCTGGCAACAACAGGCTGAC
GGCCAGTAACATTGCTCTTACCGGGAACAGTACGAGTGGGAATGCCATCAACCTTAC
AGGCACTGCCACGCTGAATGCCACGAATGACATTACTCTTACCGGGAGCAGTACGA
GTGGGAATGCCATCAACCTTACAGGCACTGCCACGCTGAATGCCACGAATAACATT
ACTCTTACCGGGAGCAGTACGAGTGGGAATGCCATCAACCTTAAAGGCAACAACAC
GCTGACGGCCAGTAACATTACTCTTACCGGGGAAAGTACGAGTGGGAATGCCATCA
ACCTTACAGACACTACAGGCACTACCAC
GCTGAATGCCACGAATAACATCACTATGCAGGGGACCCGTGTTCAGATTAAACACTC
CAACATCACCGCGGGCAACTTTGCGCTGAATGCGACAGTGGCCGGCTCTGAAATCA
GCAATACCACGCTGACGGCCACCAACAACATCAACCTGGCGGCTAAGACGAACAGT
GCGAGCTCTGGTGTTTACCTGAAAGATGCAAGAATTACATCCACCAATGGCAGTATC
ACGGCTAACGGTACTGCCCCAGCAAACGACAATGCCACGTATCTGGACGGCAACGT
CACCCTGAATGCGTCAAATGGCAGCATCAAGTTGACCGGGAACGGGAACGGTAGCA
CCTCCGGGATTCTGTTTGCTGGCAACAACACGCTGACGGCCAGTAACATTACTCTTA
CCGGGAACAGTGAGGTGTACTGGCAATAG Primers to amplify the segment as antibody titration ELISA coating antigen:
EtpA-F: CTAGCTAGCTAGATGAACCGTATATATAAACTG (NheI) (SEQ ID No. 101)

EtpA-R: GAGTCGGCCGCTTTATAATCTGACCATGGAAGTTGGTGTA(Eag I) (SEQ ID No. 102)

EaeH subunit
Amino acid sequence: (SEQ ID No. 103)
MSHYKTGHKQPRFRYSVLARCVAWANISVQVLFPLAVTFTPVMAARAQHAVQPRLSM
GNTTVTADNNVEKNVASFAANAGTFLSSQPDSDATRNFITGMATAKANQEIQEWLGKY
GTARVKLNVDKDFSLKDSSLEMLYPIYDTPTNMLFTQGAIHRTDDRTQSNIGFGWRHFS
GNDWMAGVNTFIDHDLSRSHTRIGVGAEYWRDYLKLSANGYIRASGWKKSPDIEDYQE
RPANGWDIRAEGYLPAWPQLGASLMYEQYYGDEVGLFGKDKRQKDPHAISAEVTYTP
V Epitope: 222-233 (12aa)

Nucleotide sequence (SEQ ID No. 104)
ATGTCACATTATAAAACAGGTCATAAACAACCACGATTTCGTTATTCAGTTCTGGCCCG
CTGCGTGGCGTGGGCAAATATCTCTGTTCAGGTTCTTTTTCCACTCGCTGTCACCTTTA
CCCCAGTAATGGCGGCACGTGCGCAGCATGCGGTTCAGCCACGGTTGAGCATGGGA

-continued

AATACTACGGTAACTGCTGATAATAACGTGGAGAAAAATGTCGCGTCGTTTGCCGCA
AATGCCGGGACATTTTTAAGCAGTCAGCCAGATAGCGATGCGACACGTAACTTTATTA
CCGGAATGGCCACAGCTAAAGCTAACCAGGAAATACAGGAGTGGCTCGGGAAATATG
GTACTGCGCGCGTCAAACTGAATGTCGATAAAGATTTCTCGCTGAAGGATTCTTCGCT
GGAAATGCTTTATCCGATTTATGATACGCCGACAAATATGTTGTTCACTCAGGGGGCAA
TACATCGTACAGACGATCGTACTCAGTCAAATATTGGTTTTGGCTGGCGTCATTTTTCA
GGAAATGACTGGATGGCGGGGGTGAATACTTTTATCGATCATGATTTATCCCGTAGTCA
TACCCGCATTGGTGTTGGTGCGGAATACTGGCGCGATTATCTGAAACTGAGCGCCAAT
GGTTATATTCGGGCTTCTGGCTGGAAAAAATCGCCGGATATTGAGGATTATCAGGAA
CGCCCGGCGAATGGCTGGGATATTCGTGCTGAGGGCTATTTACCCGCCTGGCCGCAGC
TTGGCGCAAGCCTGATGTATGAACAGTATTATGGCGATGAAGTCGGGCTGTTTGGTAA
AGATAAGCGCCAGAAAGACCCGCATGCTATTTCTGCCGAGGTGACCTATACGCCAGT
GCCTCTTCTGACACTGAGCGCCGGGCATAAGCAGGGCAAGAGTGGTGAGAATGACA
CTCGCTTTGGCCTGGAAGTTAATTATCGGATTGGCGAACCTCTGGCGAAACAACTC
GATACAGACAGCATTCGCGAGCGTCGGGTACTGGCAGGCAGCCGCTATGACCTGGTT
GAGCGTAATAACAACATCGTTCTTGAGTACCGCAAATCTGAAGTGATCCGTATTGCTC
TGCCTGAACGTATTGAAGGTAAGGGTGGTCAGACACTTTCCCTGGGGCTTGTGGTCA
GCAAAGCAACTCACGGACTGAAAAATGTGCAGTGGGAAGCGCCGTCATTACTGGCT
GAGGGTGGCAAAATTACCGGTCAGGGTAGTCAGTGGCAAGTAACGCTCCCGGCTTAT
CGTCCAGGCAAAGACAATTATTATGCGATTTCTGCGGTTGCCTACGATAACAAAGGCA
ATGCCTCAAAACGCGTGCAGACAGAGGTGGTCATTACCGGAGCAGGTATGAGCGCCG
ATCGCACGGCGTTAACGCTTGACGGTCAGAGCCGTATTCAAATGCTTGCTAACGGTAA
TGAGCAAAGACCGCTGGTGCTGTCTCTGCGCGACGCCGAGGGGCAGCCAGTCACGG
GCATGAAAGATCAGATCAAGACTGAACTAGCCTTCAAACCGGCTGGAAATATTGTGA
CTCGTTCCCTGAAGGCCACTAAATCACAGGCAAAGCCAACACTGGGTGAGTTCACCG
AAACTGAAGCAGGGGTGTATCAGTCTGTCTTTACTACCGGAACGCAGTCAGGTGAGG
CAACGATTACTGTTAGCGTTGATGGCATGAGCAAAACCGTCACTGCAGAACTGCGGG
CCACGATGATGGATGTGGCAAACTCCACCCTGAGCGCTAACGAGCCGTCAGGTGATG
TGGTTGCTGATGGTCAGCAAGCCTATACGTTGACGTTGACTGCGGTGGACTCCGAGG
GTAATCCGGTGACGGGAGAAGCCAGCCGCTTGCGATTTGTTCCGCAAGACACTAATG
GTGTAACCGTTGGTGCCATTTCGGAAATAAAACCAGGCGTTTACAGCGCCACGGTTTC
TTCGACCCGTGCCGGAAACGTTGTTGTGCGTGCTTTCAGCGAGCAGTATCAGCTGGG
CACATTACAACAAACGCTGAAGTTTGTTGCCGGTCCGCTTGATGCAGCACATTCGTCC
ATCCCCCTGAATCCTGATAAACCGGTGGTTGGCGGTACAGTTACGGCAATCTGGACGG
CAAAAGATGCCTATGACAACCCTGTGACCAGCCTCACGCCGGAAGCGCCGTCATTAG
CGGGTGCCGCTGCTGTAGGTTCTACGGCATCTGGCTGGACAAATAATGGTGATGGGAC
GTGGACTGCGCAGATTACTCTCGGCTCTACGGCGGGTGAATTAGAAGTTATGCCGAA
GCTAAATGGACAGGATGCGGCAGCAAATGCGGCAAAAGTAACCGTGGTGGCTGATGC
GTTATCTTCAAACCAGTCGAAAGTCTCTGTCGCAGAAGATCACGTAAAAGCCGGCGA
AAGCACAACCGTGACGCTTATTGCAAAAGATGCACATGGCAACACTATCAGTGGTCT
TTCGTTGTCGGCAAGTTTGACGGGGACCGCCTCTGAAGGGGCGACCGTTTCCAGTTG
GACCGAAAAAGGTGACTGTTCCTATGTTGCTACGTTAACTACAGGCGGAAAGACGGG
CGAGCTTCGTGTCATGCCGCTCTTCAACGGCCAGCCAGCAGCCACCGAAGCCGCGCA
GTTGACGGTCATCGCCGGAGAGATGTCATCAGCGAACTCTACGCTTGTTGCGGACAAT
AAGGCTCCGACCGTCAAAATGACGACGGAACTCACCTTCACCGTGAAGGATGCGTAC
GGGAACCCGGTCACCGGGCTGAAGCCAGATGCACCAGTGTTTAGCGGTGCCGCCAG
CACGGGGAGTGAGCGTCCTTCAGCAGGAAACTGGACAGAGAAAGGTAATGGGGTCT
ACGTGGCGACCTTAACGCTGGGATCTGCCGCGGGTCAGTTGTCTGTGATGCCGCGAG
TGAACGGCCAAAATGCCGTTGCTCAGCCACTGGTGCTGAACGTTGCAGGTGACGCAT
CTAAGGCTGAGATTCGTGATATGACAGTGAAGGTTAATAACCAACTGGCTAATGGACA
GTCTGCTAACCAGATAACCCTGACCGTCGTGGACAGCTATGGTAACCCGTTGCAGGG
GCAAGAAGTTACGCTGACTTTACCGCAGGGTGTGACCAGCAAGACGGGGAATACAGT
AACAACCAATGCGGCAGGGAAAGTGGACATTGAGCTTATGTCAACGGTTGCGGGGG
AACACAGCATCACGGCCTCAGTGAATAATGCTCAGAAGACGGTTACGGTGAAATTCA
AGGCGGATTTCAGTACCGGTCAGGCGACCCTGGAGGTTGATGGCAGCACGCCAAAA
GTGGCAAACGACAATGATGCCTTTACGCTGACGGCAACGGTTAAGGATCAATACGGC
AACCTTCTGCCTGGCGCTGTGGTCGTCTTTAATCTGCCTCGGGGCGTCAAACCGCTTG
CAGACGGTAATATCATGGTGAACGCCGACAAGGAGGGTAAAGCGGAACTGAAAGTG
GTCTCCGTGACTGCCGGAACGTATGAGATCACGGCGTCGGCAGGAAATGACCAGCCT
TCGAATGCGCAGTCTGTAACGTTTGTGGCCGATAAGACTACGGCGACCATCTCCAGTA
TTGAGGTGATTGGCAACCGTGCAGTGGCGGATGGCAAAACCAAACAGACGTATAAA
GTTACGGTGACTGATGCCAATAACAACCTGTTGAAGGATAGCGACGTGACGCTGACT
GCCAGCTCGGAAAATTTAGTTCTGGATCCTAAAGGGACGGCGAAAACTAATGAGCAA
GGACAGGCTGTTTTCACCGGCTCTACCACTATCGCAGCGACATATACACTCACGGCGA
AAGTGGAACAGGCCAACGGTCAGGTATCGACGAAAACTGCTGAATCTAAATTCGTCG
CGGATGATAAAAACGCGGTGCTCGCCGCATCTCCAGAACGTGTAGATTCTCTGGTGG
CGGACGGGAAGACTACTGCAACAATGACGGTTACCCTGATGGCGGGAGTCAATCCCG
TAGGAGGAAGTATGTGGGTCGACATTGAGGCTCCGGAAGGAGTGACGGAGAAGGAT
TATCAATTCCTGCCGTCGAAGGCTGACCATTTCTCAGGTGGGAAAATCACGCGTACAT
TTAGTACCAGCAAGCCAGGTGTCTATACGTTCACATTCAACGCACTGACGTATGGCGG
GTACGAAATGACGCCTGTGAAGGTGACAATTAACGCCGTTGCTGCAGAGACTGAAAA
TGGCGAGGAGGAGATGCCATAA

Primers to amplify the segment as antibody titration ELISA coating antigen
EaeH-F: CATGCCATGGAAATGGGAAATACTACGGTAACTGC (NcoI) (SEQ ID No. 105)

EaeH-R: GAGTCGGCCGCATTAGGTTCGCCAATCCGATAATTAACTT(EagI) (SEQ ID No. 106)

Adult female mice, 10 per group, were subcutaneously (SC) immunized with 40 μg recombinant CFA MEFA-II protein, with 2 μg dmLT adjuvant. Immunized mice received two boosters in an interval of two weeks. Two weeks after the final booster, mice were anesthetized and exsanguinated. A group of 10 mice without immunization were used as the control. Mouse serum samples were used for antibody titration and antibody adherence inhibition assay.

Antibody titration ELISAs using recombinant subunit proteins as coating antigens (400 ng per well) was performed. Serum samples from each mouse from the immunized group were detected great titers of anti-CS7, -CS12, -CS14, -CS17, -CS19, -CS21, -EaeH and anti-EtpA IgG antibodies.

Results and Conclusions

Figure 7:
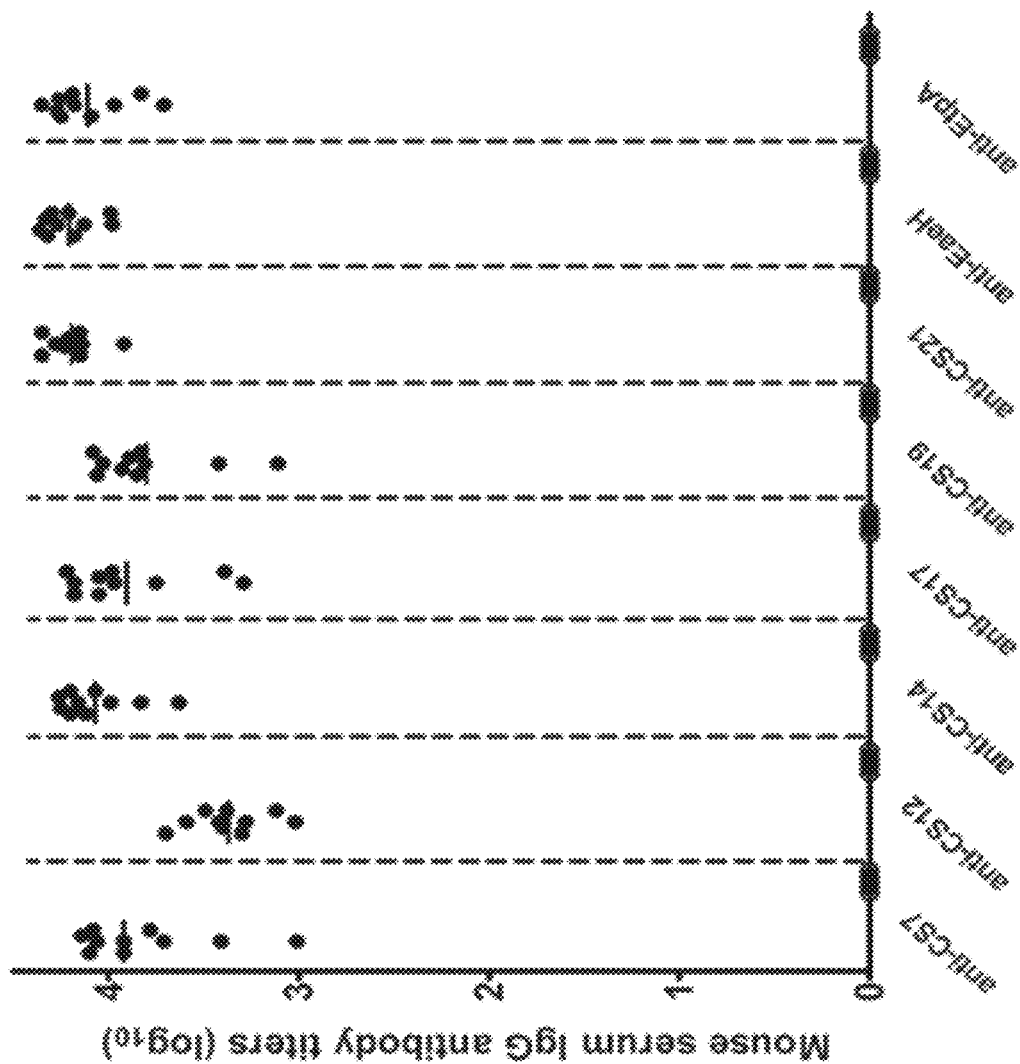
FIG. 7 is a plot of serum IgG antibody titers ($\log_{10}$) for anti-CS7, anti-CS12, anti-CS14, anti CS17, anti-CS19, anti-CS21, anti-EaeH and anti-EtpA IgG antibodies from mice subcutaneously immunized with major subunit CFA MEFA-II, where each dot represented an IgG titer from an individual mouse and bars indicated mean titers.
Figure 8:
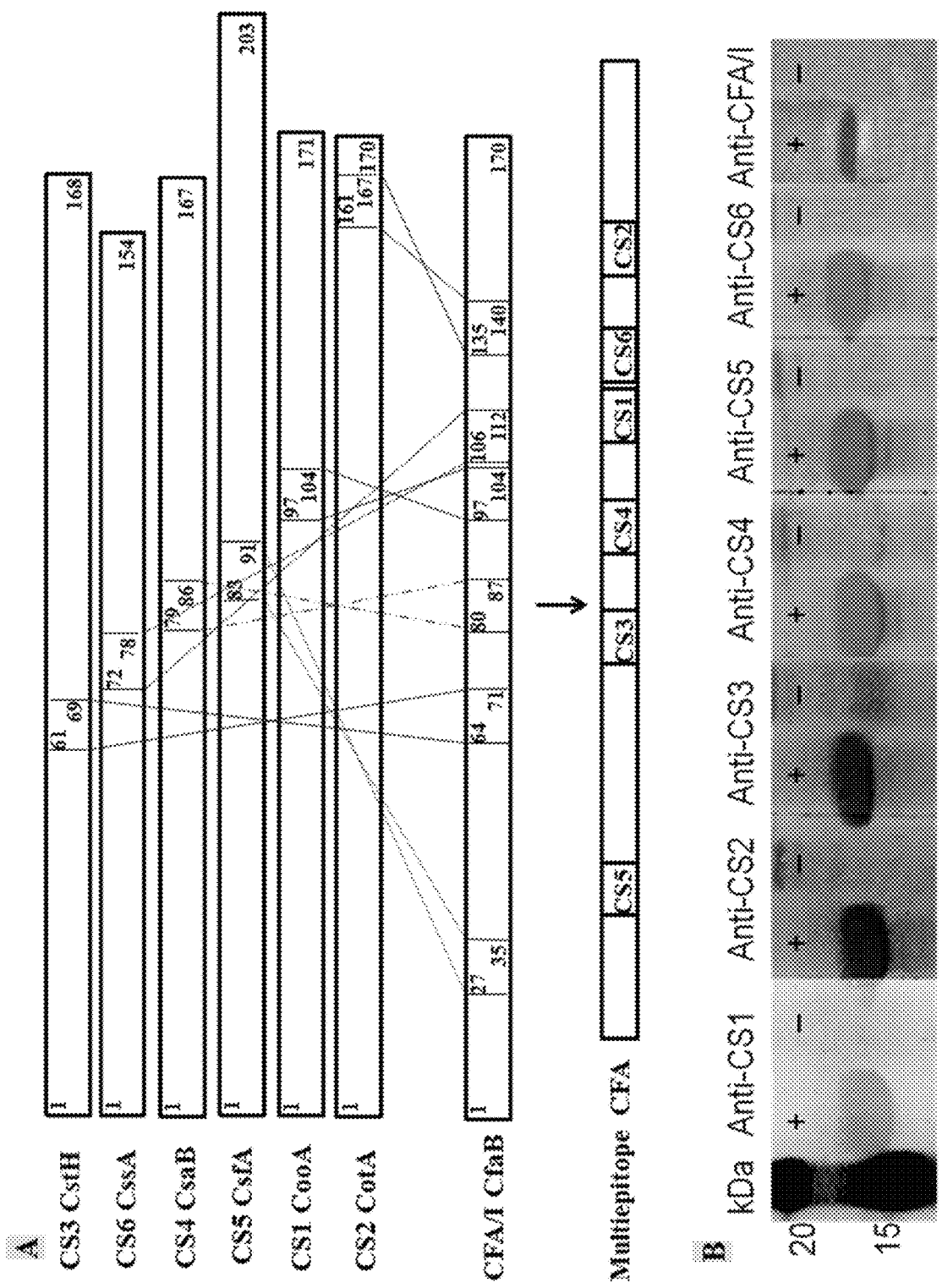
FIG. 8 is an illustration of a MEFA of the present disclosure illustrating the epitopes being incorporated into the backbone.

All mice in the immunization group developed antibodies specific to CS7, CS12, CS14, CS17, CS19, CS21, EaeH and EtpA. No antigen-specific antibodies were detected from serum samples of the control mice. Moreover, serum samples from the mice SC immunized with CFA MEFA-II showed antibody neutralization activities. ETEC bacteria expressing CS7, CS12, CS14, CS17, CS19, CS21, EaeH, or EtpA adhesin, after incubated with the serum samples of the immunized mice, showed a significant reduction in adherence to Caco-2 cells, compared the bacteria incubated with the serum samples of the control mice. These results are show in FIG. 7, where the IgG antibody titers are illustrated for each mouse, where each dot represented a IgG titer from an individual mouse and the bars indicated mean titers.

TABLE 5

Mouse serum antibody in vitro adherence inhibition assay results. Caco-2cells ($5 \times 10^5$) were incubated with each ETEC bacteria strain expressing a different adhesion (in PBS), ETEC bacteria premixed with serum of the control mice, or ETEC bacteria premixed with serum of the mice immunized with CFA MEFA-II

| E.coli strains | PBS | serum of control mice | serum of immunized mice |
|---|---|---|---|
| H10407-EaeH/EtpA/CFA/I/LT/STa ($\times 10^2$) | 136.8 ± 5.6 | 130.8 ± 4.4 | 44 ± 2.7<br>p < 0.001 |
| JF2327, CS7/LT ($\times 10^3$) | 77.2 ± 3.1 | 75 ± 3.0 | 30.8 ± 2.3<br>p < 0.001 |
| JF2363, CS7/EatA/LT ($\times 10^3$) | 105.6 ± 5.1 | 100.8 ± 4.3 | 33.2 ± 1.9<br>p < 0.001 |
| 3276, CS12/CS20/LT/STa ($\times 10^3$) | 107 ± 6.3 | 100 ± 5.0 | 31.4 ± 2.6<br>p < 0.001 |
| 3309, CS12/CS20/CS21/LT/STa ($\times 10^3$) | 145 ± 9.4 | 140 ± 7.1 | 37 ± 2.9<br>p < 0.001 |
| E7476A, CS14 ($\times 10^2$) | 131.8 ± 3.1 | 127.4 ± 7.7 | 63.8 ± 3.2<br>p < 0.001 |
| JF2125, CS14/EtpA/LT ($\times 10^2$) | 75.4 ± 2.3 | 73.8 ± 5.5 | 15.6 ± 1.5<br>p < 0.001 |
| E20738A, CS17 ($\times 10^2$) | 117.8 ± 8.0 | 115 ± 10.8 | 50.4 ± 3.2<br>p < 0.001 |
| JF2350, CS17/EtpA/EatA/LT ($\times 10^2$) | 219.8 ± 9.2 | 208.4 ± 9.6 | 133.2 ± 5.0<br>p < 0.001 |
| D526-1, CS19 ($\times 10^2$) | 182.4 ± 10.4 | 179.4 ± 8.7 | 61 ± 3.4<br>p < 0.001 |
| JF2101, CS21/EtpA/EatA/STa ($\times 10^2$) | 45.6 ± 3.0 | 40.6 ± 1.8 | 14.8 ± 1.5<br>p < 0.001 |
| JF2318, EtpA/STa ($\times 10^2$) | 91.8 ± 5.8 | 87.2 ± 4.5 | 33.4 ± 3.5<br>p < 0.001 |
| JF1389, EtpA/CS5/CS6/LT/STa ($\times 10^2$) | 43 ± 2.3 | 41 ± 4.4 | 18.2 ± 2.6<br>p < 0.001 |

The invention claimed is:

1. A multiepitope fusion antigen selected from the group consisting of:
   (a) a multiepitope fusion antigen comprising a CfaE backbone having 3 or more different epitopes therein, selected from the group consisting of CFA/I, CS1, CS2, CS3, CS4, CS5, CS6, CS7, CS12, CS14, CS17, CS19, CS21, EtpA, and EaeH;
   (b) a multiepitope fusion antigen comprising a CS14 backbone having 3 or more different epitopes therein, selected from the group consisting of CFA/I, CS1, CS2, CS3, CS4, CS5, CS6, CS7, CS12, CS14, CS17, CS19, CS21, EtpA, and EaeH;
   (c) a major subunit CFA multiepitope fusion antigen comprising a CS21 backbone having 3 or more different epitopes therein, selected from the group consisting of CS7, CS12, CS14, CS17, CS19, CS21, EtpA, and EaeH; and
   (d) any combination of (a), (b), or (c) thereof
   wherein each of said epitopes and/or backbones are from adhesin tips, adhesive subunits or major structural subunits of *Escherichia coli*.

2. An immunogenic composition comprising the multiepitope fusion antigen of claim 1 and at least one additional component selected from the group consisting of a pharmaceutically acceptable vehicle, adjuvant, carrier, and any combination thereof.

3. A method of reducing the clinical signs of Enterotoxigenic *Escherichia coli* comprising the steps of administering the multiepitope fusion antigen of claim 1 to a human or animal in need thereof.

4. The multiepitope fusion antigen of claim 1, wherein the multiepitope fusion antigen comprises a CfaE backbone comprising the epitopes CFA/I, CS1, CS2, CS3, CS4, CS5, CS6, CS21, and EtpA.

5. The multiepitope fusion antigen of claim 1, wherein the multiepitope fusion antigen comprises a CS14 backbone comprising the epitopes CS12, CS17, CS19, and EaeH.

6. The subunit CFA multiepitope fusion antigen of claim 1, wherein the major subunit CFA multiepitope fusion antigen comprises a CS21 backbone comprising the epitopes CS7, CS12, CS14, CS17, CS19, EtpA, and EaeH.

7. The multiepitope fusion antigen of claim 1, further comprising an additional element selected from the group consisting of heat liable toxin (LT), heat stable toxin (STa), an epitope from adhesin of enteroaggregative *E. coli* (EAEC), epitopes of cholera, epitopes of rotavirus, and any combination thereof.

8. The multiepitope fusion antigen of claim 1, further comprising an additional element selected from the group consisting of a pharmaceutically acceptable vehicle, adjuvant, carrier and any combination thereof.

9. The method of claim 3, wherein the administering step comprises intradermal, intramuscular, or subcutaneous administration.

10. A method of reducing the adhesion of ETEC to the gut comprising the steps of administering the multiepitope fusion antigen of claim 1 to a human or animal in need thereof.

11. The adhesin tip multiepitope fusion antigen of claim 1, wherein:
   the CS1 epitope is selected from the group consisting of an amino acid sequence having at least 90% sequence identity with either SEQ ID Nos 47 or 37 or that is encoded by a sequence having at least 90% sequence identity with SEQ ID No. 55;
   the CS2 epitope is selected from the group consisting of an amino acid sequence having at least 90% sequence identity with either SEQ ID Nos 47 or 37 or that is encoded by a sequence having at least 90% sequence identity with SEQ ID No. 55;
   the CS3 epitope is selected from the group consisting of an amino acid sequence having at least 90% sequence identity with either SEQ ID Nos 47 or 37 or that is encoded by a sequence having at least 90% sequence identity with SEQ ID No. 55;
   the CS4 epitope is selected from the group consisting of an amino acid sequence having at least 90% sequence identity with either SEQ ID Nos 47 or 37 or that is encoded by a sequence having at least 90% sequence identity with SEQ ID No. 55;

the CS5 epitope is selected from the group consisting of an amino acid sequence having at least 90% sequence identity with either SEQ ID Nos 47 or 37 or that is encoded by a sequence having at least 90% sequence identity with SEQ ID No. 55;

the CS6 epitope is selected from the group consisting of an amino acid sequence having at least 90% sequence identity with either SEQ ID Nos 47 or 37 or that is encoded by a sequence having at least 90% sequence identity with SEQ ID No. 55;

the CS7 epitope is selected from the group consisting of an amino acid sequence having at least 90% sequence identity with either SEQ ID Nos 47 or 37 or that is encoded by a sequence having at least 90% sequence identity with SEQ ID No. 55;

the CS12 epitope is selected from the group consisting of an amino acid sequence having at least 90% sequence identity with either SEQ ID Nos 47 or 37 or that is encoded by a sequence having at least 90% sequence identity with SEQ ID No. 55;

the CS14 epitope is selected from the group consisting of an amino acid sequence having at least 90% sequence identity with either SEQ ID Nos 47 or 37 or that is encoded by a sequence having at least 90% sequence identity with SEQ ID No. 55;

the CS17 epitope is selected from the group consisting of an amino acid sequence having at least 90% sequence identity with either SEQ ID Nos 47 or 37 or that is encoded by a sequence having at least 90% sequence identity with SEQ ID No. 55;

the CS19 epitope is selected from the group consisting of an amino acid sequence having at least 90% sequence identity with either SEQ ID Nos 47 or 37 or that is encoded by a sequence having at least 90% sequence identity with SEQ ID No. 55;

the CS21 epitope is selected from the group consisting of an amino acid sequence having at least 90% sequence identity with either SEQ ID Nos 47 or 37 or that is encoded by a sequence having at least 90% sequence identity with SEQ ID No. 55;

the EtpA epitope is selected from the group consisting of an amino acid sequence having at least 90% sequence identity with either SEQ ID Nos 47 or 37 or that is encoded by a sequence having at least 90% sequence identity with SEQ ID No. 55; and the EaeH epitope is selected from the group consisting of an amino acid sequence having at least 90% sequence identity with either SEQ ID Nos 47 or 37 or that is encoded by a sequence having at least 90% sequence identity with SEQ ID No. 55.

12. The adhesin tip multiepitope fusion antigen of claim 1, wherein:

the CfaE backbone is selected from the group consisting of an amino acid sequence having at least 90% sequence identity with SEQ ID No 46;

the CS14 backbone is selected from the group consisting of an amino acid sequence having at least 90% sequence identity with any one of SEQ ID Nos 21, 23, 26, or 70; or the CS21 backbone is selected from the group consisting of an amino acid sequence having at least 90% sequence identity with SEQ ID No 95.

13. The adhesin tip multiepitope fusion antigen of claim 1, wherein the *Escherichia coli* is enterotoxigenic.

* * * * *